(12) United States Patent
Wu et al.

(10) Patent No.: US 8,889,147 B2
(45) Date of Patent: Nov. 18, 2014

(54) DNA VACCINE AGAINST MULTITYPES OF AVIAN INFLUENZA VIRUSES AND INFLUENZA VIRUS-LIKE PARTICLES COMPRISING ADJUVANT-FUSED M2 PROTEIN

(75) Inventors: Suh-Chin Wu, Hsinchu (TW); Shih-Chang Lin, Hsinchu (TW)

(73) Assignee: National Tsing Hua University, Hsin Chu (TW)

( * ) Notice: Subject to any disclaimer, the term of this patent is extended or adjusted under 35 U.S.C. 154(b) by 148 days.

(21) Appl. No.: 13/449,654

(22) Filed: Apr. 18, 2012

(65) Prior Publication Data

US 2013/0280296 A1 Oct. 24, 2013

(51) Int. Cl.
*A61K 39/145* (2006.01)
*A61P 31/20* (2006.01)
*C07K 2/00* (2006.01)

(52) U.S. Cl.
USPC ........ 424/209.1; 530/402; 530/350; 536/23.1

(58) Field of Classification Search
CPC .... C12N 15/81; C12N 9/2488; C12P 21/005; A61K 38/00
See application file for complete search history.

(56) References Cited

PUBLICATIONS

Hai et al. (Journal of Virology, May 2012. vol. 86, p. 5774-5781.*
Medina et al. May 2013, vol. 5, p. 1-12.*
Gubareva et al. Journal of General Virology, 2002, vol. 83, p. 2683-2692.*
Wei, Hung-Ju, et al., Fabrication of influenza virus-like particles using M2 fusion proteins for imaging single viruses and designing vaccines, Vaccine 29 (2011): 7163-7172.
Lin, Shih-Chang, et al., Recombinant Trimeric HA Protein Immunogenicity of H5N1 Avian Influenza Viruses and Their Combined Use with Inactivated or Adenovirus Vaccines, PLoS One 6 (2011): e20052.
Huang, Ming-Hsi, et at., Emulsified Nanoparticles Containing Inactivated Influenza Virus and CpG Oligodeoxynucleotides Critically Influences the Host Immune Responses in Mice, PLoS One 5 (2010): e12279.
Yang, Zhi-Yong, et al., Immunization by Avian H5 Influenza Hemagglutinin Mutants with Altered Receptor Binding Specificity, Science 317 (2007): 825-828.
Yang, Hua, et al., Structures of Receptor Complexes of a North American H7N2 Influenza Hemagglutinin with a Loop Deletion in the Receptor Binding Site, PLoS Pathog 6 (2010): e1001081.

* cited by examiner

*Primary Examiner* — Agnieszka Boesen
(74) *Attorney, Agent, or Firm* — Hannah M. Tien

(57) ABSTRACT

A DNA vaccine comprising hyperglycosylated mutant HA gene, which is derived from avian influenza virus, is provided. A DNA vaccine composition comprising: (a) the DNA vaccine; and (b) a booster is also provided. An influenza virus-like particle comprising adjuvant-fused M2 protein is further provided. A method for eliciting an immune response against a plurality of avian influenza virus subtypes in a subject, comprising delivering the DNA vaccine or the DNA vaccine composition to tissue of the subject is also provided.

9 Claims, 22 Drawing Sheets
(2 of 22 Drawing Sheet(s) Filed in Color)

BacHA-M1

B

M1 ◁ p10 ⊢ pH ▷ HA

BacHA-M1

NA ◁ p10

BacNA

C

M1 ◁ p10 ⊢ pH ▷ HA

BacHA-M1

NA ◁ p10 ⊢ pH ▷ M2

BacM2-NA

A

B ically anti-

DNA VACCINE AGAINST MULTITYPES OF AVIAN INFLUENZA VIRUSES AND INFLUENZA VIRUS-LIKE PARTICLES COMPRISING ADJUVANT-FUSED M2 PROTEIN

FIELD OF THE INVENTION

The present invention relates to a DNA vaccine. More specifically, the present invention relates to a DNA vaccine comprising hyperglycosylated antigen. The present invention also relates to a DNA vaccine composition and a method for eliciting an immune response against multiple avian influenza virus subtypes in a subject using the same. The invention further relates to an influenza virus-like particle comprising adjuvant-fused M2 protein.

BACKGROUND OF THE INVENTION

Highly pathogenic avian influenza (HPAI) H5N1 viruses and their capacity for transmission from birds to humans have raised worldwide concerns about a potential forthcoming human pandemic. With the continued spread of H5N1 influenza virus, new virus strains have emerged and will continue to change and evolve in the future. The World Health Organization has classified the H5N1 viruses isolated recently into 10 clades (or sublineages) based on the phylogenetic analysis of viral hemagglutinin (HA) sequences of H5N1 viruses. With the continuous threat of a new influenza pandemic arising from avian reservoirs, the development of broadly protective vaccines is particularly important. To date, the broadly protective H5N1 vaccines have been mainly achieved using novel adjuvant formulations.

However, the inherent nature of influenza virus antigenic changes has not been taken into accounts in the immunogen designs for developing broadly protective H5N1 vaccines. Refocusing antibody responses have been proposed by designing the immunogens that can preserve the overall fold of the immunogen structure but selectively mutate the "undesired" antigenic sites that are highly variable (escape mutants evade protective immune responses), immunosuppressive (downregulate the immune response to the infection), cross-reactive (the immune response induces a reaction to a protein resembling the immunogen). The immunogen design by refocusing antibody responses has been applied for HIV-1 vaccines using the hyperglycosylated HIV-1 gp120 immunogens where the undesired eptiopes are masked by selective incorporations of N-linked glycans. The glycan masking strategy has been also recently reported to design influenza virus vaccines that can enhance the antibody responses against a broad range of H3N2 intertypic viruses. However, there is no report for the use of glycan-masking immunogen design for H5N1 vaccines.

DNA vaccine has been considered as the revolutionary vaccinology with the advantages in offering genetically antigen design, time to manufacturing, long stability without the need for cold chains supply, and the immunogenicity predominantly elicited by T cells through the endogenerous antigen processing pathways. However, the apparent low immunogenicity of DNA vaccines in large animals (including humans) has been overcome using novel delivery systems such as gene-guns or electroporation. Additionally, the DNA vaccine-elicited immune responses can be further augmented using the heterologous prime-boost immunization regimen where the booster dose uses a different vaccine format containing the same or similar antigens. Examples of DNA vaccine prime-boost immunization strategy has been reported for the inactivated influenza virus, live-attenuated influenza virus, recombinant adenovirus, virus-like particles (VLPs) and recombinant subunit proteins in adjuvants. Furthermore, human vaccines receiving the H5 DNA vaccine priming followed by a booster with inactivated H5N1 vaccine were found to enhance the protective antibody responses (HAI) and in some cases induce the haemagglutinin-stem-specific neutralizing antibodies.

Influenza VLPs are noninfectious and have a size and morphology that are similar to those of native virion structures, but they do not contain the genomic RNAs for virus replication. The assembly of influenza VLPs depends on the interactions of M1 proteins and/or other viral surface proteins, such as HA, NA, and M2, with the cellular lipid membranes. The interactions of M1 protein with the cytoplasmic tails of HA and NA spikes can increase the lipid membrane binding of M1 proteins in assembling influenza virus. The interactions of HA and NA with the M1 protein can also reduce the formation of elongated intracellular immature particles and improve the secretion of spherical mature VLPs. Additionally, the cytoplasmic tails of M2 protein, by interacting with the M1 protein, further promote the budding and release of the influenza virions. Recently, the M2 protein was found to act as the plasma membrane-targeting signal for the budding and egress of influenza virions. Host cell proteins can be recruited into the VLPs, as recently shown by LC/MS/MS analyses. Therefore, the biosynthesis of influenza VLPs is a self-assembly process that involves complex interactions of viral and cellular components.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention can be more fully understood by reading the subsequent detailed descriptions and examples with references made to the accompanying drawing, wherein:

FIG. 9 shows neutralizing activities of sera from immunized mice by the (A) HI and (B) NT titers against the NIBRG-14 (clade 1) H5N1 influenza virus. For calculation purposes, an undetectable level was scored as a titer equal to one. Individual titer (points) and geomean (lines) was given for each group. Asterisks indicate a statistically significant difference ($p<0.05$).

FIG. 10 shows neutralizing activities of sera from immunized mice by the (A) HI and (B) NT titers against the Mongolia/2/2006 (clade 2.2) H5N1 influenza virus. For calculation purposes, an undetectable level was scored as a titer equal to one. Individual titer (points) and geomean (lines) was given for each group. Asterisks indicate a statistically significant difference ($p<0.05$).

FIG. 11 shows construction of baculovirus expression vector for influenza VLP production. Influenza VLPs are obtained from Sf9 cells that are infected with (A) a single baculovirus that encodes two viral proteins (BacHA-M1) (B) two baculoviruses that encode three viral proteins (BacHA-M1 and BacNA) (C) two baculoviruses that encode four viral proteins (BacHA-M1 and BacNA-M2). pH: polyhedron promoter; p10: p10 promoter.

SUMMARY OF THE INVENTION

Figure 1:
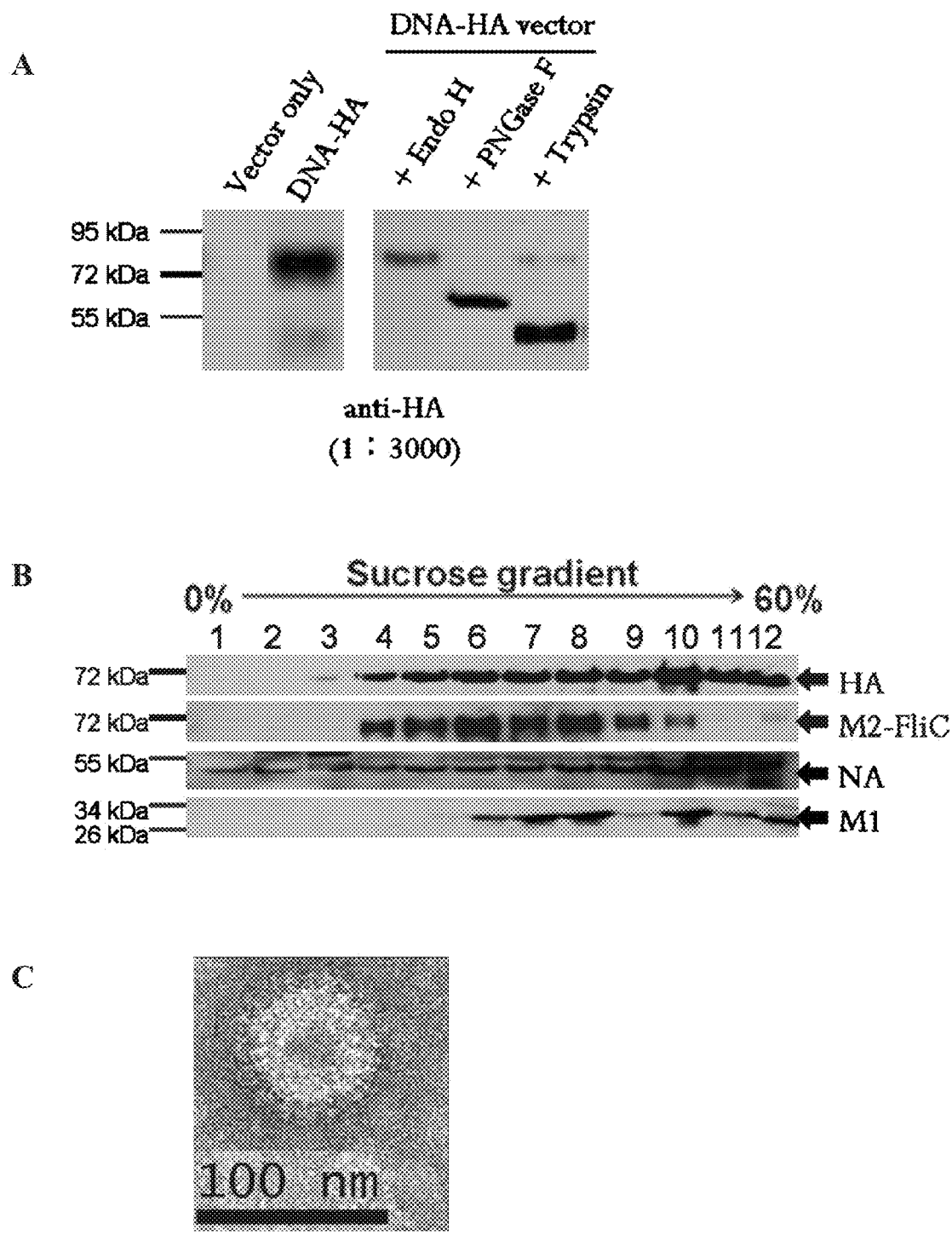
FIG. 1 shows expression and characterization of DNA-HA and FliC-VLP. (A) The cell lysates of 293A cells transfected with either DNA-HA or empty vector were treated with Endo H, PNGase F and Trypsin, and analyzed by Western blots. Full-length HA proteins showed the presence of a molecular weight of approximately 75 kDa and HA1 proteins showed the presence of a molecular weight of about 46 kDa. (B) FliC-VLPs were purified by sucrose gradient sedimentation and the results showed the fractions 6 to 10 from the sucrose density gradient contained all four proteins. (C) Electron microscopic visualization demonstrated the spherical morphology of the FliC-VLPs with a particle size around 100 nm.

The present invention relates to a DNA vaccine comprising hyperglycosylated HA gene(s), which is derived from avian influenza virus, wherein the mutant HA gene encodes a protein having a mutation at amino acid residue selecting from the group consisting of 83, 86, 94, 127, 138, 161, 182, and 252. The present invention also relates to a DNA vaccine composition comprising: (a) an above-mentioned DNA vaccine; and (b) a booster. The present invention further relates to an influenza VLP comprising adjuvant-fused M2 protein.

DETAILED DESCRIPTION OF THE INVENTION

As used herein, the term "wild-type" refers to a naturally occurring organism. The term also relates to nucleic acids and proteins found in a naturally occurring organism of a naturally occurring population arising from natural processes, such as seen in polymorphisms arising from natural mutation and maintained by genetic drift, natural selection and so on, and does not include a nucleic acid or protein with a sequence obtained by, for example, recombinant means.

"Immunogen" and "antigen" are used interchangeably herein as a molecule that elicits a specific immune response of antibody (humoral-mediated) and/or T cell origin (cell-mediated), for example, containing an antibody that binds to that molecule or a $CD4^+$ or $CD8^+$ T cell that recognizes a virally-infected cell expressing that molecule. That molecule can contain one or more sites to which a specific antibody or T cell binds. As known in the art, such sites are known as epitopes or determinants. An antigen can be polypeptide, polynucleotide, polysaccharide, a lipid and so on, as well as a combination thereof, such as a glycoprotein or a lipoprotein. An immunogenic compound or product, or an antigenic compound or product is one which elicits a specific immune response, which can be humoral, cellular or both.

An "individual" or "subject" or "animal", as used herein, refers to vertebrates that support a negative strand RNA virus infection, specifically influenza virus infection, including, but not limited to, birds (such as water fowl and chickens) and members of the mammalian species, such as canine, feline, lupine, mustela, rodent (racine, and murine, etc.), equine, bovine, ovine, caprine, porcine species, and primates, the latter including humans.

As used herein, the term "a plurality of" is employed to describe the number of elements and components of the present invention. This description should be read to more than one unless it is obvious that it is meant otherwise.

As used herein, the term "a" or "an" is employed to describe elements and components of the invention. This is done merely for convenience and to give a general sense of the invention. This description should be read to include one or at least one and the singular also includes the plural unless it is obvious that it is meant otherwise.

As used herein, the term "or" is employed to describe "and/or".

Accordingly, the present invention provides a DNA vaccine comprising hyperglycosylated HA gene(s), which is derived from avian influenza virus, wherein the mutant HA gene encodes a protein having one or more mutations at amino acid residue selecting from the group consisting of 83, 86, 94, 127, 138, 161, 182, 252, and the combination thereof.

In one embodiment, the hyperglycosylated HA gene encodes a protein comprising an amino acid sequence selected from the group consisting of SEQ ID NOs: 4, 6, 8, 10, 12, 14, 16, 18, and 20. In another embodiment, the mutant HA gene encodes a protein comprising an amino acid sequence of SEQ ID NOs: 4, 6, or 10.

In one embodiment, delivery of the DNA vaccine into a subject elicits an immune response against a plurality of avian influenza virus subtypes in the subject. In another embodiment, the delivery is achieved by way of, for example but not limited to, subcutaneous injection, intramuscular injection, oral administration, spraying or gene gun injection.

The present invention also provides a DNA vaccine composition comprising: (a) an above-mentioned DNA vaccine; and (b) a booster.

In one embodiment, the booster is an influenza VLP. In another embodiment, the influenza VLP is derived from cell infected by recombinant baculoviruses comprise one or more plasmids containing HA gene, M1 gene, NA gene and FliC-M2 gene, which encodes FliC-M2 fusion protein.

In one embodiment, the DNA vaccine composition further comprises an adjuvant. In another embodiment, the adjuvant is an aluminum-containing adjuvant.

In one embodiment, the DNA vaccine and the booster have a mass ratio in the range of 1:2 to 17:6. In another embodiment, the DNA vaccine and the booster have a mass ratio in the range of 5:6 to 5:2. In still another embodiment, the DNA vaccine and the booster have a mass ratio of 5 to 3.

In one embodiment, delivery of the DNA vaccine composition into a subject elicits an immune response against a plurality of avian influenza virus subtypes in the subject. In another embodiment, the delivery is achieved by way of, for example but not limited to, subcutaneous injection, intramuscular injection, oral administration, spraying or gene gun injection.

The present invention further provides an influenza VLP comprising adjuvant-fused M2 protein. In one embodiment, the influenza VLP further comprises HA protein, NA protein and M1 protein. In another embodiment, the adjuvant is flagellin (FliC) or profiling (PRO).

The next examples provide some exemplary embodiments of the present invention as follows:

EXAMPLES

The examples below are non-limiting and are merely representative of various aspects and features of the present invention.

Example 1

Material and Methods

Construction of DNA-HA Vaccine Vector

The cDNA of the HA gene of influenza virus A/Thailand/1(KAN-1)/2004/H5N1 (clade 1), SEQ ID NO: 1, was provided by Prasert Auewarakul, Siriraj Hospital, Thailand. The full-length HA sequence was inserted into a pcDNA™3.1(+) vector (Invitrogen) using KpnI/NotI cut site. The constructed plasmid containing H5HA was transfected into 293A cells by using Turbofect reagent (Fermentas). Following transfection for 48 hours, the cell lysates were collected by centrifugation at 5000 rpm for 10 minutes and HA expression was analyzed by Western blotting with anti-H5HA antibodies (ab21297; Abcam).

HA Glycosylation Pattern and Trypsin Treatment

For characterizing the HA glycosylation pattern, 293A cells were harvested after transfected with DNA-HA vectors for 48 hours. The cell lysates were treated with EndoH or PNGase F for 2 hours at 37° C., and the H5HA glycosylation pattern was determined by Western blotting. For trypsin treatment, the cell lysates were incubated with trypsin for 30 minutes on ice, and the cleavage of HA0 into HA1 and HA2 was observed by Western blotting.

Preparation of VLPs

VLPs were prepared as described previously (Wei H J et al., Vaccine 29 (2011): 7163-7172). Briefly, HA (SEQ ID NO: 1) and M1 (SEQ ID NO: 21) were cloned into a pFastBac™ Dual vector (Invitrogen), while NA (SEQ ID NO: 27) and FliC-M2 (SEQ ID NO: 25), expressing FliC-M2 fusion proteins, were cloned into the other one to produce the recombinant baculoviruses. Sf9 cells co-infected with recombinant baculoviruses were harvested at 72 hours post-infection, and supernatants containing FliC-VLPs were concentrated by filtration with a 500 kDa filter membrane. The concentrate were loaded on 0-60% sucrose gradients and centrifuged for 4 hours at 33,000 rpm. The desired particles were observed by Western blotting using anti-H5HA antibodies (ab21297; Abcam), anti-NA antibodies (ab70759; Abcam), anti-M1 antibodies (ab25918; Abcam), and anti-M2 antibodies (NB100-2073; Novus). The particles were also confirmed by transmission electron microscopy (TEM) as described previously (Wei H J et al., Vaccine 29 (2011): 7163-7172).

Preparation of Hyperglycosylated H5HA

Mutations were introduced into the HA gene by using the site-directed mutagenesis, and plasmids encoding wild-type H5HA gene (SEQ ID NO: 1) were used as templates. The 50 µL PCR reaction was carried out with 100 ng templates, 2 mM primer pair, 200 mM dNTPs and 2 U of DNA polymerase. The PCR products were purified and further treated with DpnI for 2 hours at 37° C. DpnI treated products were transformed into TOP10 competent cell and then the mutated plasmids were isolated.

Hemadsorption Assay 293A cells were transfected with wild-type and mutated H5HA DNA vectors, and the cells were harvested at 72 hours post infection. Following phosphate-buffered saline (PBS)

wash, sufficient 0.5% turkey red blood cells (RBCs) were added to cover cell monolayer and incubate for 30 minutes. Adsorption of RBCs on the transfected cells was observed after rinse with PBS two times.

Mouse Immunization 6 to 8 weeks old female BALB/c mice were immunized with heterologous prime-boost strategy by 50 μg of DNA and 30 μg of purified VLPs mixed with Alum adjuvant in PBS. Immunizations were performed at weeks 0, 3 by intramuscular injection. Blood was collected at 14 days following immunization, and serum was isolated. Serum samples were inactivated at 56° C. for 30 minutes and stored in −20° C. All experiments were conducted in accordance with the guidelines of the Laboratory Animal Center of National Tsing Hua University (NTHU). Animal use protocols were reviewed and approved by the NTHU Institutional Animal Care and Use Committee (approval no. 09733).

Enzyme-Linked Immunosorbent (ELISA) Assay

ELISA assay was performed as described previously (Lin S C et al., PLoS One 6 (2011): e20052). Briefly, 2 μg/mL of purified protein were coated on 96 well plates and then blocked with BSA. Serial dilutions of each serum sample were incubated in the plates for 1 hour and removed by 3 times wash. Goat anti-mouse IgG conjugated HRP (Bethyl Laboratories, Inc.) was incubated in the plates for 1 hour followed by 3 times wash. After the reaction with TMB substrate stop, plates were read at 450 nm absorbance. End-point titer was determined as the reciprocal of the final dilution giving an optical of two-fold absorbance of negative control.

Hemagglutinin Inhibition (HI) and Neutralization (NT) Assays

HI and NT assays were performed as described previously (Huang M H et al., PLoS One 5 (2010): e12279). For HI assay, serum samples (two-fold dilutions starting with an initial dilution of 1:10) were incubated with four HA units of influenza strain. Turkey RBCs were then added and the inhibition of agglutination was scored. The serum titer was expressed as the reciprocal of the highest dilution that showed complete inhibition of HA. For NT assay, the 200 $TCID_{50}$ per well of virus were incubated with two-fold-diluted mice sera at a starting dilution of 1:40. Mixtures of virus and serum were transferred to monolayers of MDCK cells and incubated for 4 days. The neutralizing titer was defined as the reciprocal of the highest serum dilution at which the infectivity of the H5N1 virus was neutralized in 50% of the wells. Infectivity was identified by the presence of cytopathy on Day 4 and the titer was calculated using the Reed-Muench method.

Statistic Analysis

All results were analyzed using two-tailed Student's t tests, with a P value of <0.05 indicating statistical significance Results Construction and Characterization of DNA-HA Vaccine Vector and FliC-VLPs for Prime-Boost Immunization The DNA vaccine vector (DNA-HA) encoding the full-length cDNA of the A/Thailand/1 (KAN-1)/2004/H5N1 (clade 1) HA gene (SEQ ID NO: 1) was constructed from the pcDNA™3.1(+) vector. Expression of the full-length HA protein was demonstrated in 293A cells transfected with the DNA-HA vector and analyzed in Western blots to show the presence of a molecular weight of approximately 75 kDa (FIG. 1A). The expressed HA in 293A cells was sensitive to PNGase F treatment but resistant to EndoH digestion, suggesting as a glycoprotein containing complex type N-linked glycan profiling (FIG. 1A). The expressed HA in DNA-HA transfected 293A cells was also sensitive to trypsin treatment by cleavage from HA0 to HA1 and HA2 subunits, as shown the presence of HA1 at a molecular weight about 46 kDa (FIG. 1A).

The FliC-containing VLPs (FliC-VLPs) were obtained from Sf9 cells infected with two recombinant baculoviruses encoding four of the influenza virus genes of HA, NA, and M1, and the fusion of M2 and the *Samollena* fliC genes (Wei H J et al., Vaccine 29 (2011): 7163-7172). FliC-VLPs were obtained from the culture supernatants of baculovirus-infected Sf9 cells, purified by ultracentrifugation and sucrose gradient sedimentation. The results show the fractions 6 to 10 from the sucrose density gradient contained all four viral or fusion proteins (FIG. 1B). Electron microscopic visualization demonstrated the spherical morphology of the FliC-VLPs with a particle size around 100 nm (FIG. 1C).

Figure 2:
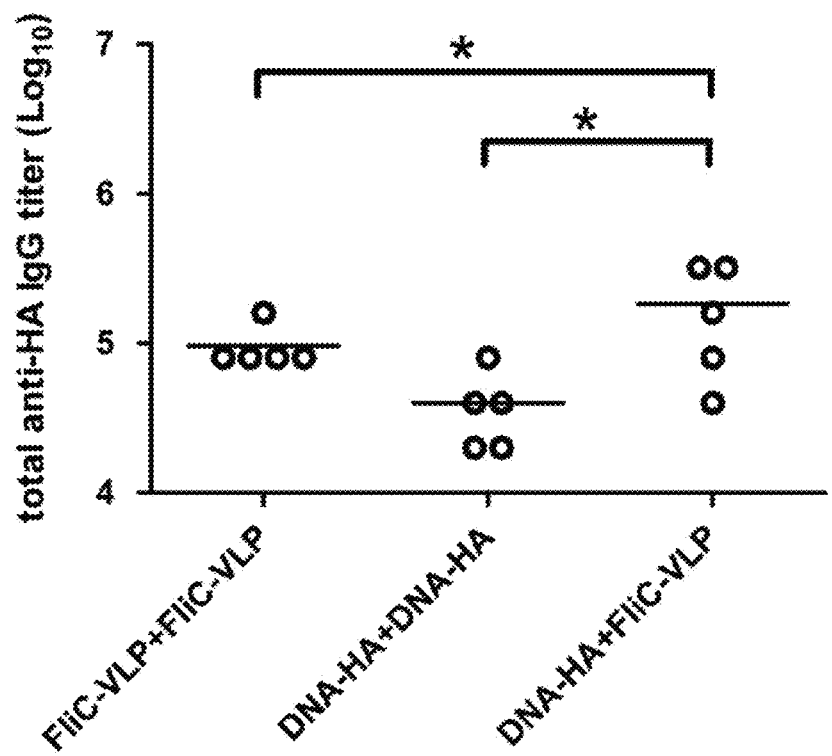
FIG. 2 shows total anti-HA IgG titers elicited by DNA-HA and FliC-VLP. Asterisks indicate a statistically significant difference ($p<0.05$).
Figure 3:
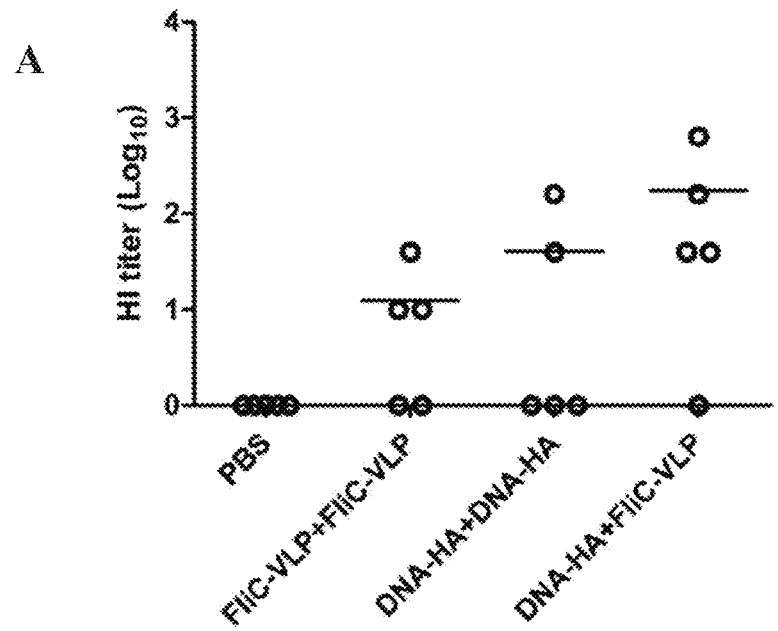
FIG. 3 shows neutralizing activities of the sera from immunized mice by the (A) HI and (B) NT titers against the NIBRG-14 (clade 1) H5N1 influenza virus. For calculation purposes, an undetectable level was scored as a titer equal to one. Individual titer (points) and geomean (lines) was given for each group.
Figure 3:
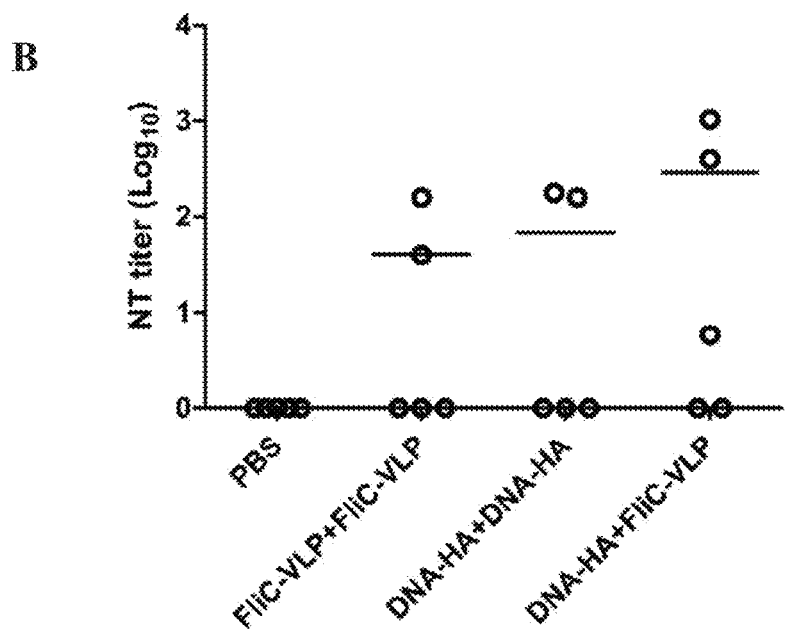

To investigate the combined use of DNA-HA vaccine vector and FliC-VLP for prime-boost immunization studies, BALB/c mice were immunized intramuscularly (i.m) for two doses within a three-week interval as the following prime-boost regimens: (i) PBS+PBS (ii) FliC-VLP+FliC-VLP (iii) DNA-HA+DNA-HA (iv) DNA-HA+FliC-VLP. Sera were collected at two weeks after the second dose in immunized mice. The results show that the HA-specific total IgG titer by DNA-HA vaccine vector priming, followed by FliC-VLP boosting was significantly higher than two-dose immunization using DNA-HA vector and FliC-VLPs (FIG. 2). Neutralizing activities revealed by measuring the HI and NT titers against the NIBRG-14 (clade 1) H5N1 influenza virus show that the DNA-HA vector priming and FliC-VLP boosting regiment elicited the highest magnitude of neutralizing antibodies in mice (FIGS. 3A-B).

Figure 4:
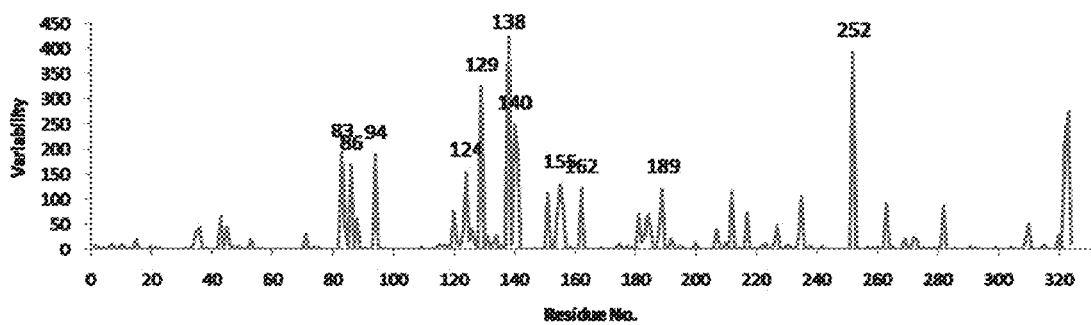
FIG. 4 shows analytical result of amino acid variation in the HA of 163 avian influenza virus strains. Eleven amino acids in the HA1 subunit, including the 83, 86, 94, 124, 129, 138, 140, 155, 162, 189 and 252 residues were calculated to have relatively higher scoring numbers.

Design of Hyperglycosylated HA Based on Amino Acid Sequences of H5N1 Human Isolates To design the hyperglycosyalted HA DNA vaccines, sequence alignment analysis was first conducted from 163 HPAI H5N1 human isolates (sequences retrieved from NCBI Database). The amino acid differences in these HA1 protein sequences were analyzed based on the following scoring numbers, 4 (different amino acid), 2 (weak similar amino acid), 1 (strong similar amino acid), 0 (identical amino acid) as characterized by the Vector NTI Similar Tables. According to the alignment plot shown in FIG. 4, eleven amino acid residues in the HA1 protein were identified to have a relatively higher scoring numbers, including the 83, 86, 94, 124, 129, 138, 140, 155, 162, 189, and 252 residue. To design the antibody-refocused immunogens, site-directed mutagenesis is conducted in each of the five regions with mutations to allow the addition of the N—X—S/T motif (for N-linked glycosylation site) but avoid the receptor binding sites (Yang Z Y et al., Science 317 (2007): 825-828; and Yang H et al., PLoS Pathog 6 (2010): e1001081).

Figure 5:
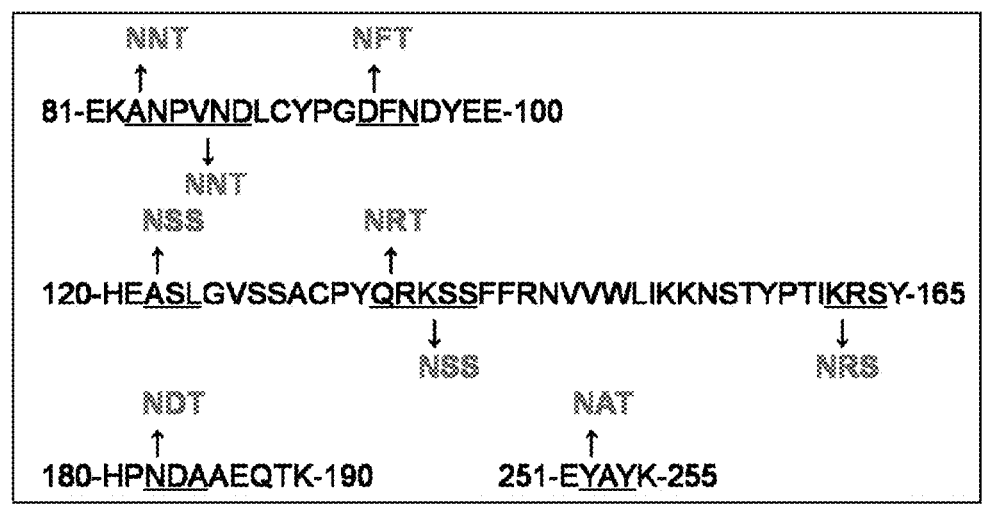
FIG. 5 shows nine N-linked glycosylation sites: 83NNT (SEQ ID NO:4), 86NNT (SEQ ID NO:6), 94NFT (SEQ ID NO:8), 127NSS (SEQ ID NO:10), 138NRT (SEQ ID NO:12), 140NSS (SEQ ID NO:14), 161NRS (SEQ ID NO:16), 182NDT (SEQ ID NO:18), and 252NAT (SEQ ID NO:20). Underlined triplet amino acids and arrows point away from wild-type sequence to amino acid change that resulted in N-linked glycosylation sequence.
Figure 6:
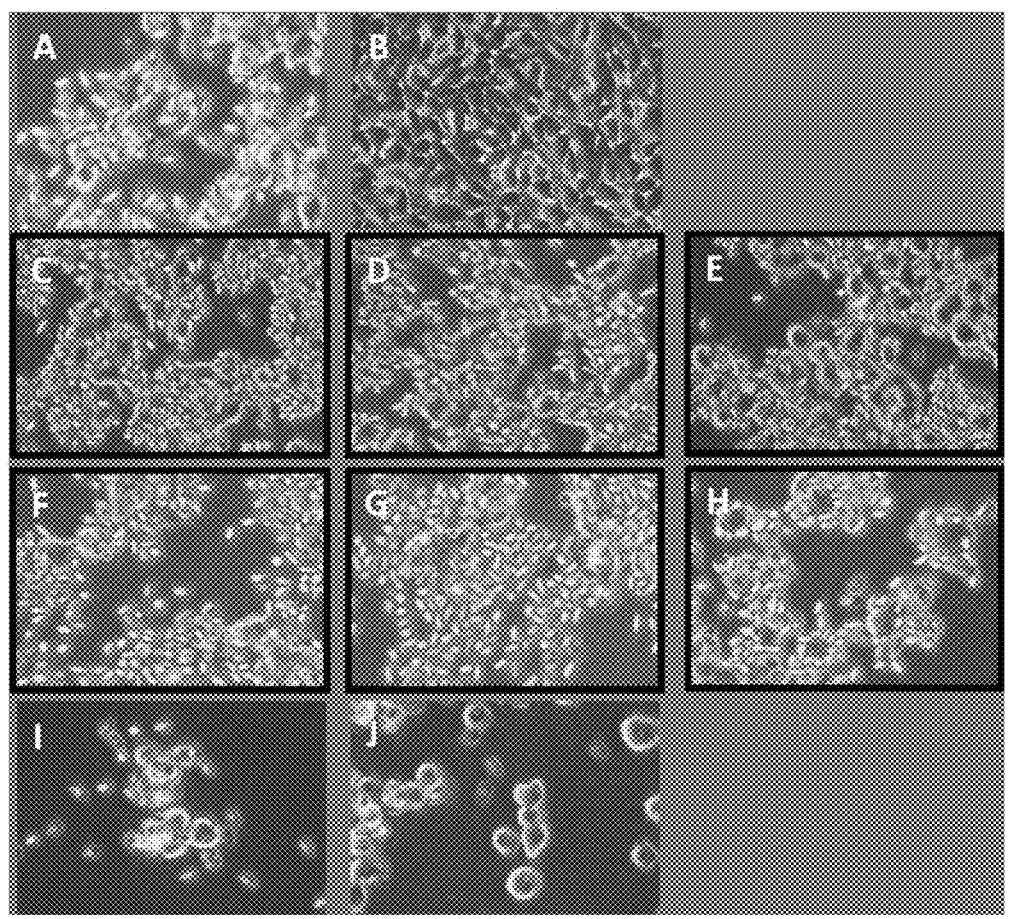
FIG. 6 shows the results of hemadsorption assay. (A) Positive control; (B) negative control; (C) 83NNT; (D) 86NNT; (E) 94NFT; (F) 127NSS; (G) 138NRT; (H) 161NRS; (I) 182NDT; and (J) 252NAT.
Figure 7:
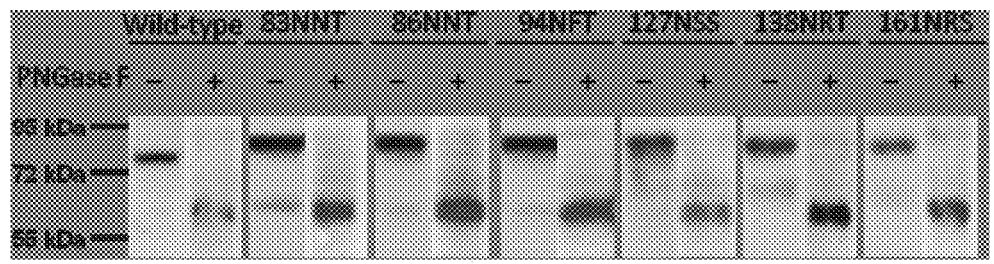
FIG. 7 shows characterization of hyperglycosylated HA. The six HA mutant proteins (83NNT, 86NNT, 94NFT, 127NSS, 138NRT, 161NRS) with N-linked glycans addition were illustrated by the increased molecular weights and reduced to the same molecular weight after PNGase F treatment.

Nine N-X-S/T motifs were thus introduced into HA1, including 83NNT (99-101 of the SEQ ID NO: 4), 86NNT (102-104 of the SEQ ID NO: 6), 94NFT (110-112 of the SEQ ID NO: 8), 127NSS (143-145 of the SEQ ID NO: 10), 138NRT (154-156 of the SEQ ID NO: 12), 140NSS (156-158 of the SEQ ID NO:14), 161NRS (177-179 of the SEQ ID NO: 16), 182NDT (198-200 of the SEQ ID NO: 18), and 252 NAT (268-270 of the SEQ ID NO: 20) (FIG. 5), wherein 83NNT, 86NNT, 94NFT, 127NSS, 138NRT, 140NSS, 161NRS, 182NDT and 252NAT are amino sequences of the mature protein whereas SEQ ID NOs: 4, 6, 8, 10, 12, 14, 16, 18, and 20 are amino sequences of the immature protein. Each of the refocusing hyperglycosylated HA genes containing the specified N-linked glycosylation sites were cloned into the DNA-HA vaccine vector. However, only six out the nine immuno-focusing HA retained the hemagglutination property for Turkey red blood cells after transfection into 293A cells (FIG. 6). The six HA mutant genes (83NNT, 86NNT, 94NFT, 127NSS, 138NRT and 161NRS) were also investigated for the introduction of N-linked glycans in the HA antigens as illustrated by the increased molecular weights and reduced to the same molecular weight after PNGase F treatment (FIG. 7).

Priming with Hyperglycosylated HA DNA Vaccines Followed by FliC-VLP Boosting

Figure 8:
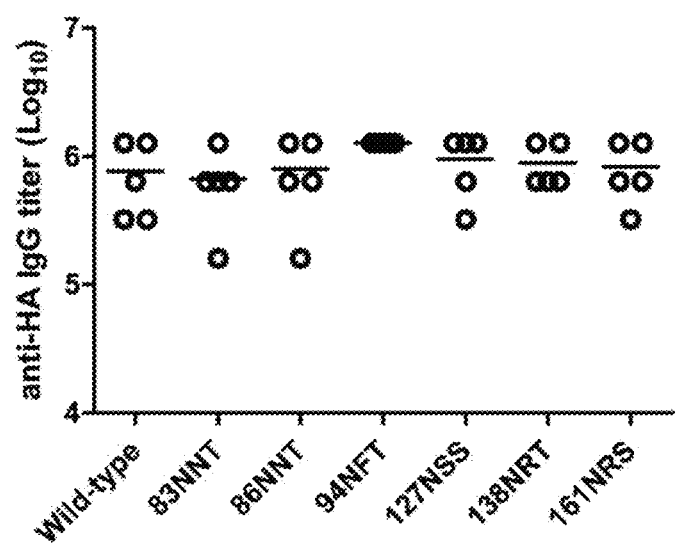
FIG. 8 shows total anti-HA IgG titers elicited by hyperglycosylated HA. Individual titer (points) and geomean (lines) was given for each group.
Figure 9:
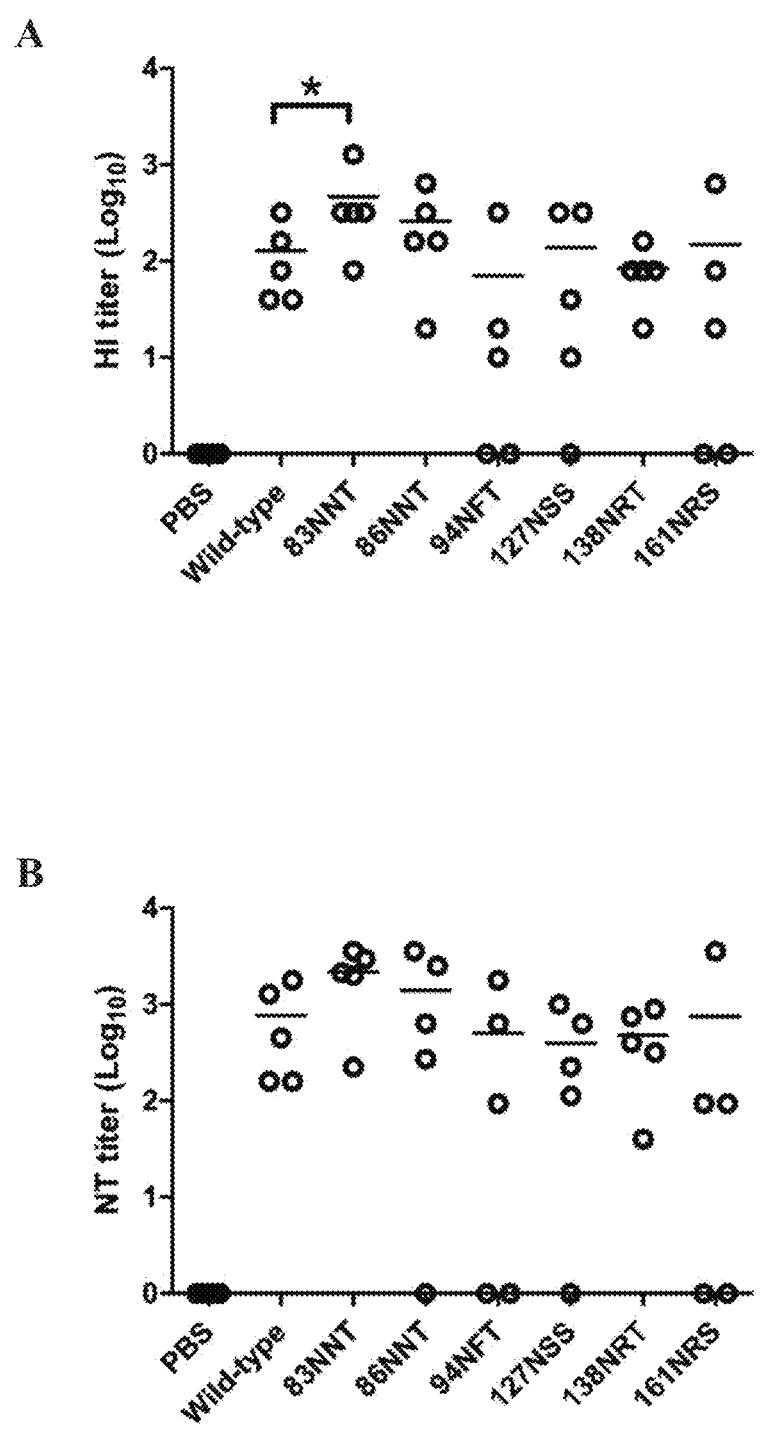
Figure 10:
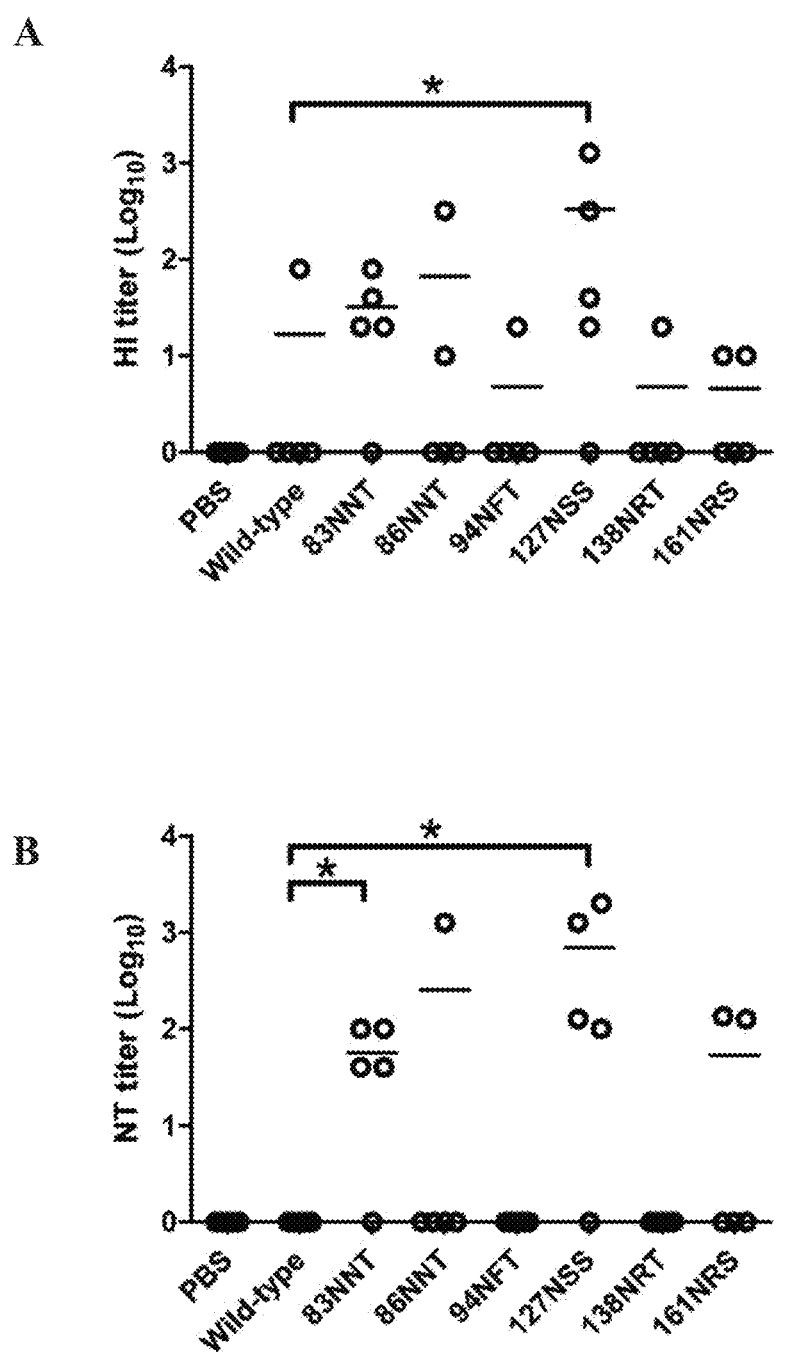
Figure 12:
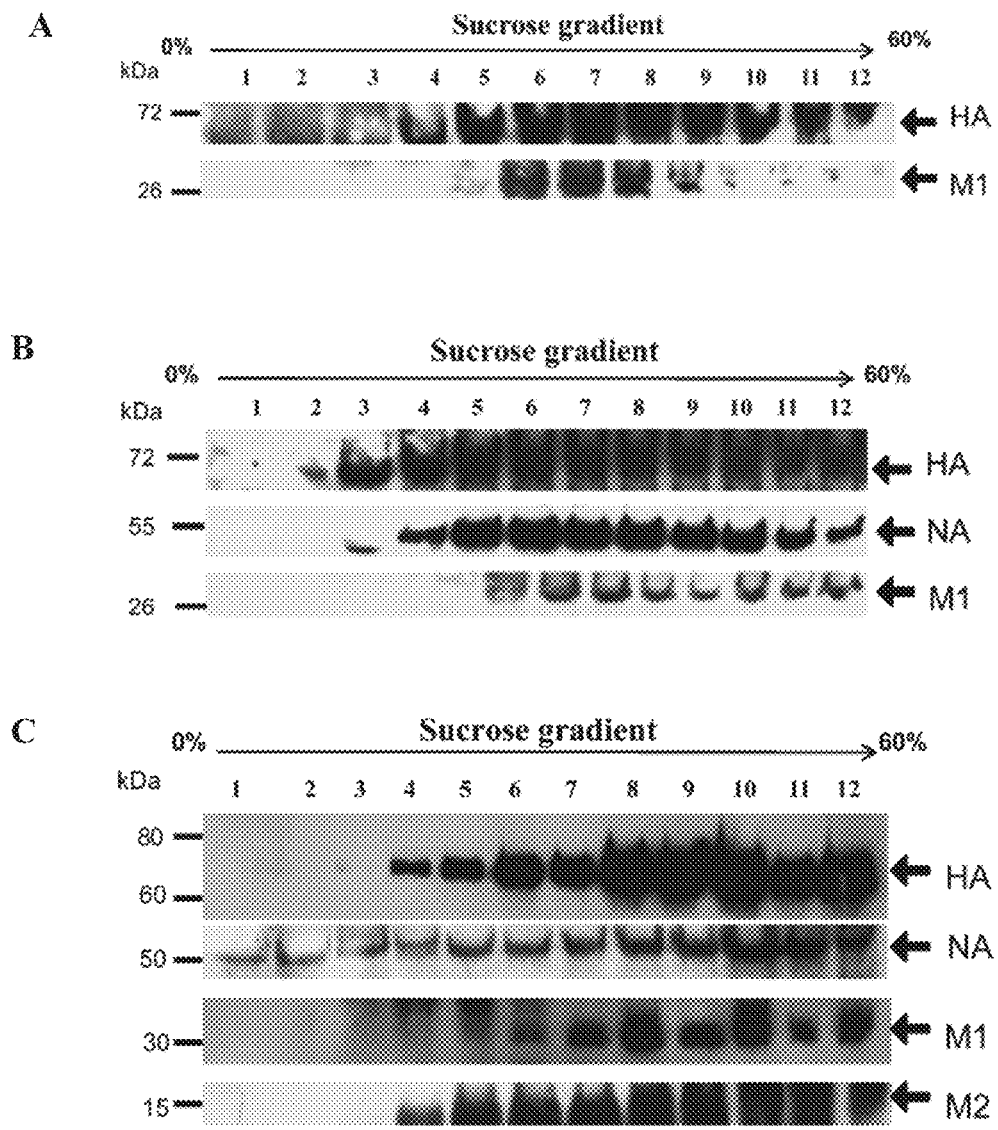
FIG. 12 shows sucrose gradient analyses of the influenza VLPs obtained by the expression by baculovirus of (A) two viral proteins (HA and M1); (B) three viral proteins (HA, NA, M1); and (C) four viral proteins (HA, NA, M1, M2). Purified sucrose fractions were resolved in SDS-PAGE gels and reacted with anti-HA, anti-M1, anti-NA, and anti-M2 antibodies.
Figure 13:
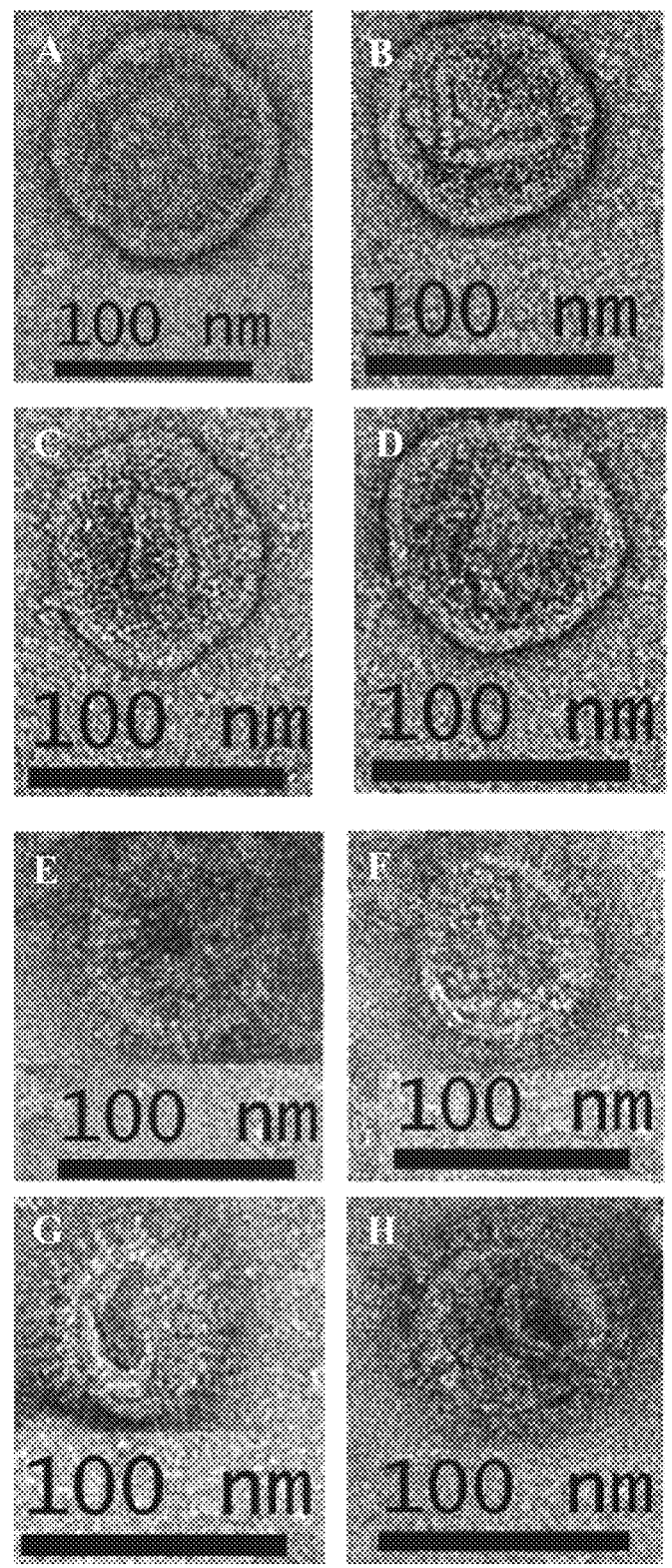
FIG. 13 shows TEM analyses of influenza VLPs expressed by baculovirus using (A-D) two viral proteins (HA and M1); (E-H) three viral proteins (HA, NA, M1); and (1-L) four viral proteins (HA, NA, M1, M2). The TEM images present quadruple samples for each case of negative staining of influenza VLPs with uranyl acetate.
Figure 13:
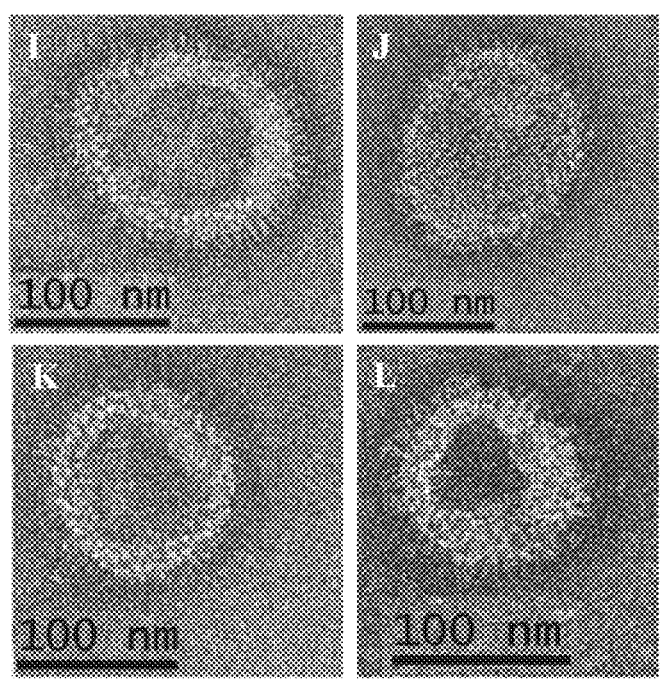
Figure 14:
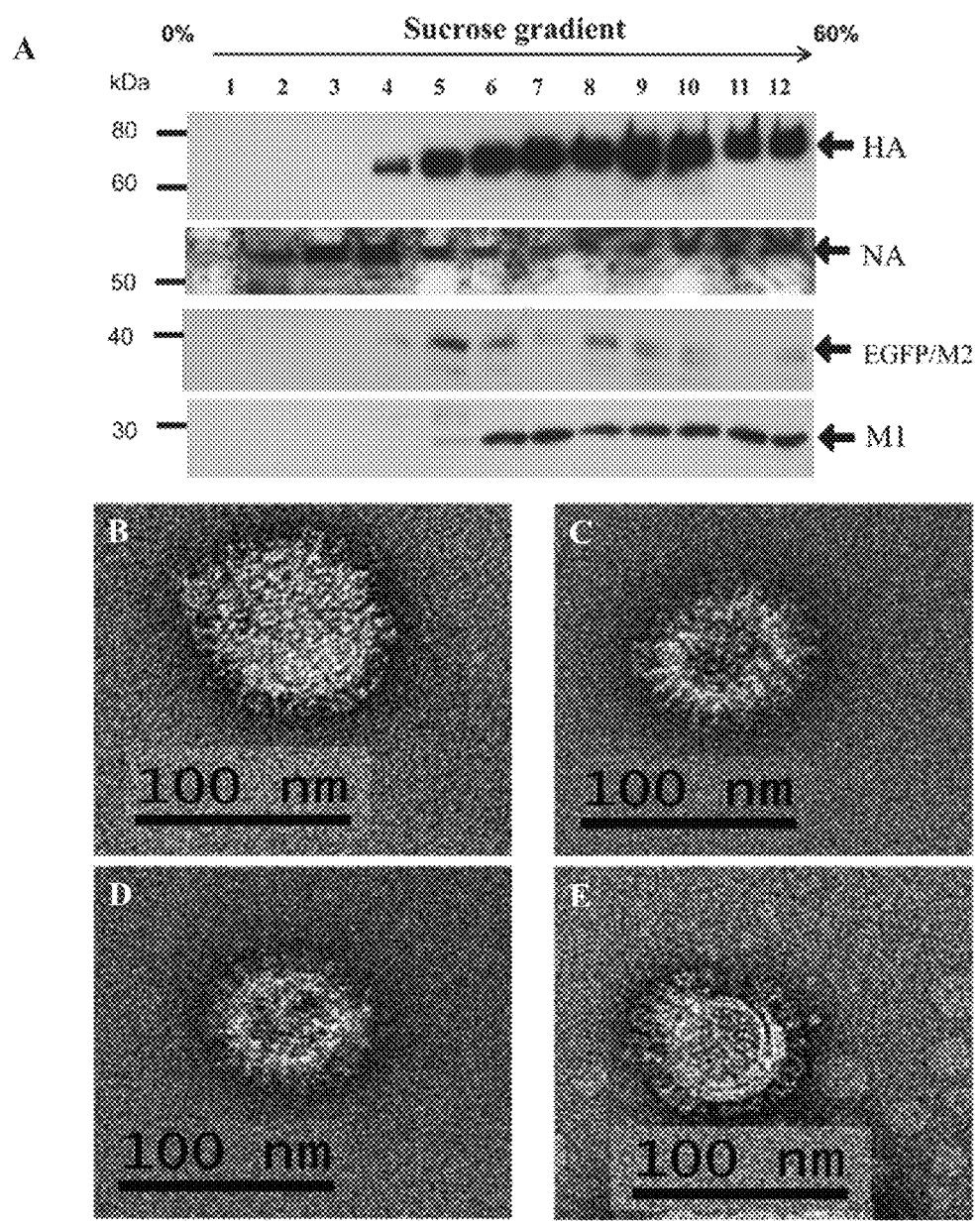
FIG. 14 shows production of influenza VLPs with EGFP/M2 fusion protein. (A) Sucrose gradient analysis of influenza VLPs, reacted with anti-HA, anti-NA, anti-M1, anti-EGFP specific antibodies; (B-E) TEM images of influenza EGFP-VLPs that are negatively stained with uranyl acetate, showing quadruple samples.

To investigate the antibody responses elicited by these six hyperglycosylated HA mutants (83NNT, 86NNT, 94NFT, 127NSS, 138NRT and 161NRS), mice were immunized with each DNA-HA vector twice followed with a third boosting dose with FliC-VLPs on a three-week interval. The results show that no significant differences of the HA-specific total IgG titers of all the immunized groups with the hyperglycosyalted HA DNA vaccines compared to the wild-type control (FIG. 8). The 83NNT and 86NNT HA mutants elicited higher HI titers (FIG. 9A) but only the 83NNT HA mutant had higher NT titer (FIG. 9B) against the NIBRG-14 virus that belongs to the same H5N1 clade 1 strain. The HI and NT titers of these sera against the Mongolia/2/2006 H5N1 virus of the clade 2.2 strain were also measured. The data presenting as cross-clade functional antibodies show that the 83NNT, 86NNT, 127NSS HA mutants elicited higher HI titers (FIG. 10A) and the 83NNT, 86NNT, 127NSS, 161 NRS HA mutants had higher NT titers (FIG. 10B). Taken together, the 83NNT mutant can elicit more potent HI and NT titers against both the NIBRG-14 (clade 1) and Mongolia/2/2006 (clade 2.2) HPAI H5N1 viruses.

Example 2

Methods and Materials

Cell Lines

Sf9 cells (ATCC CRL-1711) (Invitrogen) were derived from pupal ovarian tissue of the fall armyworm, *Spodoptera frugiperda*. Sf9 cells were maintained in T-flasks at 28° C. with SF-900II serum free medium (GIBCO) that contained 100 units/mL penicillin and 100 μg/mL streptomycin (Invitrogen). For suspension cultures, Sf9 cells were inoculated in 500 mL spinner flasks (Belleco) at 60 rpm at 27° C. with 300 mL of the same medium. A549 cells (human lung carcinoma cells) (ATCC CCL-185) were maintained in T-flasks at 37° C. with DMEM (GIBCO) that contained 5% fetal bovine serum (FBS), 100 units/mL penicillin, and 100 μg/mL streptomycin (Invitrogen).

Mouse Bone Marrow-Derived DCs

C57BL/6 mice were used at 10-14 weeks of age and their bone marrow cells were isolated from femurs and tibias and seeded on Costar 24-well cell culture plates in 1 mL of RPMI 1640 medium that was also supplemented with 10% heat-inactivated FBS, 2 mM 1-glutamine, nonessential amino acids, sodium pyruvate, HEPES (all from GIBCO), $5.5 \times 10^{-2}$M 2-ME (Sigma-Aldrich), 100 units/mL penicillin, 100 μg/mL streptomycin (Invitrogen) and 15 ng/mL recombinant mouse GM-CSF (PeproTech). On Day 3, 1 mL of medium that contained 10 ng/mL of GM-CSF was added to plates. On Day 5, another 0.5 mL fresh medium that contained 10 ng/mL of GM-CSF was added. The 6- to 7-day-culture BMDCs (>80% CD11c+ cells) were used. All experiments were conducted in accordance with the guidelines of Laboratory Animal Center of National Tsing Hua University (NTHU). The animal use protocols have been reviewed and approved by the NTHU Institutional Animal Care and Use Committee (Approved protocol no. 09733).

Plasmid Construction

The HA gene of A/Thailand/1(KAN-1)/2004/H5N1 (SEQ ID NO: 1) was provided by Dr. Prasert Auewarakul, Siriraj Hospital, Mahidol University, Thailand. The NA gene of A/Viet Nam/1203/2004/H5N1 (SEQ ID NO: 27) was obtained from Academia Sinica, Taiwan. The M1 (SEQ ID NO: 21) and M2 (SEQ ID NO: 23) genes of A/WSN/33/H1N1 were obtained from virus stocks using reverse transcription-PCR. The genes of HA (A/Anhui/1/2005/H5N1), enhanced florescence protein (EGFP), flagellin (FliC), and profilin (PRO) were purchased from synthesized sequences (Mr. Gene) based on the NCBI GenBank accession numbers GU983383.1, AY649721.1 and AY937257.1, respectively. Each gene fragment was subcloned into pFastbac Dual (Invitrogen) using BamHI/NotI site for HA, XhoI/KpnI site for M1, EcoRI/HindIII site for M2, XhoI/KpnI site for NA, EcoRI/HindIII site for EGFP/M2 fusion, EcoRI/HindIII site for FliC/M2 fusion, and EcoRI/HindIII site for PRO/M2 fusion. These inserted vectors were then transformed into *E. coli* strain DH5a and selected by ampicillin. All the inserted sequences were confirmed by DNA sequence analysis (Mission Biotech Inc., Taipei, Taiwan).

Generation of Recombinant Baculoviruses

The pFastbac Dual plasmids encoding each specified gene(s) were transformed into *E. coli* strain DH10Bac (Invitrogen) and selected on an LB plate that contained kanamycin (Invitrogen), gentamicin (Invitrogen), tetracycline (Invitrogen), Bluo-gal (Invitrogen), and IPTG (BioRad). The selected colonies or the recombinant bacmids were confirmed by PCR using M13 primers, then transfected into Sf9 cells using Cellfectin (Invitrogen). After 4 days, the recombinant baculoviruses were collected from culture supernatants and the virus titers were determined using an ID50 software.

Production and Purification of Influenza VLPs

The VLPs that were expressed by two viral proteins and Sf9 cells were infected with BacHA-M1 recombinant baculovirus at an MOI of 1. The VLPs that were expressed by three viral proteins were co-infected with BacHA-M1 and Bac-NA recombinant baculoviruses at an MOI of 3 and 1, respectively. The VLPs that were expressed by four viral proteins including M2 fusion proteins were co-infected with BacHA-M1 and BacM2-NA (or BacEGFP/M2-NA, BacNA-M2/FliC, BacNA-M2/PRO) recombinant baculoviruses at an MOI of 3 and 1, respectively. At 72 hours post infection, the culture supernatants were harvested and clarified by centrifugation for 0.5 hour at 12,000 rpm at 4° C. Then, they were concentrated and pelleted for 2 hours at 33,000 rpm and 4° C. using a Hitachi RPS40ST rotor. The particles were resuspended in 0.8 mL of PBS buffer, and loaded on a 0-60% (w/v) discontinuous sucrose gradient, before being ultracentrifuged by a Hitachi RPS40ST rotor 4 hours at 33,000 rpm and 4° C. Following ultracentrifugation, the fractions (0.8 mL) were collected and the samples in each fraction were analyzed by SDS-PAGE and Western blotting.

Hemagglutination Titer

For the hemagglutination titer test, a series of two-fold dilutions of influenza VLPs in PBS were prepared and incubated at 25° C. for 40 min with 50 μL of 0.5% Turkey red blood cells. The extent of hemagglutination was observed visually, and the highest dilution that can agglutinate red blood cells was determined.

Sodium Dodecyl Sulfate Polyacrylamide Gel Electrophoresis (SDS-PAGE) and Western Blotting Each sucrose gradient fraction sample was treated with 1×SDS gel-loading buffer (50 mM Tris-HCl, 100 mM dithiothreitol, 2% SDS, 0.1% bromophenol blue, and 10% glycerol) for 5 min, resolved on 12% SDS-PAGE, and then transferred to PVDF membranes. Following the transfer, the PVDF membranes were blocked using 10% milk on an orbital shaker for 1 hour. Then the membranes were first reacted with anti-HA (Abcam ab21297), anti-M1 (Abcam ab25918), anti-NA (Abcam ab70759), anti-M2 (novus NB100-2073) or anti-EGFP (novus NB-600-601ss) antibodies for 1 hour, then reacted with the goat anti-rabbit or goat anti-mouse IgG conjugated with HRP (horse radish peroxidase) for 1 hour. Enhanced chemiluminescence (ECL) was detected through binding to HRP and visualized on a Fuji Medical X-ray film using a Western blot detection system (Amersham Bioscience).

Transmission Electron Microscopy (TEM)

The purified sucrose fractions containing VLPs were pooled and ultracentrifugated using the Hitachi RPS40ST rotor 2 hours at 33,000 rpm and 4° C. to remove the sucrose and to pellet the VLPs. The VLP pellets were resuspended with 200 µL PBS. For deep staining of the grid, 3 µL purified VLPs was added to the carbon-coated copper grid and stained three times with uranyl acetate before being vacuum-dried overnight.

Confocal Fluorescence Microscopy

A549 cells were grown on glass coverslips. VLPs were labeled with DiI (Vybrant DiI cell labeling solution) and A549 cells were labeled with DiD (Vybrant DiD cell labeling solution). Labeled VLPs were incubated with labeled A549 cells and analyzed by confocal fluorescence microscopy. DiI was excited by the 561 nm line of a laser. DiD was excited by the 633 nm line of a laser. EGFP was excited by the 488 nm line of a laser.

Mouse Immunization

A group of five female BALB/c mice (6 to 8 weeks old) was used for immunization studies. Immunizations were performed by intramuscular injection of 15 µg of the purified VLPs (suspended in PBS at pH 7.4) for each dose and three doses were conduced in a 3-week interval. Blood was collected 2 weeks after third immunization and serum was isolated. All experiments were conducted in accordance with the guidelines of the Laboratory Animal Center of National Tsing Hua University (NTHU). Animal use protocols were reviewed and approved by the NTHU Institutional Animal Care and Use Committee (approval no. 09733).

H5-Pseudotyped Particles (H5Pp)

Figure 15:
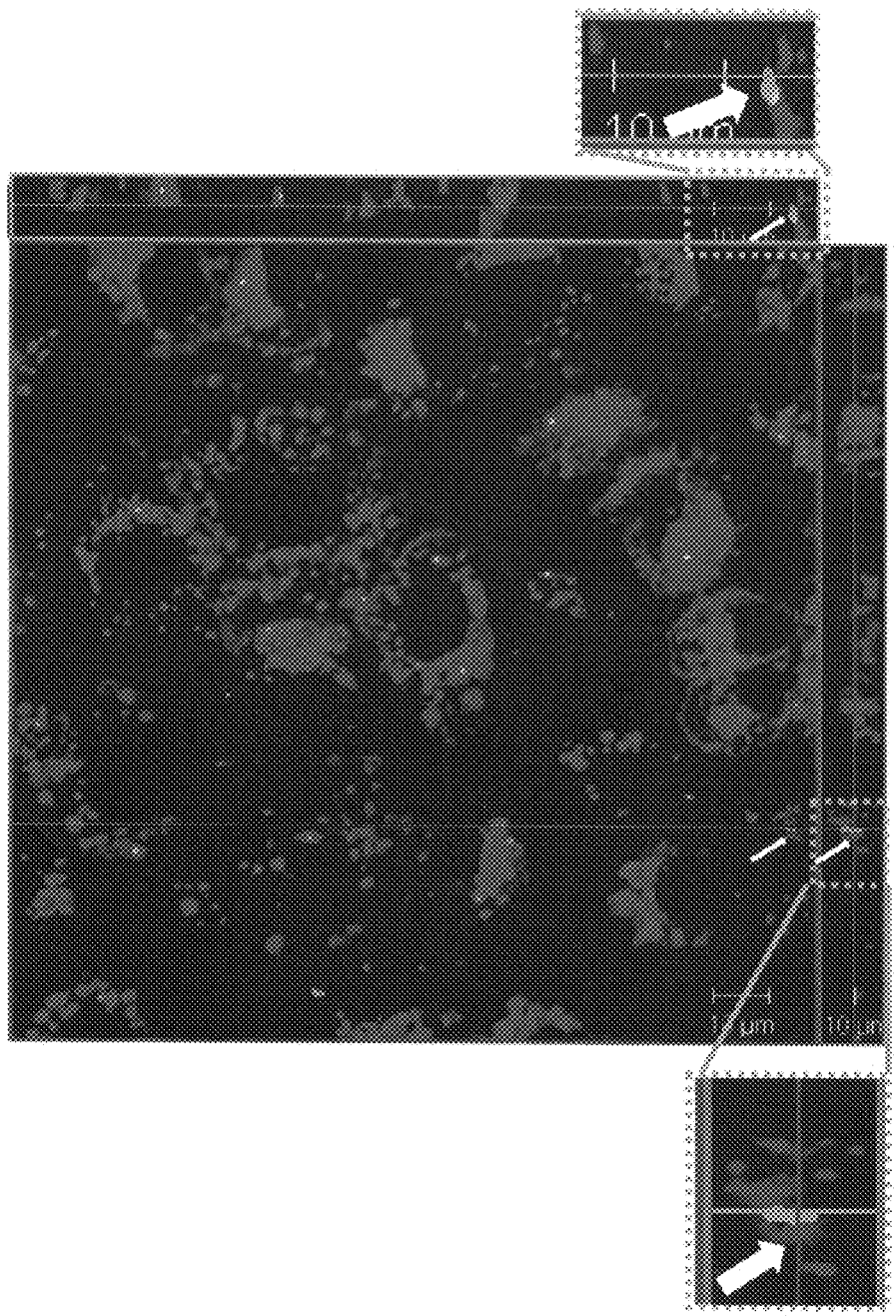
FIG. 15 shows EGFP-VLPs in A549 cells visualized by confocal fluorescence microscopy. A549 cells were labeled with DiD and EGFP-VLPs were labeled with DiI. (A) Excitation by 488 nm line from laser and 633 nm line from laser; (B) excitation by 561 nm line from laser and 633 nm line from laser.
Figure 15:
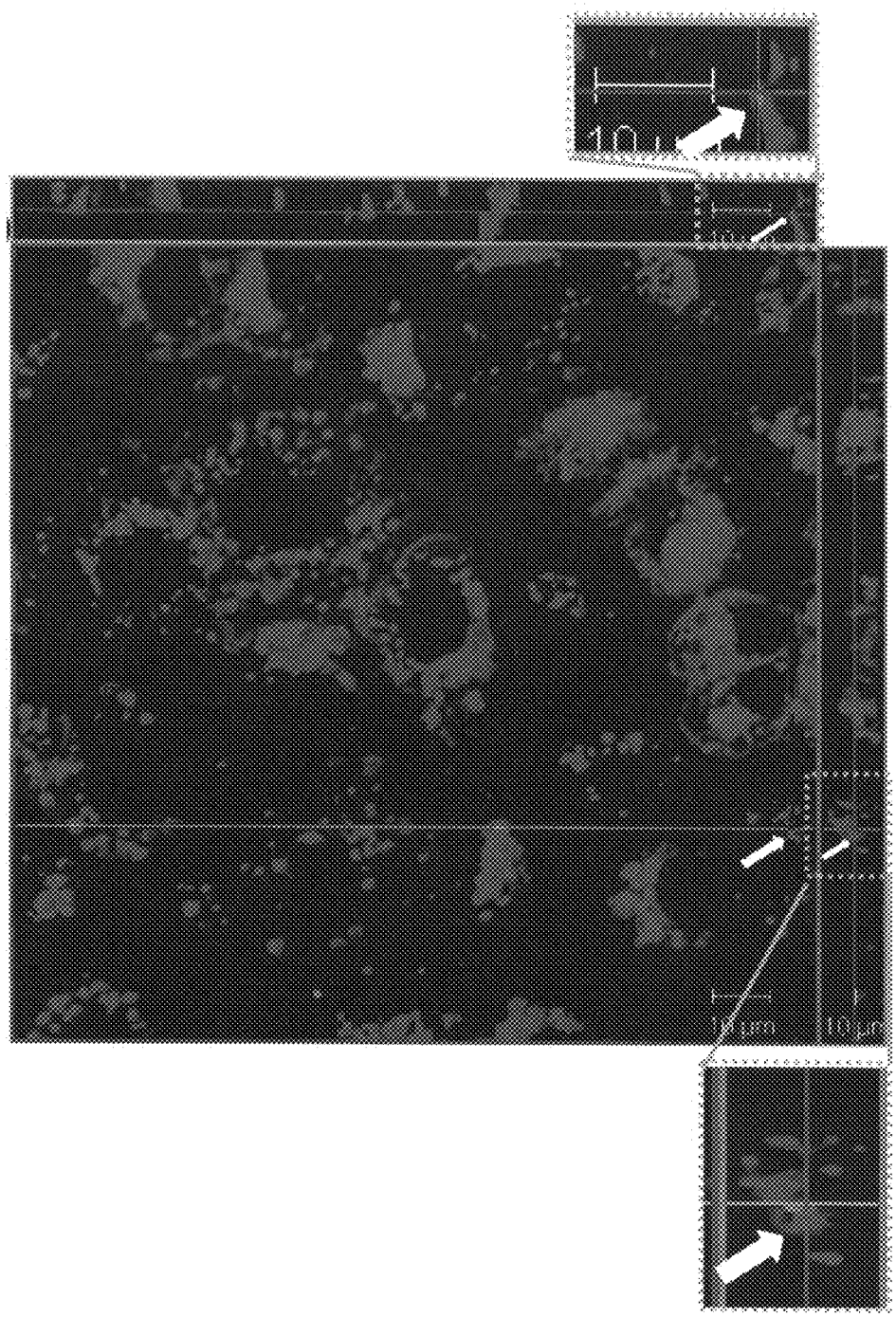

$3 \times 10^6$ HEK293T cells were transfected with pNL-Luc-E⁻R⁻, pcDNA3.1-HA (A/Thailand/1(KAN-1)/2004/H5N1 and A/Anhui/1/2005/H5N1) and pcDNA4B-NA (A/Viet Nam/1203/2004/H5N1) vectors. Cell supernatant that contained pseudotyped HIV-1 particles with H5N1 HA and NA were collected 48 hours post-transfection and purified through a 0.45 μm filter. The supernatant was concentrated by ultracentrifugation at 33,000 rpm for 2.5 hours, and then each pellet was dissolved in 100 μL PBS. An HIV-1 p24 ELISA assay kit (BioChain) was used to quantify the H5pp particles.

Neutralization Assay

MDCK cells (4000 cells/well) were seeded in 100 μL of DMEM in 96-well plates. The amount of 25 ng of p24 H5pp was incubated with two-fold serial dilutions of serum (starting dilution 1:40) for 1 hour at 37° C. in 60 μL DMEM. Then 100 μL of fresh medium was added and 140 μL of the virus-serum mixtures was transferred to the cells. The luciferase assay was performed 48 hours following the direct addition of neolite luciferase substrate (PerkinElmer). The neutralization titer was defined as the reciprocal of the dilution that yielded 50% neutralization determined using an ID50 software.

Analysis of Cytokine Production

DCs were untreated or individually treated with LPS 50 ng/mL from *E. coli* 0111:B4 (Sigma), PBS, 1 μg/mL VLP, FliC-VLP or PRO-VLP for 6 hours, with the addition of a protein transport inhibitor, brefeldin A (10 μg/mL) (Biolegend), for the final 4.5 hours. Cells were then fixed and permeabilized, and the intracellular cytokines were stained with TNF-α mAb (Biolegend). They then underwent flow cytometry (FACS Calibur, BD) and analyzed using CellQuest software (BD Biosciences).

Analysis of DC Maturation

After the BMDCs were untreated or treated with VLPs, FliC-VLPs or PRO-VLPs (5 μg/mL) for 16 hours, the cells and supernatants were harvested and stained with monoclonal antibodies against conjugated CD11c-FliC, conjugated CD40-PE, and conjugated CD86-PE (Biolegend). The cells were then acquired and analyzed using flow cytometry (FACS Calibur, BD).

Results

Baculovirus-Insect Cell Expression of Influenza VLPs

A baculovirus-insect cell expression system was used to prepare the influenza VLPs by the over-expression of two viral proteins (HA, M1), three viral proteins (HA, NA, M1), and four viral proteins (HA, NA, M1, M2). The cDNAs of the four viral proteins were obtained from different influenza virus strains: HA (A/Thailand/1(KAN-1)/2004/H5N1) (SEQ ID NO: 1), NA (A/Viet Nam/1203/2004/H5N1) (SEQ ID NO: 27), M1 (A/WSN/1933/H1N1) (SEQ ID NO: 21) and M2 (A/WSN/1933/H1N1) (SEQ ID NO: 23). These genes were cloned into the baculovirus vector under two promoters, polyhedron (pH) and p10, to generate a series of recombinant baculoviruses (BacHA-M1, BacNA, BacM2-NA) (FIGS. 11A-C). Influenza VLPs were obtained from Sf9 cells that were infected with BacHA-M1 (two viral proteins), co-infected with BacHA-M1 and BacNA, or co-infected with BacHA-M1 and BacM2-NA. Influenza VLPs were obtained from the culture supernatants and purified by ultracentrifugation and sucrose gradient sedimentation. The formation of influenza VLPs was in the sucrose gradient fractions verified by Western blotting in the presence of two viral proteins HA and M1 (FIG. 12A), three viral proteins HA, NA, M1 (FIG. 12B), and four viral proteins HA, NA, M1, M2 (FIG. 12C). The TEM results reveal that the VLPs obtained from infected Sf9 cells were roughly spherical and were pleomorphic. The average diameters of the influenza VLPs were 102±3 nm (N=10) for two viral proteins, 100±4 nm (N=10) for three viral proteins, and 97±13 nm (N=10) for four viral proteins (FIG. 13). Distinctive influenza spike projections were observed on the surface of the VLPs expressed using three and four viral proteins (FIG. 13). The influenza VLPs that were expressed using two, three and four viral proteins were all capable of maintaining red blood cell agglutination as determined from the HA titers of 512 (two viral proteins), 256 (three viral proteins), and 512 (four viral proteins) per 50 μL.

Production of Influenza VLPs with EGFP/M2 Fusion Protein

It was proposed that M2 protein can be used as a molecular fabricator (i) without disrupting the assembly of VLPs and (ii) while retaining the native structures of HA and NA envelope proteins on the particle surfaces. Fabrication of influenza VLPs was obtained by the over-expression of four viral proteins by a direct fusion of M2 to EGFP. The EGFP gene was added to the N terminus of the M2 gene to construct the baculovirus (BacEGFP/M2-NA). Sf9 cells were co-infected with two recombinant baculoviruses (BacHA-M1 and BacEGFP/M2-NA) to generate the EGFP-VLPs. Direct fusion of EGFP to M2 did not influence the formation of VLPs as revealed by the presence of four viral proteins in the sucrose gradient fractions (FIG. 14A) and the TEM visualization of the spherical and pleomorphic particles with an average diameter of 93±13 nm (N=10) (FIGS. 14B-E).

To further show the functionality of the EGFP-VLPs, live cell imaging was used to visualize the uptake of EGFP-VLPs in A549 cells. Using confocal microscopy at various wavelengths of emitted light, green fluorescent spots of the EGFP-VLPs were observed inside the A549 cells with light that was excited at 488 nm (FIG. 15A), and overlapped the red fluorescent spots of the VLPs that were stained with DiI, which is a fluorescent lipophilic dye that was used to label viral membranes within the A549 cells with an excited light wavelength of 561 nm (FIG. 15B). In parallel, A549 cells were labeled with DiD, a fluororescent lipophilic dye for labeling cell membranes, yielding blue fluorescent spots with an excited light wavelength at 633 nm. These results reveal that influenza VLPs can be generated by the M2 fusion of EGFP for imaging single virus entering A549 cells.

Production of Influenza VLPs with Flagellin/M2 and Profilin/M2 Fusion Proteins

Figure 16:
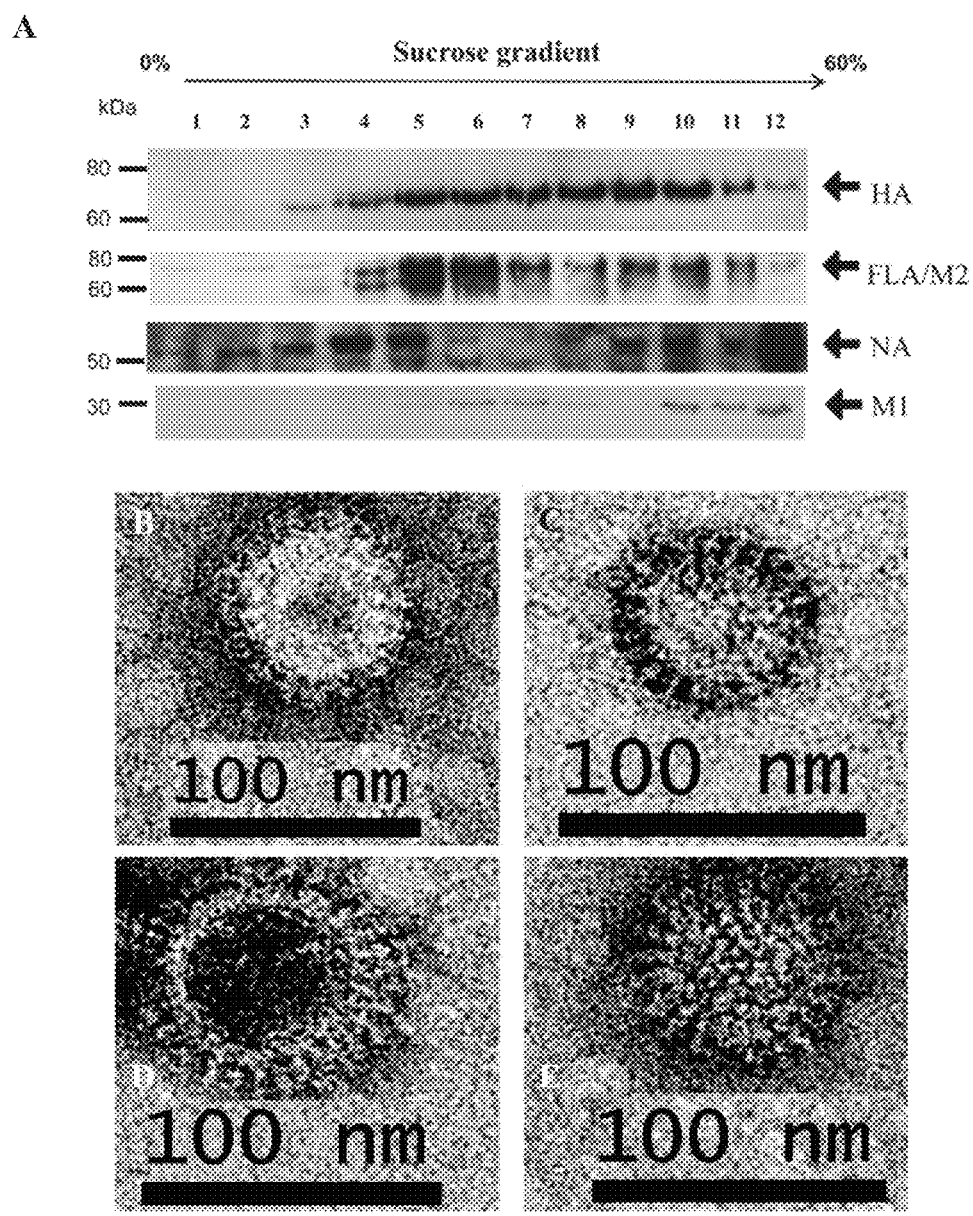
FIG. 16 shows production of influenza VLPs with FliC/M2 fusion protein. (A) Sucrose gradient analysis of influenza VLPs reacted with anti-HA, anti-NA, anti-M1, anti-M2 specific antibodies; (B-E) TEM images of influenza FliC-VLPs that are negatively stained with uranyl acetate, showing quadruple samples.
Figure 17:
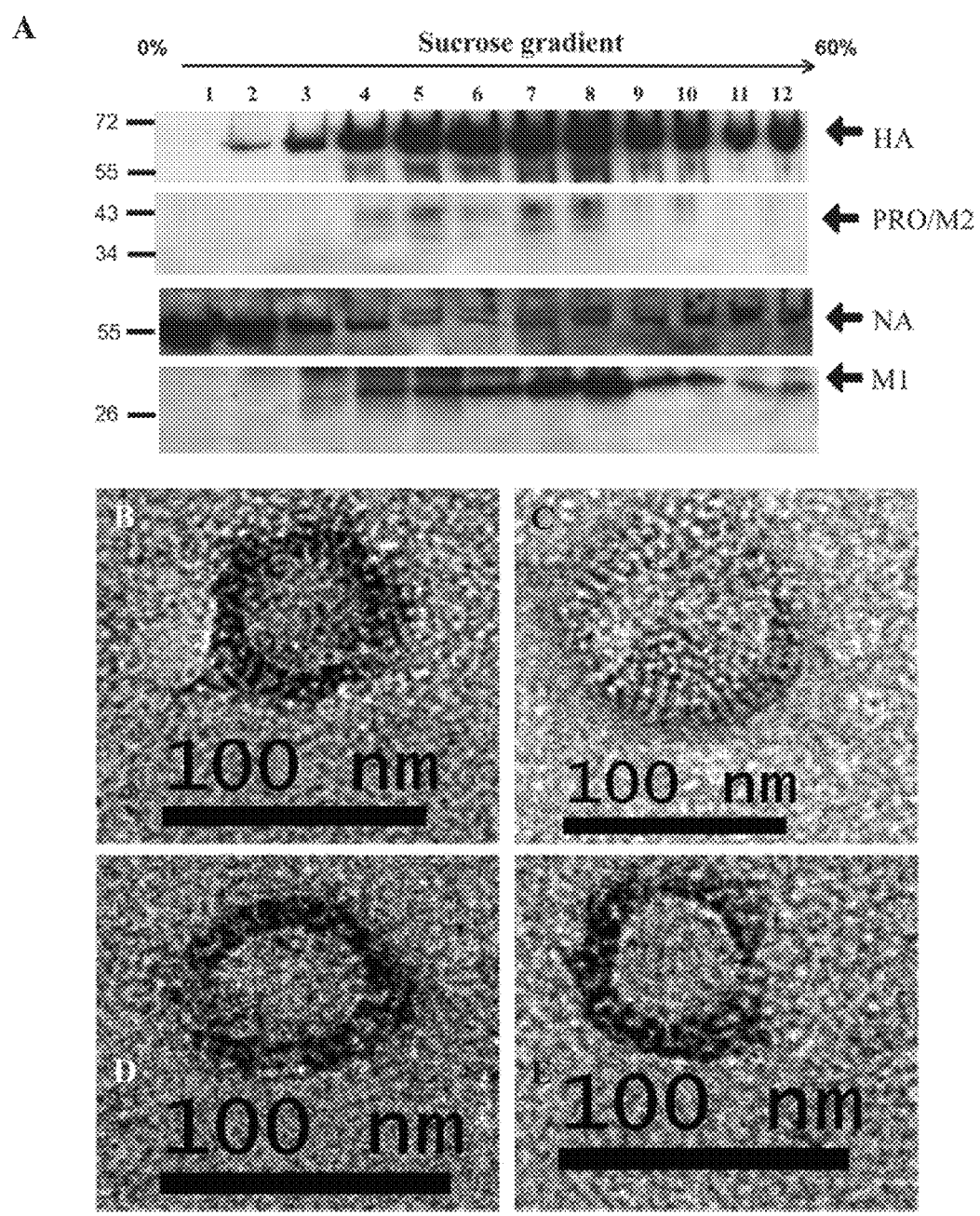
FIG. 17 shows production of influenza VLPs with PRO/M2 fusion protein. (A) Sucrose gradient analysis of the influenza VLPs reacted with anti-HA, anti-NA, anti-M1, and anti-M2 specific antibodies; and (B) TEM images of influenza PRO-VLPs that are negatively stained with uranyl acetate, showing quadruple samples.

Two molecular adjuvants, FliC and PRO, were then replaced with EGFP to generate two molecular adjuvanted VLPs, FliC-VLPs and PRO-VLPs. The full-length genes of FliC and PRO were fused in front of the M2 gene to construct the recombinant baculoviruses, BacFliC/M2-NA and BacPRO/M2-NA. Sf9 cells were co-infected with BacHA-M1 and Bac FliC/M2-NA or BacHA-M1 and BacPRO/M2-NA to yield FliC-VLPs and PRO-VLPs. Direct fusion of FliC and PRO to M2 formed FliC-VLPs (FIG. 16A) and PRO-VLPs (FIG. 17A) as evidenced by the presence of the fusion proteins and other three viral proteins HA, NA, M1 in the sucrose fractionated samples. The morphologies of FliC-VLPs and PRO-VLPs were spherical and pleomorphic, with average diameters of 94±7 nm (N=10) and 94±13 nm (N=10), respectively (FIGS. 6B-E and 17B-E). These results reveal that the molecular adjuvanted VLPs can be obtained using M2 fusion proteins.

Figure 18:
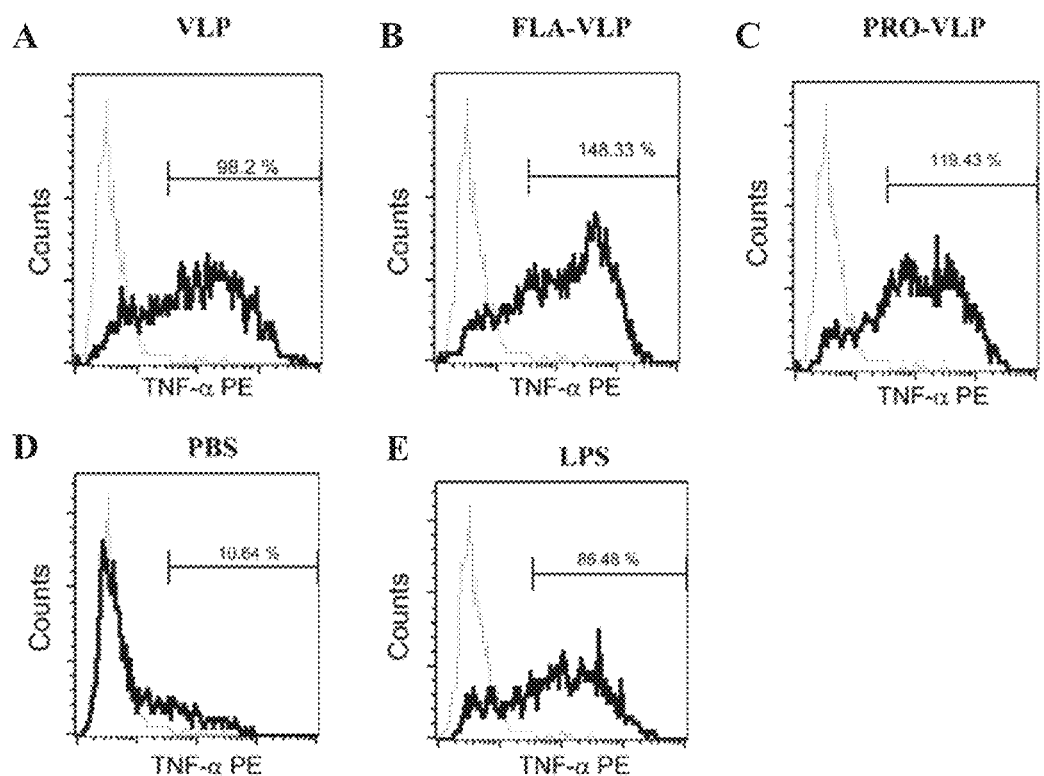
FIG. 18 shows intracellular TNF-α production of BMDCs treated with (A) non-fabricated VLPs, (B) FliC-VLPs, (C) PRO-VLPs, (D) PBS (negative control), or (E) 20 ng/mL LPS (positive control). TNF-α production was detected by FACS analysis in groups of treated (black lines) and untreated (gray lines) BMDCs. Average TNF-α+BMDCs of gated M1 were obtained from at least three independent experiments.
Figure 19:
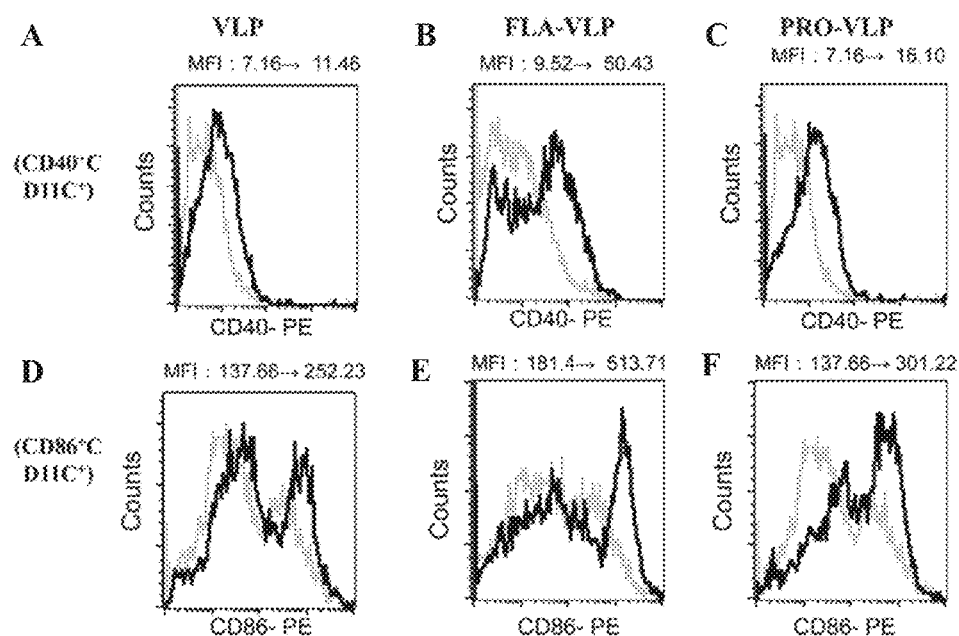
FIG. 19 shows analytic results of CD40 and CD86 surface markers on BMDCs treated with non-fabricated VLPs, FliC-VLPs and PRO-VLPs. The mean fluorescence intensity (MFI) of the groups of treated (black lines) and untreated (gray lines) BMDCs are presented in (A) $CD40^+CD11c^+$ and (B) $CD86^+CD11c^+$ phenotypes. Results are obtained from triplicate experiments.

To study the effects of molecular adjuvanted VLPs on dendritic cells, mouse BMDCs were obtained in vitro, treated with various influenza VLPs (VLPs, FliC-VLPs, PRO-VLPs) and then analyzed using FACS analysis. The results indicate that the production of TNF-α in BMDCs increased from 98.2% (VLP) to 148.3% (FliC-VLP) and 119.4% (PRO-VLP) than in the controls of untreated (10.6%) and LPS-treated BMDC cells (86.5%) (FIG. 18). The maturation of BMDCs that was caused by influenza VLPs was also elucidated by measuring the amount of the co-stimulatory molecules of CD40 and CD86 on the surfaces of BMDCs. The results show that since the mean fluorescence intensities (MFI) of $CD40^+CD11c^+$ and $CD86^+ CD11c^+$ in BMDCs upon treatment with FliC-VLPs and PRO-VLPs increased above those in VLPs (FIG. 19), the molecular adjuvanted VLPs (FliC-VLPs and PRO-VLPs) induced BMDCs to produce more TNF-α and to promote more DC maturation in vitro.

Figure 20:
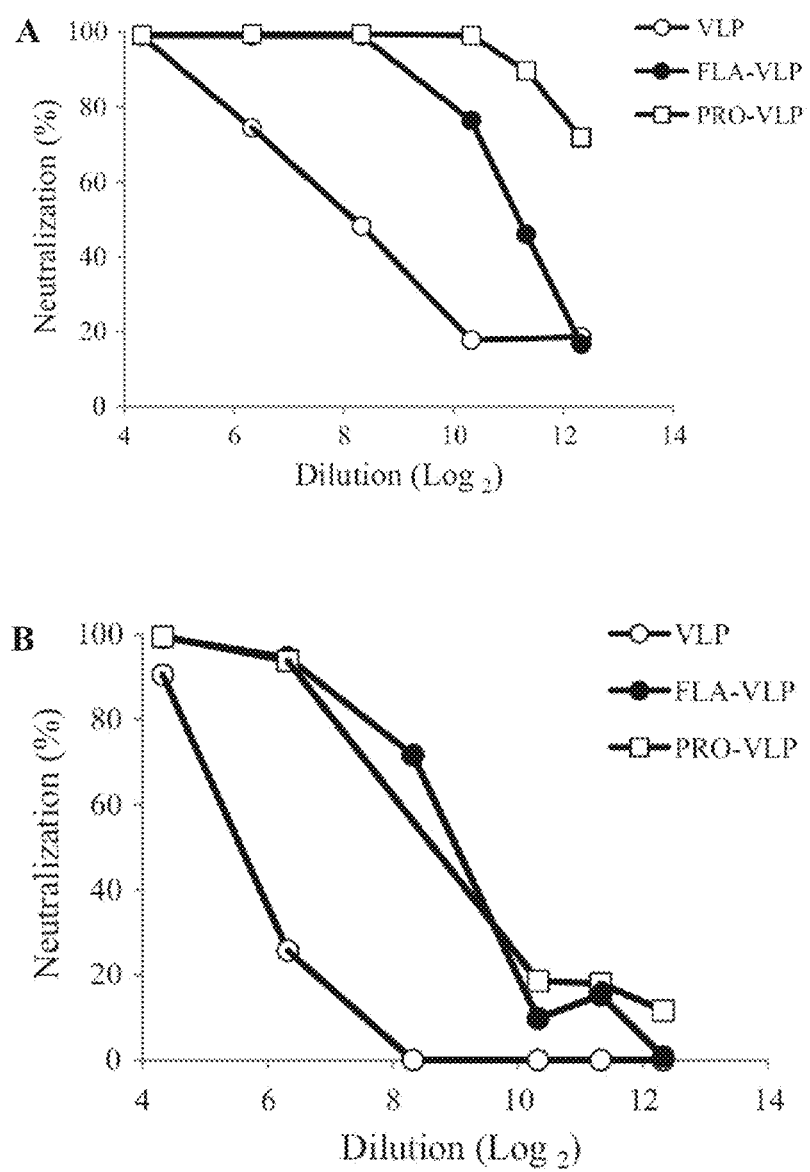
FIG. 20 shows neutralization of antisera collected from mice immunized with VLPs, FliC-VLPs and PRO-VLPs using H5pp of (A) the homologous KAN-1 strain and (B) the heterologous Anhui strain.

To investigate whether immunization with the molecular adjuvated FliC-VLPs and PRO-VLPs can elicit more potent immune responses than the wild-type VLPs, BALB/c mice were immunized with VLPs, FliC-VLPs, and PRO-VLPs at 15 μg (total protein) per dose for three immunizations. The mouse sera were collected one week after the third immunization and analyzed for H5pp neutralization. The results show that the antisera that were collected from mice that have been immunized by VLPs, FliC-VLPs and PRO-VLPs neutralized H5pp of the homologous KAN-1 strain (FIG. 20A) and the heterologous Anhui strain (FIG. 20B) were all in a dose-dependent manner. For neutralization of the homologous strain, the 50% neutralization titers were $\log_2$ 6.5 for VLP antisera, $\log_2$ 11.2 for FliC-VLP antisera, and $\log_2$ 12.8 for PRO-VLP antisera. For neutralization of the heterologous Anhui strain, the 50% neutralization titers were $\log_2$ 5.7 for VLP antisera, $\log_2$ 8.8 for FliC-VLP antisera, and $\log_2$ 9.3 for PRO-VLP antisera. Immunization using the fabricated VLPs that contained the molecular adjuvants (PRO-VLPs and FliC-VLPs) elicited more potent neutralizing antibody responses in mice against the homologous and the heterologous H5N1 viruses than the wild-type VLPs.

What is claimed is:

1. A DNA vaccine comprising a hyperglycosylated mutant HA gene,
   wherein the hyperglycosylated mutant HA gene encodes a protein comprising an amino acid sequence of SEQ ID NO: 4, 6, or 10.

2. The DNA vaccine of claim 1, which elicits an immune response against a plurality of avian influenza virus subtypes in a subject.

3. A DNA vaccine composition comprising:
   (a) a DNA vaccine of claim 1; and
   (b) a booster.

4. The DNA vaccine composition of claim 3, wherein the booster is an influenza virus-like particle (VLP).

5. The DNA vaccine composition of claim 4, wherein the influenza virus-like particle is derived from cell infected by recombinant baculoviruses comprising one or more plasmids containing HA gene, M1 gene, NA gene and FliC-M2 gene, which encodes FliC-M2 fusion protein.

6. The DNA vaccine composition of claim 3, which further comprises an adjuvant.

7. The DNA vaccine composition of claim 6, wherein the adjuvant is an aluminum-containing adjuvant.

8. The DNA vaccine composition of claim 3, wherein the DNA vaccine and the booster have a mass ratio of 5 to 3.

9. The DNA vaccine composition of claim 3, which elicits an immune response against a plurality of avian influenza virus subtypes in a subject.

* * * * *

SEQUENCE LISTING

```
<160> NUMBER OF SEQ ID NOS: 28

<210> SEQ ID NO 1
<211> LENGTH: 1695
<212> TYPE: DNA
<213> ORGANISM: Influenza virus
<220> FEATURE:
<221> NAME/KEY: CDS
<222> LOCATION: (1)..(1695)

<400> SEQUENCE: 1 atg gag aaa att gtc ctg ctg ttc gcc att gtc tca ctg gtc aaa tcc      48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc      96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att     144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa     192
Leu Glu Lys Thr His Asn Gly Lys Leu Cys Asp Leu Asp Gly Val Lys
    50                  55                  60 cca ctc att ctg aga gac tgt agc gtc gct gga tgg ctc ctc ggc aat     240
Pro Leu Ile Leu Arg Asp Cys Ser Val Ala Gly Trp Leu Leu Gly Asn
65                  70                  75                  80
```

-continued

```
cca atg tgt gat gag ttc atc aac gtc ccc gaa tgg tca tac atc gtg      288
Pro Met Cys Asp Glu Phe Ile Asn Val Pro Glu Trp Ser Tyr Ile Val
            85                  90                  95 gag aag gcc aac cct gtg aac gat ctc tgt tac cct ggc gac ttc aac      336
Glu Lys Ala Asn Pro Val Asn Asp Leu Cys Tyr Pro Gly Asp Phe Asn
            100                 105                 110 gat tac gag gaa ctg aaa cat ctg ctg agt agg atc aat cac ttt gaa      384
Asp Tyr Glu Glu Leu Lys His Leu Leu Ser Arg Ile Asn His Phe Glu
            115                 120                 125 aaa att cag att atc ccc aaa tct tcc tgg tcc tcc cat gag gca tct      432
Lys Ile Gln Ile Ile Pro Lys Ser Ser Trp Ser Ser His Glu Ala Ser
130                 135                 140 ctg ggc gtg tca tct gcc tgt cca tac cag agg aaa tcc tca ttc ttc      480
Leu Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc      528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg      576
Lys Arg Ser Tyr Asn Asn Thr Asn Gln Glu Asp Leu Leu Val Leu Trp
                180                 185                 190 gga att cat cac ccc aat gat gcc gcc gag cag aca aaa ctg tac cag      624
Gly Ile His His Pro Asn Asp Ala Ala Glu Gln Thr Lys Leu Tyr Gln
                195                 200                 205 aac cct acc aca tac att tct gtg ggc acc tct aca ctg aat cag agg      672
Asn Pro Thr Thr Tyr Ile Ser Val Gly Thr Ser Thr Leu Asn Gln Arg
            210                 215                 220 ctg gtg cct aga att gcc act agg agt aaa gtc aac ggc cag tcc ggc      720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac      768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc      816
Phe Glu Ser Asn Gly Asn Phe Ile Ala Pro Glu Tyr Ala Tyr Lys Ile
                260                 265                 270 gtg aaa aag ggc gac tcc act atc atg aaa tcc gag ctg gag tac gga      864
Val Lys Lys Gly Asp Ser Thr Ile Met Lys Ser Glu Leu Glu Tyr Gly
                275                 280                 285 aac tgt aac acc aaa tgc cag acc cct atg ggc gct atc aac tct tct      912
Asn Cys Asn Thr Lys Cys Gln Thr Pro Met Gly Ala Ile Asn Ser Ser
            290                 295                 300 atg ccc ttc cac aac atc cac cct ctc act atc ggc gaa tgc cca aaa      960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca     1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att     1056
Pro Gln Arg Glu Thr Arg Gly Leu Phe Gly Ala Ile Ala Gly Phe Ile
                340                 345                 350 gag gga ggc tgg cag gga atg gtc gat ggc tgg tac gga tac cat cac     1104
Glu Gly Gly Trp Gln Gly Met Val Asp Gly Trp Tyr Gly Tyr His His
            355                 360                 365 tcc aat gag cag gga tct gga tac gct gcc gat aag gag tcc acc cag     1152
Ser Asn Glu Gln Gly Ser Gly Tyr Ala Ala Asp Lys Glu Ser Thr Gln
370                 375                 380 aaa gca atc gat ggc gtc acc aac aaa gtc aat tca atc atc gac aaa     1200
Lys Ala Ile Asp Gly Val Thr Asn Lys Val Asn Ser Ile Ile Asp Lys
```

```
atg aac acc cag ttc gag gct gtg gga cga gag ttc aat aac ctg gag    1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat    1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga    1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc    1392
Thr Leu Asp Phe His Asp Ser Asn Val Lys Asn Leu Tyr Asp Lys Val
450                 455                 460 cgg ctc cag ctg agg gat aat gcc aag gaa ctc gga aat ggc tgc ttc    1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac    1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga    1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att    1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg    1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc    1680
Val Ala Gly Leu Ser Leu Trp Met Cys Ser Asn Gly Ser Leu Gln Cys
545                 550                 555                 560 cgg atc tgt atc tag                                                1695
Arg Ile Cys Ile
```

<210> SEQ ID NO 2
<211> LENGTH: 564
<212> TYPE: PRT
<213> ORGANISM: Influenza virus

<400> SEQUENCE: 2

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140
```

-continued

```
Leu Gly Val Ser Ser Ala Cys Pro Tyr Gln Arg Lys Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
                180                 185                 190

Gly Ile His His Pro Asn Asp Ala Ala Glu Gln Thr Lys Leu Tyr Gln
                195                 200                 205

Asn Pro Thr Thr Tyr Ile Ser Val Gly Thr Ser Thr Leu Asn Gln Arg
210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Thr Ile Met Lys Ser Glu Leu Glu Tyr Gly
                275                 280                 285

Asn Cys Asn Thr Lys Cys Gln Thr Pro Met Gly Ala Ile Asn Ser Ser
                290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
                340                 345                 350

Glu Gly Gly Trp Gln Gly Met Val Asp Gly Trp Tyr Gly Tyr His His
                355                 360                 365

Ser Asn Glu Gln Gly Ser Gly Tyr Ala Ala Asp Lys Glu Ser Thr Gln
                370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
                420                 425                 430

Val Trp Thr Tyr Asn Ala Glu Leu Leu Val Leu Met Glu Asn Glu Arg
                435                 440                 445

Thr Leu Asp Phe His Asp Ser Asn Val Lys Asn Leu Tyr Asp Lys Val
                450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
                500                 505                 510

Glu Glu Ile Ser Gly Val Lys Leu Glu Ser Ile Gly Ile Tyr Gln Ile
                515                 520                 525

Leu Ser Ile Tyr Ser Thr Val Ala Ser Ser Leu Ala Leu Ala Ile Met
                530                 535                 540

Val Ala Gly Leu Ser Leu Trp Met Cys Ser Asn Gly Ser Leu Gln Cys
545                 550                 555                 560
```

Arg Ile Cys Ile

<210> SEQ ID NO 3
<211> LENGTH: 1695
<212> TYPE: DNA
<213> ORGANISM: Influenza virus
<220> FEATURE:
<221> NAME/KEY: CDS
<222> LOCATION: (1)..(1695)

<400> SEQUENCE: 3

| | | | | | | | | | | | | | | | | |
|---|---|---|---|---|---|---|---|---|---|---|---|---|---|---|---|---|
| atg | gag | aaa | att | gtc | ctg | ctg | ttc | gcc | att | gtc | tca | ctg | gtc | aaa | tcc | 48 |
| Met | Glu | Lys | Ile | Val | Leu | Leu | Phe | Ala | Ile | Val | Ser | Leu | Val | Lys | Ser | |
| 1 | | | | 5 | | | | | 10 | | | | | 15 | | |
| gat | cag | atc | tgt | att | ggc | tac | cac | gcc | aac | aat | agc | act | gaa | cag | gtc | 96 |
| Asp | Gln | Ile | Cys | Ile | Gly | Tyr | His | Ala | Asn | Asn | Ser | Thr | Glu | Gln | Val | |
| | | | 20 | | | | | 25 | | | | | 30 | | | |
| gac | act | att | atg | gaa | aaa | aac | gtg | acc | gtc | aca | cat | gct | cag | gat | att | 144 |
| Asp | Thr | Ile | Met | Glu | Lys | Asn | Val | Thr | Val | Thr | His | Ala | Gln | Asp | Ile | |
| | | | 35 | | | | | 40 | | | | | 45 | | | |
| ctc | gaa | aaa | acc | cac | aac | ggg | aaa | ctc | tgt | gat | ctc | gac | gga | gtg | aaa | 192 |
| Leu | Glu | Lys | Thr | His | Asn | Gly | Lys | Leu | Cys | Asp | Leu | Asp | Gly | Val | Lys | |
| | 50 | | | | | 55 | | | | | 60 | | | | | |
| cca | ctc | att | ctg | aga | gac | tgt | agc | gtc | gct | gga | tgg | ctc | ctc | ggc | aat | 240 |
| Pro | Leu | Ile | Leu | Arg | Asp | Cys | Ser | Val | Ala | Gly | Trp | Leu | Leu | Gly | Asn | |
| 65 | | | | | 70 | | | | | 75 | | | | | 80 | |
| cca | atg | tgt | gat | gag | ttc | atc | aac | gtc | ccc | gaa | tgg | tca | tac | atc | gtg | 288 |
| Pro | Met | Cys | Asp | Glu | Phe | Ile | Asn | Val | Pro | Glu | Trp | Ser | Tyr | Ile | Val | |
| | | | | 85 | | | | | 90 | | | | | 95 | | |
| gag | aag | aac | aac | acc | gtg | aac | gat | ctc | tgt | tac | cct | ggc | gac | ttc | aac | 336 |
| Glu | Lys | Asn | Asn | Thr | Val | Asn | Asp | Leu | Cys | Tyr | Pro | Gly | Asp | Phe | Asn | |
| | | | 100 | | | | | 105 | | | | | 110 | | | |
| gat | tac | gag | gaa | ctg | aaa | cat | ctg | ctg | agt | agg | atc | aat | cac | ttt | gaa | 384 |
| Asp | Tyr | Glu | Glu | Leu | Lys | His | Leu | Leu | Ser | Arg | Ile | Asn | His | Phe | Glu | |
| | | 115 | | | | | 120 | | | | | 125 | | | | |
| aaa | att | cag | att | atc | ccc | aaa | tct | tcc | tgg | tcc | tcc | cat | gag | gca | tct | 432 |
| Lys | Ile | Gln | Ile | Ile | Pro | Lys | Ser | Ser | Trp | Ser | Ser | His | Glu | Ala | Ser | |
| | 130 | | | | | 135 | | | | | 140 | | | | | |
| ctg | ggc | gtg | tca | tct | gcc | tgt | cca | tac | cag | agg | aaa | tcc | tca | ttc | ttc | 480 |
| Leu | Gly | Val | Ser | Ser | Ala | Cys | Pro | Tyr | Gln | Arg | Lys | Ser | Ser | Phe | Phe | |
| 145 | | | | | 150 | | | | | 155 | | | | | 160 | |
| cgg | aac | gtg | gtg | tgg | ctc | atc | aaa | aaa | aac | tcc | acc | tac | ccc | acc | atc | 528 |
| Arg | Asn | Val | Val | Trp | Leu | Ile | Lys | Lys | Asn | Ser | Thr | Tyr | Pro | Thr | Ile | |
| | | | | 165 | | | | | 170 | | | | | 175 | | |
| aaa | cgc | tct | tac | aac | aac | aca | aat | cag | gag | gat | ctg | ctg | gtc | ctc | tgg | 576 |
| Lys | Arg | Ser | Tyr | Asn | Asn | Thr | Asn | Gln | Glu | Asp | Leu | Leu | Val | Leu | Trp | |
| | | | 180 | | | | | 185 | | | | | 190 | | | |
| gga | att | cat | cac | ccc | aat | gat | gcc | gcc | gag | cag | aca | aaa | ctg | tac | cag | 624 |
| Gly | Ile | His | His | Pro | Asn | Asp | Ala | Ala | Glu | Gln | Thr | Lys | Leu | Tyr | Gln | |
| | | | 195 | | | | | 200 | | | | | 205 | | | |
| aac | cct | acc | aca | tac | att | tct | gtg | ggc | acc | tct | aca | ctg | aat | cag | agg | 672 |
| Asn | Pro | Thr | Thr | Tyr | Ile | Ser | Val | Gly | Thr | Ser | Thr | Leu | Asn | Gln | Arg | |
| | 210 | | | | | 215 | | | | | 220 | | | | | |
| ctg | gtg | cct | aga | att | gcc | act | agg | agt | aaa | gtc | aac | ggc | cag | tcc | ggc | 720 |
| Leu | Val | Pro | Arg | Ile | Ala | Thr | Arg | Ser | Lys | Val | Asn | Gly | Gln | Ser | Gly | |
| 225 | | | | | 230 | | | | | 235 | | | | | 240 | |
| cgg | atg | gaa | ttc | ttt | tgg | acc | atc | ctc | aaa | ccc | aac | gat | gct | atc | aac | 768 |
| Arg | Met | Glu | Phe | Phe | Trp | Thr | Ile | Leu | Lys | Pro | Asn | Asp | Ala | Ile | Asn | |
| | | | | 245 | | | | | 250 | | | | | 255 | | |
| ttc | gag | tca | aac | ggc | aac | ttt | atc | gcc | cct | gaa | tac | gcc | tac | aaa | atc | 816 |
| Phe | Glu | Ser | Asn | Gly | Asn | Phe | Ile | Ala | Pro | Glu | Tyr | Ala | Tyr | Lys | Ile | |

```
                   260               265               270
gtg aaa aag ggc gac tcc act atc atg aaa tcc gag ctg gag tac gga    864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct    912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa    960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca    1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att    1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac    1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag    1152
Ser Asn Glu Gln Gly Ser Gly Tyr Ala Ala Asp Lys Glu Ser Thr Gln
    370                 375                 380 aaa gca atc gat ggc gtc acc aac aaa gtc aat tca atc atc gac aaa    1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag    1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat    1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga    1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc    1392
Thr Leu Asp Phe His Asp Ser Asn Val Lys Asn Leu Tyr Asp Lys Val
    450                 455                 460 cgg ctc cag ctg agg gat aat gcc aag gaa ctc gga aat ggc tgc ttc    1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac    1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga    1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att    1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg    1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc    1680
Val Ala Gly Leu Ser Leu Trp Met Cys Ser Asn Gly Ser Leu Gln Cys
545                 550                 555                 560 cgg atc tgt atc tag                                                 1695
Arg Ile Cys Ile

<210> SEQ ID NO 4
```

<211> LENGTH: 564
<212> TYPE: PRT
<213> ORGANISM: Influenza virus

<400> SEQUENCE: 4

```
Met Glu Lys Ile Val

```
                385                 390                 395                 400
        Met Asn Thr Gln Phe Glu Ala Val Gly Arg Glu Phe Asn Asn Leu Glu
                        405                 410                 415

Arg Arg Ile Glu Asn Leu Asn Lys Lys Met Glu Asp Gly Phe Leu Asp
                        420                 425                 430

Val Trp Thr Tyr Asn Ala Glu Leu Leu Val Leu Met Glu Asn Glu Arg
                        435                 440                 445

Thr Leu Asp Phe His Asp Ser Asn Val Lys Asn Leu Tyr Asp Lys Val
                    450                 455                 460

Arg Leu Gln Leu Arg Asp Asn Ala Lys Glu Leu Gly Asn Gly Cys Phe
        465                 470                 475                 480

Glu Phe Tyr His Lys Cys Asp Asn Glu Cys Met Glu Ser Val Arg Asn
                            485                 490                 495

Gly Thr Tyr Asp Tyr Pro Gln Tyr Ser Glu Glu Ala Arg Leu Lys Arg
                        500                 505                 510

Glu Glu Ile Ser Gly Val Lys Leu Glu Ser Ile Gly Ile Tyr Gln Ile
                        515                 520                 525

Leu Ser Ile Tyr Ser Thr Val Ala Ser Ser Leu Ala Leu Ala Ile Met
                    530                 535                 540

Val Ala Gly Leu Ser Leu Trp Met Cys Ser Asn Gly Ser Leu Gln Cys
        545                 550                 555                 560

Arg Ile Cys Ile

<210> SEQ ID NO 5
        <211> LENGTH: 1695
        <212> TYPE: DNA
        <213> ORGANISM: Influenza virus
        <220> FEATURE:
        <221> NAME/KEY: CDS
        <222> LOCATION: (1)..(1695)

<400> SEQUENCE: 5 atg gag aaa att gtc ctg ctg ttc gcc att gtc tca ctg gtc aaa tcc      48
        Met Glu Lys Ile Val Leu Leu Phe Ala Ile Val Ser Leu Val Lys Ser
        1               5                   10                  15 gat cag atc tgt att ggc tac cac gcc aac aat agc act gaa cag gtc      96
        Asp Gln Ile Cys Ile Gly Tyr His Ala Asn Asn Ser Thr Glu Gln Val
                        20                  25                  30 gac act att atg gaa aaa aac gtg acc gtc aca cat gct cag gat att     144
        Asp Thr Ile Met Glu Lys Asn Val Thr Val Thr His Ala Gln Asp Ile
                    35                  40                  45 ctc gaa aaa acc cac aac ggg aaa ctc tgt gat ctc gac gga gtg aaa     192
        Leu Glu Lys Thr His Asn Gly Lys Leu Cys Asp Leu Asp Gly Val Lys
            50                  55                  60 cca ctc att ctg aga gac tgt agc gtc gct gga tgg ctc ctc ggc aat     240
        Pro Leu Ile Leu Arg Asp Cys Ser Val Ala Gly Trp Leu Leu Gly Asn
        65                  70                  75                  80 cca atg tgt gat gag ttc atc aac gtc ccc gaa tgg tca tac atc gtg     288
        Pro Met Cys Asp Glu Phe Ile Asn Val Pro Glu Trp Ser Tyr Ile Val
                            85                  90                  95 gag aag gcc aac cct aac aac acc ctc tgt tac cct ggc gac ttc aac     336
        Glu Lys Ala Asn Pro Asn Asn Thr Leu Cys Tyr Pro Gly Asp Phe Asn
                        100                 105                 110 gat tac gag gaa ctg aaa cat ctg ctg agt agg atc aat cac ttt gaa     384
        Asp Tyr Glu Glu Leu Lys His Leu Leu Ser Arg Ile Asn His Phe Glu
                    115                 120                 125 aaa att cag att atc ccc aaa tct tcc tgg tcc tcc cat gag gca tct     432
        Lys Ile Gln Ile Ile Pro Lys Ser Ser Trp Ser Ser His Glu Ala Ser
```

-continued

| | | | | | | | | | | | | | | | |
|---|---|---|---|---|---|---|---|---|---|---|---|---|---|---|---|
| | | 130 | | | | | 135 | | | | | 140 | | | |
| ctg | ggc | gtg | tca | tct | gcc | tgt | cca | tac | cag | agg | aaa | tcc | tca | ttc | ttc | 480 |
| Leu | Gly | Val | Ser | Ser | Ala | Cys | Pro | Tyr | Gln | Arg | Lys | Ser | Ser | Phe | Phe | |
| 145 | | | | 150 | | | | | 155 | | | | | 160 | | |

| cgg | aac | gtg | gtg | tgg | ctc | atc | aaa | aaa | aac | tcc | acc | tac | ccc | acc | atc | 528 |
| Arg | Asn | Val | Val | Trp | Leu | Ile | Lys | Lys | Asn | Ser | Thr | Tyr | Pro | Thr | Ile | |
| | | | | 165 | | | | | 170 | | | | | 175 | | |

| aaa | cgc | tct | tac | aac | aac | aca | aat | cag | gag | gat | ctg | ctg | gtc | ctc | tgg | 576 |
| Lys | Arg | Ser | Tyr | Asn | Asn | Thr | Asn | Gln | Glu | Asp | Leu | Leu | Val | Leu | Trp | |
| | | | 180 | | | | | 185 | | | | | 190 | | | |

| gga | att | cat | cac | ccc | aat | gat | gcc | gcc | gag | cag | aca | aaa | ctg | tac | cag | 624 |
| Gly | Ile | His | His | Pro | Asn | Asp | Ala | Ala | Glu | Gln | Thr | Lys | Leu | Tyr | Gln | |
| | | | | 195 | | | | | 200 | | | | | 205 | | |

| aac | cct | acc | aca | tac | att | tct | gtg | ggc | acc | tct | aca | ctg | aat | cag | agg | 672 |
| Asn | Pro | Thr | Thr | Tyr | Ile | Ser | Val | Gly | Thr | Ser | Thr | Leu | Asn | Gln | Arg | |
| | | 210 | | | | | 215 | | | | | 220 | | | | |

| ctg | gtg | cct | aga | att | gcc | act | agg | agt | aaa | gtc | aac | ggc | cag | tcc | ggc | 720 |
| Leu | Val | Pro | Arg | Ile | Ala | Thr | Arg | Ser | Lys | Val | Asn | Gly | Gln | Ser | Gly | |
| 225 | | | | 230 | | | | | 235 | | | | | 240 | | |

| cgg | atg | gaa | ttc | ttt | tgg | acc | atc | ctc | aaa | ccc | aac | gat | gct | atc | aac | 768 |
| Arg | Met | Glu | Phe | Phe | Trp | Thr | Ile | Leu | Lys | Pro | Asn | Asp | Ala | Ile | Asn | |
| | | | | 245 | | | | | 250 | | | | | 255 | | |

| ttc | gag | tca | aac | ggc | aac | ttt | atc | gcc | cct | gaa | tac | gcc | tac | aaa | atc | 816 |
| Phe | Glu | Ser | Asn | Gly | Asn | Phe | Ile | Ala | Pro | Glu | Tyr | Ala | Tyr | Lys | Ile | |
| | | | 260 | | | | | 265 | | | | | 270 | | | |

| gtg | aaa | aag | ggc | gac | tcc | act | atc | atg | aaa | tcc | gag | ctg | gag | tac | gga | 864 |
| Val | Lys | Lys | Gly | Asp | Ser | Thr | Ile | Met | Lys | Ser | Glu | Leu | Glu | Tyr | Gly | |
| | | | | 275 | | | | | 280 | | | | | 285 | | |

| aac | tgt | aac | acc | aaa | tgc | cag | acc | cct | atg | ggc | gct | atc | aac | tct | tct | 912 |
| Asn | Cys | Asn | Thr | Lys | Cys | Gln | Thr | Pro | Met | Gly | Ala | Ile | Asn | Ser | Ser | |
| | | 290 | | | | | 295 | | | | | 300 | | | | |

| atg | ccc | ttc | cac | aac | atc | cac | cct | ctc | act | atc | ggc | gaa | tgc | cca | aaa | 960 |
| Met | Pro | Phe | His | Asn | Ile | His | Pro | Leu | Thr | Ile | Gly | Glu | Cys | Pro | Lys | |
| 305 | | | | 310 | | | | | 315 | | | | | 320 | | |

| tac | gtc | aaa | tca | aac | cgg | ctc | gtg | ctg | gct | act | ggg | ctg | aga | aac | tca | 1008 |
| Tyr | Val | Lys | Ser | Asn | Arg | Leu | Val | Leu | Ala | Thr | Gly | Leu | Arg | Asn | Ser | |
| | | | | 325 | | | | | 330 | | | | | 335 | | |

| cct | cag | cga | gag | act | aga | ggc | ctg | ttt | ggc | gcc | att | gct | gga | ttc | att | 1056 |
| Pro | Gln | Arg | Glu | Thr | Arg | Gly | Leu | Phe | Gly | Ala | Ile | Ala | Gly | Phe | Ile | |
| | | | | 340 | | | | | 345 | | | | | 350 | | |

| gag | gga | ggc | tgg | cag | gga | atg | gtc | gat | ggc | tgg | tac | gga | tac | cat | cac | 1104 |
| Glu | Gly | Gly | Trp | Gln | Gly | Met | Val | Asp | Gly | Trp | Tyr | Gly | Tyr | His | His | |
| | | | 355 | | | | | 360 | | | | | 365 | | | |

| tcc | aat | gag | cag | gga | tct | gga | tac | gct | gcc | gat | aag | gag | tcc | acc | cag | 1152 |
| Ser | Asn | Glu | Gln | Gly | Ser | Gly | Tyr | Ala | Ala | Asp | Lys | Glu | Ser | Thr | Gln | |
| | | 370 | | | | | 375 | | | | | 380 | | | | |

| aaa | gca | atc | gat | ggc | gtc | acc | aac | aaa | gtc | aat | tca | atc | atc | gac | aaa | 1200 |
| Lys | Ala | Ile | Asp | Gly | Val | Thr | Asn | Lys | Val | Asn | Ser | Ile | Ile | Asp | Lys | |
| 385 | | | | 390 | | | | | 395 | | | | | 400 | | |

| atg | aac | acc | cag | ttc | gag | gct | gtg | gga | cga | gag | ttc | aat | aac | ctg | gag | 1248 |
| Met | Asn | Thr | Gln | Phe | Glu | Ala | Val | Gly | Arg | Glu | Phe | Asn | Asn | Leu | Glu | |
| | | | | 405 | | | | | 410 | | | | | 415 | | |

| cgg | aga | atc | gaa | aac | ctg | aac | aaa | aaa | atg | gag | gac | ggc | ttc | ctc | gat | 1296 |
| Arg | Arg | Ile | Glu | Asn | Leu | Asn | Lys | Lys | Met | Glu | Asp | Gly | Phe | Leu | Asp | |
| | | | | 420 | | | | | 425 | | | | | 430 | | |

| gtg | tgg | acc | tac | aat | gct | gaa | ctg | ctg | gtg | ctc | atg | gaa | aac | gag | aga | 1344 |
| Val | Trp | Thr | Tyr | Asn | Ala | Glu | Leu | Leu | Val | Leu | Met | Glu | Asn | Glu | Arg | |
| | | | 435 | | | | | 440 | | | | | 445 | | | |

| acc | ctg | gac | ttc | cac | gac | tca | aac | gtg | aaa | aac | ctg | tac | gac | aaa | gtc | 1392 |

-continued

```
                    Thr Leu Asp Phe His Asp Ser Asn Val Lys Asn Leu Tyr Asp Lys Val
                        450                 455                 460 cgg ctc cag ctg agg gat aat gcc aag gaa ctc gga aat ggc tgc ttc         1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac         1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga         1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att         1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg         1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc         1680
Val Ala Gly Leu Ser Leu Trp Met Cys Ser Asn Gly Ser Leu Gln Cys
545                 550                 555                 560 cgg atc tgt atc tag                                                     1695
Arg Ile Cys Ile
```

<210> SEQ ID NO 6
<211> LENGTH: 564
<212> TYPE: PRT
<213> ORGANISM: Influenza virus

<400> SEQUENCE: 6

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Asn Asn Thr Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser His Glu Ala Ser
    130                 135                 140

Leu Gly Val Ser Ser Ala Cys Pro Tyr Gln Arg Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220
```

```
Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
        260                 265                 270

Val Lys Lys Gly Asp Ser Thr Ile Met Lys Ser Glu Leu Glu Tyr Gly
    275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
        515                 520                 525

Leu Ser Ile Tyr Ser Thr Val Ala Ser Ser Leu Ala Leu Ala Ile Met
530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 7
<211> LENGTH: 1695
<212> TYPE: DNA
<213> ORGANISM: Influenza virus
<220> FEATURE:
<221> NAME/KEY: CDS
<222> LOCATION: (1)..(1695)

<400> SEQUENCE: 7 atg gag aaa att gtc ctg ctg ttc gcc att gtc tca ctg gtc aaa tcc    48
Met Glu Lys Ile Val Leu Leu Phe Ala Ile Val Ser Leu Val Lys Ser
```

```
    1               5                   10                  15
gat cag atc tgt att ggc tac cac gcc aac aat agc act gaa cag gtc        96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att       144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa       192
Leu Glu Lys Thr His Asn Gly Lys Leu Cys Asp Leu Asp Gly Val Lys
50                  55                  60 cca ctc att ctg aga gac tgt agc gtc gct gga tgg ctc ctc ggc aat       240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg       288
Pro Met Cys Asp Glu Phe Ile Asn Val Pro Glu Trp Ser Tyr Ile Val
            85                  90                  95 gag aag gcc aac cct gtg aac gat ctc tgt tac cct ggc aac ttc acc       336
Glu Lys Ala Asn Pro Val Asn Asp Leu Cys Tyr Pro Gly Asn Phe Thr
            100                 105                 110 gat tac gag gaa ctg aaa cat ctg ctg agt agg atc aat cac ttt gaa       384
Asp Tyr Glu Glu Leu Lys His Leu Leu Ser Arg Ile Asn His Phe Glu
        115                 120                 125 aaa att cag att atc ccc aaa tct tcc tgg tcc tcc cat gag gca tct       432
Lys Ile Gln Ile Ile Pro Lys Ser Ser Trp Ser Ser His Glu Ala Ser
    130                 135                 140 ctg ggc gtg tca tct gcc tgt cca tac cag agg aaa tcc tca ttc ttc       480
Leu Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc       528
Arg Asn Val Val Trp Leu Ile Lys Lys Asn Ser Thr Tyr Pro Thr Ile
            165                 170                 175 aaa cgc tct tac aac aac aca aat cag gag gat ctg ctg gtc ctc tgg       576
Lys Arg Ser Tyr Asn Asn Thr Asn Gln Glu Asp Leu Leu Val Leu Trp
            180                 185                 190 gga att cat cac ccc aat gat gcc gcc gag cag aca aaa ctg tac cag       624
Gly Ile His His Pro Asn Asp Ala Ala Glu Gln Thr Lys Leu Tyr Gln
        195                 200                 205 aac cct acc aca tac att tct gtg ggc acc tct aca ctg aat cag agg       672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc       720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac       768
Arg Met Glu Phe Phe Trp Thr Ile Leu Lys Pro Asn Asp Ala Ile Asn
            245                 250                 255 ttc gag tca aac ggc aac ttt atc gcc cct gaa tac gcc tac aaa atc       816
Phe Glu Ser Asn Gly Asn Phe Ile Ala Pro Glu Tyr Ala Tyr Lys Ile
            260                 265                 270 gtg aaa aag ggc gac tcc act atc atg aaa tcc gag ctg gag tac gga       864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct       912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa       960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca      1008
```

```
Tyr Val Lys Ser Asn Arg Leu Val Leu Ala Thr Gly Leu Arg Asn Ser
            325                 330                 335 cct cag cga gag act aga ggc ctg ttt ggc gcc att gct gga ttc att   1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac   1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag   1152
Ser Asn Glu Gln Gly Ser Gly Tyr Ala Ala Asp Lys Glu Ser Thr Gln
    370                 375                 380 aaa gca atc gat ggc gtc acc aac aaa gtc aat tca atc atc gac aaa   1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag   1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat   1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga   1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc   1392
Thr Leu Asp Phe His Asp Ser Asn Val Lys Asn Leu Tyr Asp Lys Val
    450                 455                 460 cgg ctc cag ctg agg gat aat gcc aag gaa ctc gga aat ggc tgc ttc   1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac   1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga   1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att   1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg   1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc   1680
Val Ala Gly Leu Ser Leu Trp Met Cys Ser Asn Gly Ser Leu Gln Cys
545                 550                 555                 560 cgg atc tgt atc tag                                               1695
Arg Ile Cys Ile <210> SEQ ID NO 8
<211> LENGTH: 564
<212> TYPE: PRT
<213> ORGANISM: Influenza virus

<400> SEQUENCE: 8

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45
```

```
Leu Glu Lys Thr His Asn Gly Lys Leu Cys Asp Leu Asp Gly Val Lys
     50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Val Asn Asp Leu Cys Tyr Pro Gly Asn Phe Thr
                100                 105                 110

Asp Tyr Glu Glu Leu Lys His Leu Leu Ser Arg Ile Asn His Phe Glu
                115                 120                 125

Lys Ile Gln Ile Ile Pro Lys Ser Ser Trp Ser Ser His Glu Ala Ser
        130                 135                 140

Leu Gly Val Ser Ser Ala Cys Pro Tyr Gln Arg Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
            355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
            435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
```

```
                465                 470                 475                 480
            Glu Phe Tyr His Lys Cys Asp Asn Glu Cys Met Glu Ser Val Arg Asn
                                485                 490                 495
            Gly Thr Tyr Asp Tyr Pro Gln Tyr Ser Glu Glu Ala Arg Leu Lys Arg
                            500                 505                 510
            Glu Glu Ile Ser Gly Val Lys Leu Glu Ser Ile Gly Ile Tyr Gln Ile
                        515                 520                 525
            Leu Ser Ile Tyr Ser Thr Val Ala Ser Ser Leu Ala Leu Ala Ile Met
                    530                 535                 540
            Val Ala Gly Leu Ser Leu Trp Met Cys Ser Asn Gly Ser Leu Gln Cys
            545                 550                 555                 560
            Arg Ile Cys Ile

<210> SEQ ID NO 9
<211> LENGTH: 1695
<212> TYPE: DNA
<213> ORGANISM: Influenza virus
<220> FEATURE:
<221> NAME/KEY: CDS
<222> LOCATION: (1)..(1695)

<400> SEQUENCE: 9 atg gag aaa att gtc ctg ctg ttc gcc att gtc tca ctg gtc aaa tcc     48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc     96
Asp Gln Ile Cys Ile Gly Tyr His Ala Asn Asn Ser Thr Glu Gln Val
                20                  25                  30 gac act att atg gaa aaa aac gtg acc gtc aca cat gct cag gat att    144
Asp Thr Ile Met Glu Lys Asn Val Thr Val Thr His Ala Gln Asp Ile
            35                  40                  45 ctc gaa aaa acc cac aac ggg aaa ctc tgt gat ctc gac gga gtg aaa    192
Leu Glu Lys Thr His Asn Gly Lys Leu Cys Asp Leu Asp Gly Val Lys
        50                  55                  60 cca ctc att ctg aga gac tgt agc gtc gct gga tgg ctc ctc ggc aat    240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg    288
Pro Met Cys Asp Glu Phe Ile Asn Val Pro Glu Trp Ser Tyr Ile Val
                85                  90                  95 gag aag gcc aac cct gtg aac gat ctc tgt tac cct ggc gac ttc aac    336
Glu Lys Ala Asn Pro Val Asn Asp Leu Cys Tyr Pro Gly Asp Phe Asn
                100                 105                 110 gat tac gag gaa ctg aaa cat ctg ctg agt agg atc aat cac ttt gaa    384
Asp Tyr Glu Glu Leu Lys His Leu Leu Ser Arg Ile Asn His Phe Glu
            115                 120                 125 aaa att cag att atc ccc aaa tct tcc tgg tcc tcc cat gag aac tct    432
Lys Ile Gln Ile Ile Pro Lys Ser Ser Trp Ser Ser His Glu Asn Ser
        130                 135                 140 tct ggc gtg tca tct gcc tgt cca tac cag agg aaa tcc tca ttc ttc    480
Ser Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc    528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg    576
Lys Arg Ser Tyr Asn Asn Thr Asn Gln Glu Asp Leu Leu Val Leu Trp
                180                 185                 190 gga att cat cac ccc aat gat gcc gcc gag cag aca aaa ctg tac cag    624
```

```
                Gly Ile His His Pro Asn Asp Ala Glu Gln Thr Lys Leu Tyr Gln
                        195                 200                 205 aac cct acc aca tac att tct gtg ggc acc tct aca ctg aat cag agg       672
Asn Pro Thr Thr Tyr Ile Ser Val Gly Thr Ser Thr Leu Asn Gln Arg
        210                 215                 220 ctg gtg cct aga att gcc act agg agt aaa gtc aac ggc cag tcc ggc       720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac       768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc       816
Phe Glu Ser Asn Gly Asn Phe Ile Ala Pro Glu Tyr Ala Tyr Lys Ile
            260                 265                 270 gtg aaa aag ggc gac tcc act atc atg aaa tcc gag ctg gag tac gga       864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct       912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa       960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca      1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att      1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac      1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag      1152
Ser Asn Glu Gln Gly Ser Gly Tyr Ala Ala Asp Lys Glu Ser Thr Gln
    370                 375                 380 aaa gca atc gat ggc gtc acc aac aaa gtc aat tca atc atc gac aaa      1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag      1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat      1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga      1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc      1392
Thr Leu Asp Phe His Asp Ser Asn Val Lys Asn Leu Tyr Asp Lys Val
    450                 455                 460 cgg ctc cag ctg agg gat aat gcc aag gaa ctc gga aat ggc tgc ttc      1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac      1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga      1536
Gly Thr Tyr Asp Tyr Pro Gln Tyr Ser Glu Glu Ala Arg Leu Lys Arg
            500                 505                 510
```

-continued

```
gag gag atc tct ggc gtc aaa ctg gag tct atc gga atc tac cag att    1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg    1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc    1680
Val Ala Gly Leu Ser Leu Trp Met Cys Ser Asn Gly Ser Leu Gln Cys
545                 550                 555                 560 cgg atc tgt atc tag                                                 1695
Arg Ile Cys Ile <210> SEQ ID NO 10
<211> LENGTH: 564
<212> TYPE: PRT
<213> ORGANISM: Influenza virus

<400> SEQUENCE: 10

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Asn Ser
    130                 135                 140

Ser Gly Val Ser Ser Ala Cys Pro Tyr Gln Arg Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300
```

```
Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
            325                 330                 335

Pro Gln Arg Glu Thr Arg Gly Leu Phe Gly Ala Ile Ala Gly Phe Ile
        340                 345                 350

Glu Gly Gly Trp Gln Gly Met Val Asp Gly Trp Tyr Gly Tyr His His
    355                 360                 365

Ser Asn Glu Gln Gly Ser Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 11
<211> LENGTH: 1695
<212> TYPE: DNA
<213> ORGANISM: Influenza virus
<220> FEATURE:
<221> NAME/KEY: CDS
<222> LOCATION: (1)..(1695)

<400> SEQUENCE: 11 atg gag aaa att gtc ctg ctg ttc gcc att gtc tca ctg gtc aaa tcc    48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc    96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att   144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa   192
Leu Glu Lys Thr His Asn Gly Lys Leu Cys Asp Leu Asp Gly Val Lys
    50                  55                  60 cca ctc att ctg aga gac tgt agc gtc gct gga tgg ctc ctc ggc aat   240
Pro Leu Ile Leu Arg Asp Cys Ser Val Ala Gly Trp Leu Leu Gly Asn
```

```
              Pro Leu Ile Leu Arg Asp Cys Ser Val Ala Gly Trp Leu Leu Gly Asn
              65                  70                  75                  80 cca atg tgt gat gag ttc atc aac gtc ccc gaa tgg tca tac atc gtg           288
Pro Met Cys Asp Glu Phe Ile Asn Val Pro Glu Trp Ser Tyr Ile Val
                    85                  90                  95 gag aag gcc aac cct gtg aac gat ctc tgt tac cct ggc gac ttc aac           336
Glu Lys Ala Asn Pro Val Asn Asp Leu Cys Tyr Pro Gly Asp Phe Asn
                100                 105                 110 gat tac gag gaa ctg aaa cat ctg ctg agt agg atc aat cac ttt gaa           384
Asp Tyr Glu Glu Leu Lys His Leu Leu Ser Arg Ile Asn His Phe Glu
            115                 120                 125 aaa att cag att atc ccc aaa tct tcc tgg tcc tcc cat gag gca tct           432
Lys Ile Gln Ile Ile Pro Lys Ser Ser Trp Ser Ser His Glu Ala Ser
    130                 135                 140 ctg ggc gtg tca tct gcc tgt cca tac aac agg acc tcc tca ttc ttc           480
Leu Gly Val Ser Ser Ala Cys Pro Tyr Asn Arg Thr Ser Ser Phe Phe
145                 150                 155                 160 cgg aac gtg gtg tgg ctc atc aaa aaa aac tcc acc tac ccc acc atc           528
Arg Asn Val Val Trp Leu Ile Lys Lys Asn Ser Thr Tyr Pro Thr Ile
                    165                 170                 175 aaa cgc tct tac aac aac aca aat cag gag gat ctg ctg gtc ctc tgg           576
Lys Arg Ser Tyr Asn Asn Thr Asn Gln Glu Asp Leu Leu Val Leu Trp
                180                 185                 190 gga att cat cac ccc aat gat gcc gcc gag cag aca aaa ctg tac cag           624
Gly Ile His His Pro Asn Asp Ala Ala Glu Gln Thr Lys Leu Tyr Gln
            195                 200                 205 aac cct acc aca tac att tct gtg ggc acc tct aca ctg aat cag agg           672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc           720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac           768
Arg Met Glu Phe Phe Trp Thr Ile Leu Lys Pro Asn Asp Ala Ile Asn
                    245                 250                 255 ttc gag tca aac ggc aac ttt atc gcc cct gaa tac gcc tac aaa atc           816
Phe Glu Ser Asn Gly Asn Phe Ile Ala Pro Glu Tyr Ala Tyr Lys Ile
                260                 265                 270 gtg aaa aag ggc gac tcc act atc atg aaa tcc gag ctg gag tac gga           864
Val Lys Lys Gly Asp Ser Thr Ile Met Lys Ser Glu Leu Glu Tyr Gly
            275                 280                 285 aac tgt aac acc aaa tgc cag acc cct atg ggc gct atc aac tct tct           912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa           960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca          1008
Tyr Val Lys Ser Asn Arg Leu Val Leu Ala Thr Gly Leu Arg Asn Ser
                    325                 330                 335 cct cag cga gag act aga ggc ctg ttt ggc gcc att gct gga ttc att          1056
Pro Gln Arg Glu Thr Arg Gly Leu Phe Gly Ala Ile Ala Gly Phe Ile
                340                 345                 350 gag gga ggc tgg cag gga atg gtc gat ggc tgg tac gga tac cat cac          1104
Glu Gly Gly Trp Gln Gly Met Val Asp Gly Trp Tyr Gly Tyr His His
            355                 360                 365 tcc aat gag cag gga tct gga tac gct gcc gat aag gag tcc acc cag          1152
Ser Asn Glu Gln Gly Ser Gly Tyr Ala Ala Asp Lys Glu Ser Thr Gln
    370                 375                 380
```

```
aaa gca atc gat ggc gtc acc aac aaa gtc aat tca atc atc gac aaa    1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag    1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat    1296
Arg Arg Ile Glu Asn Leu Asn Lys Lys Met Glu Asp Gly Phe Leu Asp
            420                 425                 430 gtg tgg acc tac aat gct gaa ctg ctg gtc ctc atg gaa aac gag aga    1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc    1392
Thr Leu Asp Phe His Asp Ser Asn Val Lys Asn Leu Tyr Asp Lys Val
    450                 455                 460 cgg ctc cag ctg agg gat aat gcc aag gaa ctc gga aat ggc tgc ttc    1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac    1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga    1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att    1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg    1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc    1680
Val Ala Gly Leu Ser Leu Trp Met Cys Ser Asn Gly Ser Leu Gln Cys
545                 550                 555                 560 cgg atc tgt atc tag                                                 1695
Arg Ile Cys Ile
```

<210> SEQ ID NO 12
<211> LENGTH: 564
<212> TYPE: PRT
<213> ORGANISM: Influenza virus

<400> SEQUENCE: 12

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125
```

-continued

Lys Ile Gln Ile Ile Pro Lys Ser Ser Trp Ser Ser His Glu Ala Ser
130                 135                 140

Leu Gly Val Ser Ser Ala Cys Pro Tyr Asn Arg Thr Ser Ser Phe Phe
145                 150                 155                 160

Arg Asn Val Val Trp Leu Ile Lys Lys Asn Ser Thr Tyr Pro Thr Ile
            165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
            325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
            405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
            435                 440                 445

Thr Leu Asp Phe His Asp Ser Asn Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
            485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
        515                 520                 525

Leu Ser Ile Tyr Ser Thr Val Ala Ser Ser Leu Ala Leu Ala Ile Met
530                 535                 540

Val Ala Gly Leu Ser Leu Trp Met Cys Ser Asn Gly Ser Leu Gln Cys

Arg Ile Cys Ile

<210> SEQ ID NO 13
<211> LENGTH: 1695
<212> TYPE: DNA
<213> ORGANISM: Influenza virus
<220> FEATURE:
<221> NAME/KEY: CDS
<222> LOCATION: (1)..(1695)

<400> SEQUENCE: 13

| | | | | | | | | | | | | | | | | |
|---|---|---|---|---|---|---|---|---|---|---|---|---|---|---|---|---|
| atg | gag | aaa | att | gtc | ctg | ctg | ttc | gcc | att | gtc | tca | ctg | gtc | aaa | tcc | 48 |
| Met | Glu | Lys | Ile | Val | Leu | Leu | Phe | Ala | Ile | Val | Ser | Leu | Val | Lys | Ser | |
| 1 | | | | 5 | | | | | 10 | | | | | 15 | | |
| gat | cag | atc | tgt | att | ggc | tac | cac | gcc | aac | aat | agc | act | gaa | cag | gtc | 96 |
| Asp | Gln | Ile | Cys | Ile | Gly | Tyr | His | Ala | Asn | Asn | Ser | Thr | Glu | Gln | Val | |
| | | | 20 | | | | | 25 | | | | | 30 | | | |
| gac | act | att | atg | gaa | aaa | aac | gtg | acc | gtc | aca | cat | gct | cag | gat | att | 144 |
| Asp | Thr | Ile | Met | Glu | Lys | Asn | Val | Thr | Val | Thr | His | Ala | Gln | Asp | Ile | |
| | | | | 35 | | | | | 40 | | | | | 45 | | |
| ctc | gaa | aaa | acc | cac | aac | ggg | aaa | ctc | tgt | gat | ctc | gac | gga | gtg | aaa | 192 |
| Leu | Glu | Lys | Thr | His | Asn | Gly | Lys | Leu | Cys | Asp | Leu | Asp | Gly | Val | Lys | |
| | 50 | | | | | 55 | | | | | 60 | | | | | |
| cca | ctc | att | ctg | aga | gac | tgt | agc | gtc | gct | gga | tgg | ctc | ctc | ggc | aat | 240 |
| Pro | Leu | Ile | Leu | Arg | Asp | Cys | Ser | Val | Ala | Gly | Trp | Leu | Leu | Gly | Asn | |
| 65 | | | | | 70 | | | | | 75 | | | | | 80 | |
| cca | atg | tgt | gat | gag | ttc | atc | aac | gtc | ccc | gaa | tgg | tca | tac | atc | gtg | 288 |
| Pro | Met | Cys | Asp | Glu | Phe | Ile | Asn | Val | Pro | Glu | Trp | Ser | Tyr | Ile | Val | |
| | | | | 85 | | | | | 90 | | | | | 95 | | |
| gag | aag | gcc | aac | cct | gtg | aac | gat | ctc | tgt | tac | cct | ggc | gac | ttc | aac | 336 |
| Glu | Lys | Ala | Asn | Pro | Val | Asn | Asp | Leu | Cys | Tyr | Pro | Gly | Asp | Phe | Asn | |
| | | | 100 | | | | | 105 | | | | | 110 | | | |
| gat | tac | gag | gaa | ctg | aaa | cat | ctg | ctg | agt | agg | atc | aat | cac | ttt | gaa | 384 |
| Asp | Tyr | Glu | Glu | Leu | Lys | His | Leu | Leu | Ser | Arg | Ile | Asn | His | Phe | Glu | |
| | | 115 | | | | | 120 | | | | | 125 | | | | |
| aaa | att | cag | att | atc | ccc | aaa | tct | tcc | tgg | tcc | tcc | cat | gag | gca | tct | 432 |
| Lys | Ile | Gln | Ile | Ile | Pro | Lys | Ser | Ser | Trp | Ser | Ser | His | Glu | Ala | Ser | |
| | 130 | | | | | 135 | | | | | 140 | | | | | |
| ctg | ggc | gtg | tca | tct | gcc | tgt | cca | tac | cag | agg | aac | tcc | tca | ttc | ttc | 480 |
| Leu | Gly | Val | Ser | Ser | Ala | Cys | Pro | Tyr | Gln | Arg | Asn | Ser | Ser | Phe | Phe | |
| 145 | | | | | 150 | | | | | 155 | | | | | 160 | |
| cgg | aac | gtg | gtg | tgg | ctc | atc | aaa | aaa | aac | tcc | acc | tac | ccc | acc | atc | 528 |
| Arg | Asn | Val | Val | Trp | Leu | Ile | Lys | Lys | Asn | Ser | Thr | Tyr | Pro | Thr | Ile | |
| | | | | 165 | | | | | 170 | | | | | 175 | | |
| aaa | cgc | tct | tac | aac | aac | aca | aat | cag | gag | gat | ctg | ctg | gtc | ctc | tgg | 576 |
| Lys | Arg | Ser | Tyr | Asn | Asn | Thr | Asn | Gln | Glu | Asp | Leu | Leu | Val | Leu | Trp | |
| | | | 180 | | | | | 185 | | | | | 190 | | | |
| gga | att | cat | cac | ccc | aat | gat | gcc | gcc | gag | cag | aca | aaa | ctg | tac | cag | 624 |
| Gly | Ile | His | His | Pro | Asn | Asp | Ala | Ala | Glu | Gln | Thr | Lys | Leu | Tyr | Gln | |
| | | 195 | | | | | 200 | | | | | 205 | | | | |
| aac | cct | acc | aca | tac | att | tct | gtg | ggc | acc | tct | aca | ctg | aat | cag | agg | 672 |
| Asn | Pro | Thr | Thr | Tyr | Ile | Ser | Val | Gly | Thr | Ser | Thr | Leu | Asn | Gln | Arg | |
| | 210 | | | | | 215 | | | | | 220 | | | | | |
| ctg | gtg | cct | aga | att | gcc | act | agg | agt | aaa | gtc | aac | ggc | cag | tcc | ggc | 720 |
| Leu | Val | Pro | Arg | Ile | Ala | Thr | Arg | Ser | Lys | Val | Asn | Gly | Gln | Ser | Gly | |
| 225 | | | | | 230 | | | | | 235 | | | | | 240 | |
| cgg | atg | gaa | ttc | ttt | tgg | acc | atc | ctc | aaa | ccc | aac | gat | gct | atc | aac | 768 |
| Arg | Met | Glu | Phe | Phe | Trp | Thr | Ile | Leu | Lys | Pro | Asn | Asp | Ala | Ile | Asn | |
| | | | | 245 | | | | | 250 | | | | | 255 | | |

| | | |
|---|---|---|
| ttc gag tca aac ggc aac ttt atc gcc cct gaa tac gcc tac aaa atc<br>Phe Glu Ser Asn Gly Asn Phe Ile Ala Pro Glu Tyr Ala Tyr Lys Ile<br>260 265 270 | | 816 |
| gtg aaa aag ggc gac tcc act atc atg aaa tcc gag ctg gag tac gga<br>Val Lys Lys Gly Asp Ser Thr Ile Met Lys Ser Glu Leu Glu Tyr Gly<br>275 280 285 | | 864 |
| aac tgt aac acc aaa tgc cag acc cct atg ggc gct atc aac tct tct<br>Asn Cys Asn Thr Lys Cys Gln Thr Pro Met Gly Ala Ile Asn Ser Ser<br>290 295 300 | | 912 |
| atg ccc ttc cac aac atc cac cct ctc act atc ggc gaa tgc cca aaa<br>Met Pro Phe His Asn Ile His Pro Leu Thr Ile Gly Glu Cys Pro Lys<br>305 310 315 320 | | 960 |
| tac gtc aaa tca aac cgg ctc gtg ctg gct act ggg ctg aga aac tca<br>Tyr Val Lys Ser Asn Arg Leu Val Leu Ala Thr Gly Leu Arg Asn Ser<br>325 330 335 | | 1008 |
| cct cag cga gag act aga ggc ctg ttt ggc gcc att gct gga ttc att<br>Pro Gln Arg Glu Thr Arg Gly Leu Phe Gly Ala Ile Ala Gly Phe Ile<br>340 345 350 | | 1056 |
| gag gga ggc tgg cag gga atg gtc gat ggc tgg tac gga tac cat cac<br>Glu Gly Gly Trp Gln Gly Met Val Asp Gly Trp Tyr Gly Tyr His His<br>355 360 365 | | 1104 |
| tcc aat gag cag gga tct gga tac gct gcc gat aag gag tcc acc cag<br>Ser Asn Glu Gln Gly Ser Gly Tyr Ala Ala Asp Lys Glu Ser Thr Gln<br>370 375 380 | | 1152 |
| aaa gca atc gat ggc gtc acc aac aaa gtc aat tca atc atc gac aaa<br>Lys Ala Ile Asp Gly Val Thr Asn Lys Val Asn Ser Ile Ile Asp Lys<br>385 390 395 400 | | 1200 |
| atg aac acc cag ttc gag gct gtg gga cga gag ttc aat aac ctg gag<br>Met Asn Thr Gln Phe Glu Ala Val Gly Arg Glu Phe Asn Asn Leu Glu<br>405 410 415 | | 1248 |
| cgg aga atc gaa aac ctg aac aaa aaa atg gag gac ggc ttc ctc gat<br>Arg Arg Ile Glu Asn Leu Asn Lys Lys Met Glu Asp Gly Phe Leu Asp<br>420 425 430 | | 1296 |
| gtg tgg acc tac aat gct gaa ctg ctg gtg ctc atg gaa aac gag aga<br>Val Trp Thr Tyr Asn Ala Glu Leu Leu Val Leu Met Glu Asn Glu Arg<br>435 440 445 | | 1344 |
| acc ctg gac ttc cac gac tca aac gtg aaa aac ctg tac gac aaa gtc<br>Thr Leu Asp Phe His Asp Ser Asn Val Lys Asn Leu Tyr Asp Lys Val<br>450 455 460 | | 1392 |
| cgg ctc cag ctg agg gat aat gcc aag gaa ctc gga aat ggc tgc ttc<br>Arg Leu Gln Leu Arg Asp Asn Ala Lys Glu Leu Gly Asn Gly Cys Phe<br>465 470 475 480 | | 1440 |
| gag ttc tac cac aaa tgt gac aac gag tgt atg gag tct gtc cga aac<br>Glu Phe Tyr His Lys Cys Asp Asn Glu Cys Met Glu Ser Val Arg Asn<br>485 490 495 | | 1488 |
| gga acc tac gac tac cct cag tac tct gag gag gct aga ctg aaa cga<br>Gly Thr Tyr Asp Tyr Pro Gln Tyr Ser Glu Glu Ala Arg Leu Lys Arg<br>500 505 510 | | 1536 |
| gag gag atc tct ggc gtc aaa ctg gag tct atc gga atc tac cag att<br>Glu Glu Ile Ser Gly Val Lys Leu Glu Ser Ile Gly Ile Tyr Gln Ile<br>515 520 525 | | 1584 |
| ctg tcc atc tac tct act gtg gct tct tca ctg gct ctg gcc atc atg<br>Leu Ser Ile Tyr Ser Thr Val Ala Ser Ser Leu Ala Leu Ala Ile Met<br>530 535 540 | | 1632 |
| gtc gct ggg ctg tct ctg tgg atg tgc tca aat gga tca ctc cag tgc<br>Val Ala Gly Leu Ser Leu Trp Met Cys Ser Asn Gly Ser Leu Gln Cys<br>545 550 555 560 | | 1680 |
| cgg atc tgt atc tag<br>Arg Ile Cys Ile | | 1695 |

<210> SEQ ID NO 14
<211> LENGTH: 564
<212> TYPE: PRT
<213> ORGANISM: Influenza virus

<400> SEQUENCE: 14

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Arg Asn Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

```
Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 15
<211> LENGTH: 1695
<212> TYPE: DNA
<213> ORGANISM: Influenza virus
<220> FEATURE:
<221> NAME/KEY: CDS
<222> LOCATION: (1)..(1695)

<400> SEQUENCE: 15 atg gag aaa att gtc ctg ctg ttc gcc att gtc tca ctg gtc aaa tcc        48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc        96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att       144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa       192
Leu Glu Lys Thr His Asn Gly Lys Leu Cys Asp Leu Asp Gly Val Lys
    50                  55                  60 cca ctc att ctg aga gac tgt agc gtc gct gga tgg ctc ctc ggc aat       240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg       288
Pro Met Cys Asp Glu Phe Ile Asn Val Pro Glu Trp Ser Tyr Ile Val
                85                  90                  95 gag aag gcc aac cct gtg aac gat ctc tgt tac cct ggc gac ttc aac       336
Glu Lys Ala Asn Pro Val Asn Asp Leu Cys Tyr Pro Gly Asp Phe Asn
            100                 105                 110 gat tac gag gaa ctg aaa cat ctg ctg agt agg atc aat cac ttt gaa       384
Asp Tyr Glu Glu Leu Lys His Leu Leu Ser Arg Ile Asn His Phe Glu
        115                 120                 125
```

```
aaa att cag att atc ccc aaa tct tcc tgg tcc tcc cat gag gca tct    432
Lys Ile Gln Ile Ile Pro Lys Ser Ser Trp Ser Ser His Glu Ala Ser
130                 135                 140 ctg ggc gtg tca tct gcc tgt cca tac cag agg aaa tcc tca ttc ttc    480
Leu Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc    528
Arg Asn Val Val Trp Leu Ile Lys Lys Asn Ser Thr Tyr Pro Thr Ile
                165                 170                 175 aac cgc tct tac aac aac aca aat cag gag gat ctg ctg gtc ctc tgg    576
Asn Arg Ser Tyr Asn Asn Thr Asn Gln Glu Asp Leu Leu Val Leu Trp
            180                 185                 190 gga att cat cac ccc aat gat gcc gcc gag cag aca aaa ctg tac cag    624
Gly Ile His His Pro Asn Asp Ala Ala Glu Gln Thr Lys Leu Tyr Gln
        195                 200                 205 aac cct acc aca tac att tct gtg ggc acc tct aca ctg aat cag agg    672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc    720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac    768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc    816
Phe Glu Ser Asn Gly Asn Phe Ile Ala Pro Glu Tyr Ala Tyr Lys Ile
                260                 265                 270 gtg aaa aag ggc gac tcc act atc atg aaa tcc gag ctg gag tac gga    864
Val Lys Lys Gly Asp Ser Thr Ile Met Lys Ser Glu Leu Glu Tyr Gly
            275                 280                 285 aac tgt aac acc aaa tgc cag acc cct atg ggc gct atc aac tct tct    912
Asn Cys Asn Thr Lys Cys Gln Thr Pro Met Gly Ala Ile Asn Ser Ser
        290                 295                 300 atg ccc ttc cac aac atc cac cct ctc act atc ggc gaa tgc cca aaa    960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca   1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att   1056
Pro Gln Arg Glu Thr Arg Gly Leu Phe Gly Ala Ile Ala Gly Phe Ile
                340                 345                 350 gag gga ggc tgg cag gga atg gtc gat ggc tgg tac gga tac cat cac   1104
Glu Gly Gly Trp Gln Gly Met Val Asp Gly Trp Tyr Gly Tyr His His
            355                 360                 365 tcc aat gag cag gga tct gga tac gct gcc gat aag gag tcc acc cag   1152
Ser Asn Glu Gln Gly Ser Gly Tyr Ala Ala Asp Lys Glu Ser Thr Gln
        370                 375                 380 aaa gca atc gat ggc gtc acc aac aaa gtc aat tca atc atc gac aaa   1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag   1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat   1296
Arg Arg Ile Glu Asn Leu Asn Lys Lys Met Glu Asp Gly Phe Leu Asp
                420                 425                 430 gtg tgg acc tac aat gct gaa ctg ctg gtg ctc atg gaa aac gag aga   1344
Val Trp Thr Tyr Asn Ala Glu Leu Leu Val Leu Met Glu Asn Glu Arg
            435                 440                 445
```

```
acc ctg gac ttc cac gac tca aac gtg aaa aac ctg tac gac aaa gtc      1392
Thr Leu Asp Phe His Asp Ser Asn Val Lys Asn Leu Tyr Asp Lys Val
450                 455                 460 cgg ctc cag ctg agg gat aat gcc aag gaa ctc gga atg gc tgc ttc       1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac      1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga     1536
Gly Thr Tyr Asp Tyr Pro Gln Tyr Ser Glu Glu Ala Arg Leu Lys Arg
500                 505                 510 gag gag atc tct ggc gtc aaa ctg gag tct atc gga atc tac cag att     1584
Glu Glu Ile Ser Gly Val Lys Leu Glu Ser Ile Gly Ile Tyr Gln Ile
515                 520                 525 ctg tcc atc tac tct act gtg gct tct tca ctg gct ctg gcc atc atg     1632
Leu Ser Ile Tyr Ser Thr Val Ala Ser Ser Leu Ala Leu Ala Ile Met
530                 535                 540 gtc gct ggg ctg tct ctg tgg atg tgc tca aat gga tca ctc cag tgc     1680
Val Ala Gly Leu Ser Leu Trp Met Cys Ser Asn Gly Ser Leu Gln Cys
545                 550                 555                 560 cgg atc tgt atc tag                                                  1695
Arg Ile Cys Ile <210> SEQ ID NO 16
<211> LENGTH: 564
<212> TYPE: PRT
<213> ORGANISM: Influenza virus

<400> SEQUENCE: 16

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Arg Lys Ser Ser Phe Phe
145                 150                 155                 160

Arg Asn Val Val Trp Leu Ile Lys Lys Asn Ser Thr Tyr Pro Thr Ile
                165                 170                 175

Asn Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205
```

Asn Pro Thr Thr Tyr Ile Ser Val Gly Thr Ser Thr Leu Asn Gln Arg
210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
            275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
                340                 345                 350

Glu Gly Gly Trp Gln Gly Met Val Asp Gly Trp Tyr Gly Tyr His His
            355                 360                 365

Ser Asn Glu Gln Gly Ser Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
                420                 425                 430

Val Trp Thr Tyr Asn Ala Glu Leu Leu Val Leu Met Glu Asn Glu Arg
            435                 440                 445

Thr Leu Asp Phe His Asp Ser Asn Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Ala Arg Leu Lys Arg
            500                 505                 510

Glu Glu Ile Ser Gly Val Lys Leu Glu Ser Ile Gly Ile Tyr Gln Ile
            515                 520                 525

Leu Ser Ile Tyr Ser Thr Val Ala Ser Ser Leu Ala Leu Ala Ile Met
530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 17
<211> LENGTH: 1695
<212> TYPE: DNA
<213> ORGANISM: Influenza virus
<220> FEATURE:
<221> NAME/KEY: CDS
<222> LOCATION: (1)..(1695)

<400> SEQUENCE: 17

```
atg gag aaa att gtc ctg ctg ttc gcc att gtc tca ctg gtc aaa tcc     48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc     96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att    144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa    192
Leu Glu Lys Thr His Asn Gly Lys Leu Cys Asp Leu Asp Gly Val Lys
    50                  55                  60 cca ctc att ctg aga gac tgt agc gtc gct gga tgg ctc ctc ggc aat    240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg    288
Pro Met Cys Asp Glu Phe Ile Asn Val Pro Glu Trp Ser Tyr Ile Val
                85                  90                  95 gag aag gcc aac cct gtg aac gat ctc tgt tac cct ggc gac ttc aac    336
Glu Lys Ala Asn Pro Val Asn Asp Leu Cys Tyr Pro Gly Asp Phe Asn
            100                 105                 110 gat tac gag gaa ctg aaa cat ctg ctg agt agg atc aat cac ttt gaa    384
Asp Tyr Glu Glu Leu Lys His Leu Leu Ser Arg Ile Asn His Phe Glu
        115                 120                 125 aaa att cag att atc ccc aaa tct tcc tgg tcc tcc cat gag gca tct    432
Lys Ile Gln Ile Ile Pro Lys Ser Ser Trp Ser Ser His Glu Ala Ser
    130                 135                 140 ctg ggc gtg tca tct gcc tgt cca tac cag agg aaa tcc tca ttc ttc    480
Leu Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc    528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg    576
Lys Arg Ser Tyr Asn Asn Thr Asn Gln Glu Asp Leu Leu Val Leu Trp
            180                 185                 190 gga att cat cac tct aat gat aca gcc gag cag aca aaa ctg tac cag    624
Gly Ile His His Ser Asn Asp Thr Ala Glu Gln Thr Lys Leu Tyr Gln
        195                 200                 205 aac cct acc aca tac att tct gtg ggc acc tct aca ctg aat cag agg    672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc    720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac    768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc    816
Phe Glu Ser Asn Gly Asn Phe Ile Ala Pro Glu Tyr Ala Tyr Lys Ile
            260                 265                 270 gtg aaa aag ggc gac tcc act atc atg aaa tcc gag ctg gag tac gga    864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct    912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa    960
Met Pro Phe His Asn Ile His Pro Leu Thr Ile Gly Glu Cys Pro Lys
305                 310                 315                 320
```

```
tac gtc aaa tca aac cgg ctc gtg ctg gct act ggg ctg aga aac tca   1008
Tyr Val Lys Ser Asn Arg Leu Val Leu Ala Thr Gly Leu Arg Asn Ser
            325                 330                 335 cct cag cga gag act aga ggc ctg ttt ggc gcc att gct gga ttc att   1056
Pro Gln Arg Glu Thr Arg Gly Leu Phe Gly Ala Ile Ala Gly Phe Ile
        340                 345                 350 gag gga ggc tgg cag gga atg gtc gat ggc tgg tac gga tac cat cac   1104
Glu Gly Gly Trp Gln Gly Met Val Asp Gly Trp Tyr Gly Tyr His His
    355                 360                 365 tcc aat gag cag gga tct gga tac gct gcc gat aag gag tcc acc cag   1152
Ser Asn Glu Gln Gly Ser Gly Tyr Ala Ala Asp Lys Glu Ser Thr Gln
370                 375                 380 aaa gca atc gat ggc gtc acc aac aaa gtc aat tca atc atc gac aaa   1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag   1248
Met Asn Thr Gln Phe Glu Ala Val Gly Arg Glu Phe Asn Asn Leu Glu
            405                 410                 415 cgg aga atc gaa aac ctg aac aaa aaa atg gag gac ggc ttc ctc gat   1296
Arg Arg Ile Glu Asn Leu Asn Lys Lys Met Glu Asp Gly Phe Leu Asp
        420                 425                 430 gtg tgg acc tac aat gct gaa ctg ctg gtg ctc atg gaa aac gag aga   1344
Val Trp Thr Tyr Asn Ala Glu Leu Leu Val Leu Met Glu Asn Glu Arg
    435                 440                 445 acc ctg gac ttc cac gac tca aac gtg aaa aac ctg tac gac aaa gtc   1392
Thr Leu Asp Phe His Asp Ser Asn Val Lys Asn Leu Tyr Asp Lys Val
450                 455                 460 cgg ctc cag ctg agg gat aat gcc aag gaa ctc gga aat ggc tgc ttc   1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac   1488
Glu Phe Tyr His Lys Cys Asp Asn Glu Cys Met Glu Ser Val Arg Asn
            485                 490                 495 gga acc tac gac tac cct cag tac tct gag gag gct aga ctg aaa cga   1536
Gly Thr Tyr Asp Tyr Pro Gln Tyr Ser Glu Glu Ala Arg Leu Lys Arg
        500                 505                 510 gag gag atc tct ggc gtc aaa ctg gag tct atc gga atc tac cag att   1584
Glu Glu Ile Ser Gly Val Lys Leu Glu Ser Ile Gly Ile Tyr Gln Ile
    515                 520                 525 ctg tcc atc tac tct act gtg gct tct tca ctg gct ctg gcc atc atg   1632
Leu Ser Ile Tyr Ser Thr Val Ala Ser Ser Leu Ala Leu Ala Ile Met
530                 535                 540 gtc gct ggg ctg tct ctg tgg atg tgc tca aat gga tca ctc cag tgc   1680
Val Ala Gly Leu Ser Leu Trp Met Cys Ser Asn Gly Ser Leu Gln Cys
545                 550                 555                 560 cgg atc tgt atc tag                                                1695
Arg Ile Cys Ile <210> SEQ ID NO 18
<211> LENGTH: 564
<212> TYPE: PRT
<213> ORGANISM: Influenza virus

<400> SEQUENCE: 18

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr

-continued

```
                35                  40                  45
Leu Glu Lys Thr His Asn Gly Lys Leu Cys Asp Leu Asp Gly Val Lys
        50                  55                  60
Pro Leu Ile Leu Arg Asp Cys Ser Val Ala Gly Trp Leu Leu Gly Asn
 65                  70                  75                  80
Pro Met Cys Asp Glu Phe Ile Asn Val Pro Glu Trp Ser Tyr Ile Val
                85                  90                  95
Glu Lys Ala Asn Pro Val Asn Asp Leu Cys Tyr Pro Gly Asp Phe Asn
                100                 105                 110
Asp Tyr Glu Glu Leu Lys His Leu Leu Ser Arg Ile Asn His Phe Glu
                115                 120                 125
Lys Ile Gln Ile Ile Pro Lys Ser Ser Trp Ser Ser His Glu Ala Ser
            130                 135                 140
Leu Gly Val Ser Ser Ala Cys Pro Tyr Gln Arg Lys Ser Ser Phe Phe
145                 150                 155                 160
Arg Asn Val Val Trp Leu Ile Lys Lys Asn Ser Thr Tyr Pro Thr Ile
                165                 170                 175
Lys Arg Ser Tyr Asn Asn Thr Asn Gln Glu Asp Leu Leu Val Leu Trp
                180                 185                 190
Gly Ile His His Ser Asn Asp Thr Ala Glu Gln Thr Lys Leu Tyr Gln
            195                 200                 205
Asn Pro Thr Thr Tyr Ile Ser Val Gly Thr Ser Thr Leu Asn Gln Arg
210                 215                 220
Leu Val Pro Arg Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
                260                 265                 270
Val Lys Lys Gly Asp Ser Thr Ile Met Lys Ser Glu Leu Glu Tyr Gly
            275                 280                 285
Asn Cys Asn Thr Lys Cys Gln Thr Pro Met Gly Ala Ile Asn Ser Ser
        290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Thr Arg Gly Leu Phe Gly Ala Ile Ala Gly Phe Ile
                340                 345                 350
Glu Gly Gly Trp Gln Gly Met Val Asp Gly Trp Tyr Gly Tyr His His
            355                 360                 365
Ser Asn Glu Gln Gly Ser Gly Tyr Ala Ala Asp Lys Glu Ser Thr Gln
        370                 375                 380
Lys Ala Ile Asp Gly Val Thr Asn Lys Val Asn Ser Ile Ile Asp Lys
385                 390                 395                 400
Met Asn Thr Gln Phe Glu Ala Val Gly Arg Glu Phe Asn Asn Leu Glu
                405                 410                 415
Arg Arg Ile Glu Asn Leu Asn Lys Lys Met Glu Asp Gly Phe Leu Asp
                420                 425                 430
Val Trp Thr Tyr Asn Ala Glu Leu Leu Val Leu Met Glu Asn Glu Arg
            435                 440                 445
Thr Leu Asp Phe His Asp Ser Asn Val Lys Asn Leu Tyr Asp Lys Val
450                 455                 460
```

```
Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
            485                 490                 495

Gly Thr Tyr Asp Tyr Pro Gln Tyr Ser Glu Glu Ala Arg Leu Lys Arg
        500                 505                 510

Glu Glu Ile Ser Gly Val Lys Leu Glu Ser Ile Gly Ile Tyr Gln Ile
            515                 520                 525

Leu Ser Ile Tyr Ser Thr Val Ala Ser Ser Leu Ala Leu Ala Ile Met
        530                 535                 540

Val Ala Gly Leu Ser Leu Trp Met Cys Ser Asn Gly Ser Leu Gln Cys
545                 550                 555                 560

Arg Ile Cys Ile
```

<210> SEQ ID NO 19
<211> LENGTH: 1695
<212> TYPE: DNA
<213> ORGANISM: Influenza virus
<220> FEATURE:
<221> NAME/KEY: CDS
<222> LOCATION: (1)..(1695)

<400> SEQUENCE: 19

```
atg gag aaa att gtc ctg ctg ttc gcc att gtc tca ctg gtc aaa tcc        48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc        96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att       144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa       192
Leu Glu Lys Thr His Asn Gly Lys Leu Cys Asp Leu Asp Gly Val Lys
    50                  55                  60 cca ctc att ctg aga gac tgt agc gtc gct gga tgg ctc ctc ggc aat       240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg       288
Pro Met Cys Asp Glu Phe Ile Asn Val Pro Glu Trp Ser Tyr Ile Val
                85                  90                  95 gag aag gcc aac cct gtg aac gat ctc tgt tac cct ggc gac ttc aac       336
Glu Lys Ala Asn Pro Val Asn Asp Leu Cys Tyr Pro Gly Asp Phe Asn
            100                 105                 110 gat tac gag gaa ctg aaa cat ctg ctg agt agg atc aat cac ttt gaa       384
Asp Tyr Glu Glu Leu Lys His Leu Leu Ser Arg Ile Asn His Phe Glu
        115                 120                 125 aaa att cag att atc ccc aaa tct tcc tgg tcc tcc cat gag gca tct       432
Lys Ile Gln Ile Ile Pro Lys Ser Ser Trp Ser Ser His Glu Ala Ser
    130                 135                 140 ctg ggc gtg tca tct gcc tgt cca tac cag agg aaa tcc tca ttc ttc       480
Leu Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc       528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg       576
Lys Arg Ser Tyr Asn Asn Thr Asn Gln Glu Asp Leu Leu Val Leu Trp
            180                 185                 190
```

```
gga att cat cac ccc aat gat gcc gcc gag cag aca aaa ctg tac cag      624
Gly Ile His His Pro Asn Asp Ala Ala Glu Gln Thr Lys Leu Tyr Gln
        195                 200                 205 aac cct acc aca tac att tct gtg ggc acc tct aca ctg aat cag agg      672
Asn Pro Thr Thr Tyr Ile Ser Val Gly Thr Ser Thr Leu Asn Gln Arg
210                 215                 220 ctg gtg cct aga att gcc act agg agt aaa gtc aac ggc cag tcc ggc      720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac      768
Arg Met Glu Phe Phe Trp Thr Ile Leu Lys Pro Asn Asp Ala Ile Asn
                245                 250                 255 ttc gag tca aac ggc aac ttt atc gcc cct gaa aac gcc acc aaa atc      816
Phe Glu Ser Asn Gly Asn Phe Ile Ala Pro Glu Asn Ala Thr Lys Ile
            260                 265                 270 gtg aaa aag ggc gac tcc act atc atg aaa tcc gag ctg gag tac gga      864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct      912
Asn Cys Asn Thr Lys Cys Gln Thr Pro Met Gly Ala Ile Asn Ser Ser
290                 295                 300 atg ccc ttc cac aac atc cac cct ctc act atc ggc gaa tgc cca aaa      960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca     1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att     1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac     1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag     1152
Ser Asn Glu Gln Gly Ser Gly Tyr Ala Ala Asp Lys Glu Ser Thr Gln
370                 375                 380 aaa gca atc gat ggc gtc acc aac aaa gtc aat tca atc atc gac aaa     1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag     1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat     1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga     1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc     1392
Thr Leu Asp Phe His Asp Ser Asn Val Lys Asn Leu Tyr Asp Lys Val
450                 455                 460 cgg ctc cag ctg agg gat aat gcc aag gaa ctc gga aat ggc tgc ttc     1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac     1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga     1536
Gly Thr Tyr Asp Tyr Pro Gln Tyr Ser Glu Glu Ala Arg Leu Lys Arg
```

```
                    500                 505                 510
gag gag atc tct ggc gtc aaa ctg gag tct atc gga atc tac cag att         1584
Glu Glu Ile Ser Gly Val Lys Leu Glu Ser Ile Gly Ile Tyr Gln Ile
            515                 520                 525 ctg tcc atc tac tct act gtg gct tct tca ctg gct ctg gcc atc atg         1632
Leu Ser Ile Tyr Ser Thr Val Ala Ser Ser Leu Ala Leu Ala Ile Met
530                 535                 540 gtc gct ggg ctg tct ctg tgg atg tgc tca aat gga tca ctc cag tgc         1680
Val Ala Gly Leu Ser Leu Trp Met Cys Ser Asn Gly Ser Leu Gln Cys
545                 550                 555                 560 cgg atc tgt atc tag                                                     1695
Arg Ile Cys Ile <210> SEQ ID NO 20
<211> LENGTH: 564
<212> TYPE: PRT
<213> ORGANISM: Influenza virus

<400> SEQUENCE: 20

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser His Glu Ala Ser
    130                 135                 140

Leu Gly Val Ser Ser Ala Cys Pro Tyr Gln Arg Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Thr Lys Ile
            260                 265                 270

Val Lys Lys Gly Asp Ser Thr Ile Met Lys Ser Glu Leu Glu Tyr Gly
        275                 280                 285
```

```
Asn Cys Asn Thr Lys Cys Gln Thr Pro Met Gly Ala Ile Asn Ser Ser
    290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Thr Arg Gly Leu Phe Gly Ala Ile Ala Gly Phe Ile
            340                 345                 350
Glu Gly Gly Trp Gln Gly Met Val Asp Gly Trp Tyr Gly Tyr His His
        355                 360                 365
Ser Asn Glu Gln Gly Ser Gly Tyr Ala Ala Asp Lys Glu Ser Thr Gln
    370                 375                 380
Lys Ala Ile Asp Gly Val Thr Asn Lys Val Asn Ser Ile Ile Asp Lys
385                 390                 395                 400
Met Asn Thr Gln Phe Glu Ala Val Gly Arg Glu Phe Asn Asn Leu Glu
                405                 410                 415
Arg Arg Ile Glu Asn Leu Asn Lys Lys Met Glu Asp Gly Phe Leu Asp
            420                 425                 430
Val Trp Thr Tyr Asn Ala Glu Leu Leu Val Leu Met Glu Asn Glu Arg
        435                 440                 445
Thr Leu Asp Phe His Asp Ser Asn Val Lys Asn Leu Tyr Asp Lys Val
    450                 455                 460
Arg Leu Gln Leu Arg Asp Asn Ala Lys Glu Leu Gly Asn Gly Cys Phe
465                 470                 475                 480
Glu Phe Tyr His Lys Cys Asp Asn Glu Cys Met Glu Ser Val Arg Asn
                485                 490                 495
Gly Thr Tyr Asp Tyr Pro Gln Tyr Ser Glu Glu Ala Arg Leu Lys Arg
            500                 505                 510
Glu Glu Ile Ser Gly Val Lys Leu Glu Ser Ile Gly Ile Tyr Gln Ile
        515                 520                 525
Leu Ser Ile Tyr Ser Thr Val Ala Ser Ser Leu Ala Leu Ala Ile Met
    530                 535                 540
Val Ala Gly Leu Ser Leu Trp Met Cys Ser Asn Gly Ser Leu Gln Cys
545                 550                 555                 560
Arg Ile Cys Ile

<210> SEQ ID NO 21
<211> LENGTH: 759
<212> TYPE: DNA
<213> ORGANISM: Influenza virus
<220> FEATURE:
<221> NAME/KEY: CDS
<222> LOCATION: (1)..(759)

<400> SEQUENCE: 21 atg agt ctt cta acc gag gtc gaa acg tat gtt ctc tct atc gtc ccg      48
Met Ser Leu Leu Thr Glu Val Glu Thr Tyr Val Leu Ser Ile Val Pro
1               5                   10                  15 tca ggc ccc ctc aaa gcc gag atc gca cag aga ctt gaa gat gtc ttt      96
Ser Gly Pro Leu Lys Ala Glu Ile Ala Gln Arg Leu Glu Asp Val Phe
                20                  25                  30 gca ggg aag aac acc gat ctt gag gtt ctc atg gaa tgg cta aag aca     144
Ala Gly Lys Asn Thr Asp Leu Glu Val Leu Met Glu Trp Leu Lys Thr
            35                  40                  45 aga cca atc ctg tca cct ctg act aag ggg att tta gga ttt gtg ttc     192
Arg Pro Ile Leu Ser Pro Leu Thr Lys Gly Ile Leu Gly Phe Val Phe
        50                  55                  60
```

```
acg ctc acc gtg ccc agt gag cgg gga ctg cag cgt aga cgc ttt gtc      240
Thr Leu Thr Val Pro Ser Glu Arg Gly Leu Gln Arg Arg Arg Phe Val
 65                  70                  75                  80 caa aat gct ctt aat ggg aac gga gat cca aat aac atg gac aaa gca      288
Gln Asn Ala Leu Asn Gly Asn Gly Asp Pro Asn Asn Met Asp Lys Ala
                 85                  90                  95 gtt aaa ctg tat agg aag ctt aag agg gag ata aca ttc cat ggg gcc      336
Val Lys Leu Tyr Arg Lys Leu Lys Arg Glu Ile Thr Phe His Gly Ala
            100                 105                 110 aaa gaa ata gca ctc agt tat tct gct ggt gca ctt gcc agt tgt atg      384
Lys Glu Ile Ala Leu Ser Tyr Ser Ala Gly Ala Leu Ala Ser Cys Met
        115                 120                 125 ggc ctc ata tac aac agg atg ggg gct gtg acc act gaa gtg gca ttt      432
Gly Leu Ile Tyr Asn Arg Met Gly Ala Val Thr Thr Glu Val Ala Phe
    130                 135                 140 ggc ctg gta tgc gca acc tgt gaa cag att gct gac tcc cag cat cgg      480
Gly Leu Val Cys Ala Thr Cys Glu Gln Ile Ala Asp Ser Gln His Arg
145                 150                 155                 160 tct cat agg caa atg gtg aca aca acc aat cca cta atc aga cat gag      528
Ser His Arg Gln Met Val Thr Thr Thr Asn Pro Leu Ile Arg His Glu
                165                 170                 175 aac aga atg gtt cta gcc agc act aca gct aag gct atg gag caa atg      576
Asn Arg Met Val Leu Ala Ser Thr Thr Ala Lys Ala Met Glu Gln Met
            180                 185                 190 gct gga tcg agt gag caa gca gca gag gcc atg gat att gct agt cag      624
Ala Gly Ser Ser Glu Gln Ala Ala Glu Ala Met Asp Ile Ala Ser Gln
        195                 200                 205 gcc agg caa atg gtg cag gcg atg aga acc att ggg act cat cct agc      672
Ala Arg Gln Met Val Gln Ala Met Arg Thr Ile Gly Thr His Pro Ser
    210                 215                 220 tcc agt gct ggt cta aaa gat gat ctt ctt gaa aat ttg cag gcc tat      720
Ser Ser Ala Gly Leu Lys Asp Asp Leu Leu Glu Asn Leu Gln Ala Tyr
225                 230                 235                 240 cag aaa cga atg ggg gtg cag atg caa cga ttc aag tga                  759
Gln Lys Arg Met Gly Val Gln Met Gln Arg Phe Lys
                245                 250

<210> SEQ ID NO 22
<211> LENGTH: 252
<212> TYPE: PRT
<213> ORGANISM: Influenza virus

<400> SEQUENCE: 22

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
```

```
              115                 120                 125
Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Asp Ile Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 23
<211> LENGTH: 294
<212> TYPE: DNA
<213> ORGANISM: Influenza virus
<220> FEATURE:
<221> NAME/KEY: CDS
<222> LOCATION: (1)..(294)

<400> SEQUENCE: 23 atg agt ctt cta acc gag gtc gaa acg cct atc aga aac gaa tgg ggg     48
Met Ser Leu Leu Thr Glu Val Glu Thr Pro Ile Arg Asn Glu Trp Gly
1               5                   10                  15 tgc aga tgc aac gat tca agt gat cct ctc gtc att gca gca aat atc     96
Cys Arg Cys Asn Asp Ser Ser Asp Pro Leu Val Ile Ala Ala Asn Ile
            20                  25                  30 att gga atc ttg cac ttg ata ttg tgg att ctt gat cgt ctt ttt ttc    144
Ile Gly Ile Leu His Leu Ile Leu Trp Ile Leu Asp Arg Leu Phe Phe
        35                  40                  45 aaa tgc att tat cgt cgc ttt aaa tac ggt ttg aaa aga ggg cct tct    192
Lys Cys Ile Tyr Arg Arg Phe Lys Tyr Gly Leu Lys Arg Gly Pro Ser
50                  55                  60 acg gaa gga gta cca gag tct atg agg gaa gaa tat cga aag gaa cag    240
Thr Glu Gly Val Pro Glu Ser Met Arg Glu Glu Tyr Arg Lys Glu Gln
65                  70                  75                  80 cag aat gct gtg gat gtt gac gat ggt cat ttt gtc aac ata gag ctg    288
Gln Asn Ala Val Asp Val Asp Asp Gly His Phe Val Asn Ile Glu Leu
                85                  90                  95 gag taa                                                            294
Glu

<210> SEQ ID NO 24
<211> LENGTH: 97
<212> TYPE: PRT
<213> ORGANISM: Influenza virus

<400> SEQUENCE: 24

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Ile Ala Ala Asn Ile
            20                  25                  30

Ile Gly Ile Leu His Leu Ile Leu Trp Ile Leu Asp Arg Leu Phe Phe
```

```
                    35                  40                  45
Lys Cys Ile Tyr Arg Arg Phe Lys Tyr Gly Leu Lys Arg Gly Pro Ser
     50                  55                  60

Thr Glu Gly Val Pro Glu Ser Met Arg Glu Glu Tyr Arg Lys Glu Gln
 65                  70                  75                  80

Gln Asn Ala Val Asp Val Asp Asp Gly His Phe Val Asn Ile Glu Leu
                 85                  90                  95

Glu

<210> SEQ ID NO 25
<211> LENGTH: 1860
<212> TYPE: DNA
<213> ORGANISM: Artificial
<220> FEATURE:
<223> OTHER INFORMATION: cDNA of FliC-M2 fusion protein
<220> FEATURE:
<221> NAME/KEY: CDS
<222> LOCATION: (1)..(1860)

<400> SEQUENCE: 25 atg aaa ttc tta gtc aac gtt gcc ctt gtt ttt atg gtc gtg tac att      48
Met Lys Phe Leu Val Asn Val Ala Leu Val Phe Met Val Val Tyr Ile
 1               5                  10                  15 tct tac atc tat gcg gcc gca caa gtc att aat aca aac agc ctg tcg      96
Ser Tyr Ile Tyr Ala Ala Ala Gln Val Ile Asn Thr Asn Ser Leu Ser
                 20                  25                  30 ctg ttg acc cag aat aac ctg aac aaa tcc cag tcc gct ctg ggc acc     144
Leu Leu Thr Gln Asn Asn Leu Asn Lys Ser Gln Ser Ala Leu Gly Thr
             35                  40                  45 gct atc gag cgt ctg tct tcc ggt ctg cgt atc aac agc gcg aaa gac     192
Ala Ile Glu Arg Leu Ser Ser Gly Leu Arg Ile Asn Ser Ala Lys Asp
     50                  55                  60 gat gcg gca ggt cag gcg att gct aac cgt ttt acc gcg aac atc aaa     240
Asp Ala Ala Gly Gln Ala Ile Ala Asn Arg Phe Thr Ala Asn Ile Lys
 65                  70                  75                  80 ggt ctg act cag gct tcc cgt aac gct aac gac ggt atc tcc att gcg     288
Gly Leu Thr Gln Ala Ser Arg Asn Ala Asn Asp Gly Ile Ser Ile Ala
                 85                  90                  95 cag acc act gaa ggc gcg ctg aac gaa atc aac aac aac ctg cag cgt     336
Gln Thr Thr Glu Gly Ala Leu Asn Glu Ile Asn Asn Asn Leu Gln Arg
                100                 105                 110 gtg cgt gaa ctg gcg gtt cag tct gct aac agc acc aac tcc cag tct     384
Val Arg Glu Leu Ala Val Gln Ser Ala Asn Ser Thr Asn Ser Gln Ser
            115                 120                 125 gac ctc gac tcc atc cag gct gaa atc acc cag cgc ctg aac gaa atc     432
Asp Leu Asp Ser Ile Gln Ala Glu Ile Thr Gln Arg Leu Asn Glu Ile
        130                 135                 140 gac cgt gta tcc ggc cag act cag ttc aac ggc gtg aaa gtc ctg gcg     480
Asp Arg Val Ser Gly Gln Thr Gln Phe Asn Gly Val Lys Val Leu Ala
145                 150                 155                 160 cag gac aac acc ctg acc atc cag gtt ggt gcc aac gac ggt gaa act     528
Gln Asp Asn Thr Leu Thr Ile Gln Val Gly Ala Asn Asp Gly Glu Thr
                165                 170                 175 atc gat atc gat ctg aag cag atc aac tct cag acc ctg ggt ctg gat     576
Ile Asp Ile Asp Leu Lys Gln Ile Asn Ser Gln Thr Leu Gly Leu Asp
            180                 185                 190 acg ctg aat gtg caa caa aaa tat aag gtc agc gat acg gct gca act     624
Thr Leu Asn Val Gln Gln Lys Tyr Lys Val Ser Asp Thr Ala Ala Thr
        195                 200                 205 gtt aca gga tat gcc gat act acg att gct tta gac aat agt act ttt     672
Val Thr Gly Tyr Ala Asp Thr Thr Ile Ala Leu Asp Asn Ser Thr Phe
```

```
                Val Thr Gly Tyr Ala Asp Thr Thr Ile Ala Leu Asp Asn Ser Thr Phe
                    210                 215                 220 aaa gcc tcg gct act ggt ctt ggt ggt act gac cag aaa att gat ggc         720
Lys Ala Ser Ala Thr Gly Leu Gly Gly Thr Asp Gln Lys Ile Asp Gly
225                 230                 235                 240 gat tta aaa ttt gat gat acg act gga aaa tat tac gcc aaa gtt acc         768
Asp Leu Lys Phe Asp Asp Thr Thr Gly Lys Tyr Tyr Ala Lys Val Thr
                245                 250                 255 gtt acg ggg gga act ggt aaa gat ggc tat tat gaa gtt tcc gtt gat         816
Val Thr Gly Gly Thr Gly Lys Asp Gly Tyr Tyr Glu Val Ser Val Asp
            260                 265                 270 aag acg aac ggt gag gtg act ctt gct ggc ggt gcg act tcc ccg ctt         864
Lys Thr Asn Gly Glu Val Thr Leu Ala Gly Gly Ala Thr Ser Pro Leu
        275                 280                 285 aca ggt gga cta cct gcg aca gca act gag gat gtg aaa aat gta caa         912
Thr Gly Gly Leu Pro Ala Thr Ala Thr Glu Asp Val Lys Asn Val Gln
    290                 295                 300 gtt gca aat gct gat ttg aca gag gct aaa gcc gca ttg aca gca gca         960
Val Ala Asn Ala Asp Leu Thr Glu Ala Lys Ala Ala Leu Thr Ala Ala
305                 310                 315                 320 ggt gtt acc ggc aca gca tct gtt gtt aag atg tct tat act gat aat        1008
Gly Val Thr Gly Thr Ala Ser Val Val Lys Met Ser Tyr Thr Asp Asn
                325                 330                 335 aac ggt aaa act att gat ggt ggt tta gca gtt aag gta ggc gat gat        1056
Asn Gly Lys Thr Ile Asp Gly Gly Leu Ala Val Lys Val Gly Asp Asp
                340                 345                 350 tac tat tct gca act caa aat aaa gat ggt tcc ata agt att aat act        1104
Tyr Tyr Ser Ala Thr Gln Asn Lys Asp Gly Ser Ile Ser Ile Asn Thr
            355                 360                 365 acg aaa tac act gca gat gac ggt aca tcc aaa act gca cta aac aaa        1152
Thr Lys Tyr Thr Ala Asp Asp Gly Thr Ser Lys Thr Ala Leu Asn Lys
        370                 375                 380 ctg ggt ggc gca gac ggc aaa acc gaa gtt gtt tct att ggt ggt aaa        1200
Leu Gly Gly Ala Asp Gly Lys Thr Glu Val Val Ser Ile Gly Gly Lys
385                 390                 395                 400 act tac gct gca agt aaa gcc gaa ggt cac aac ttt aaa gca cag cct        1248
Thr Tyr Ala Ala Ser Lys Ala Glu Gly His Asn Phe Lys Ala Gln Pro
                405                 410                 415 gat ctg gcg gaa gcg gct gct aca acc acc gaa aac ccg ctg cag aaa        1296
Asp Leu Ala Glu Ala Ala Ala Thr Thr Thr Glu Asn Pro Leu Gln Lys
            420                 425                 430 att gat gct gct ttg gca cag gtt gac acg tta cgt tct gac ctg ggt        1344
Ile Asp Ala Ala Leu Ala Gln Val Asp Thr Leu Arg Ser Asp Leu Gly
        435                 440                 445 gcg gta cag aac cgt ttc aac tcc gct att acc aac ctg ggc aac acc        1392
Ala Val Gln Asn Arg Phe Asn Ser Ala Ile Thr Asn Leu Gly Asn Thr
450                 455                 460 gta aac aac ctg act tct gcc cgt agc cgt atc gaa gat tcc gac tac        1440
Val Asn Asn Leu Thr Ser Ala Arg Ser Arg Ile Glu Asp Ser Asp Tyr
465                 470                 475                 480 gcg acc gaa gtt tcc aac atg tct cgc gcg cag att ctg cag cag gcc        1488
Ala Thr Glu Val Ser Asn Met Ser Arg Ala Gln Ile Leu Gln Gln Ala
                485                 490                 495 ggt acc tcc gtt ctg gcg cag gcg aac cag gtt ccg caa aac gtc ctc        1536
Gly Thr Ser Val Leu Ala Gln Ala Asn Gln Val Pro Gln Asn Val Leu
            500                 505                 510 tct tta ctg cgt gga gga gga gga gga atg agt ctt cta acc gag            1584
Ser Leu Leu Arg Gly Gly Gly Gly Gly Met Ser Leu Leu Thr Glu
        515                 520                 525
```

```
gtc gaa acg cct atc aga aac gaa tgg ggg tgc aga tgc aac gat tca    1632
Val Glu Thr Pro Ile Arg Asn Glu Trp Gly Cys Arg Cys Asn Asp Ser
            530             535             540 agt gat cct ctc gtc att gca gca aat atc att gga atc ttg cac ttg    1680
Ser Asp Pro Leu Val Ile Ala Ala Asn Ile Ile Gly Ile Leu His Leu
545                 550             555                 560 ata ttg tgg att ctt gat cgt ctt ttt ttc aaa tgc att tat cgt cgc    1728
Ile Leu Trp Ile Leu Asp Arg Leu Phe Phe Lys Cys Ile Tyr Arg Arg
                565             570             575 ttt aaa tac ggt ttg aaa aga ggg cct tct acg gaa gga gtg cca gag    1776
Phe Lys Tyr Gly Leu Lys Arg Gly Pro Ser Thr Glu Gly Val Pro Glu
            580             585             590 tct atg agg gaa gaa tat cga aag gaa cag cag aat gct gtg gat gtt    1824
Ser Met Arg Glu Glu Tyr Arg Lys Glu Gln Gln Asn Ala Val Asp Val
595             600             605 gac gat ggt cat ttt gtc aac ata gag ctg gag taa                    1860
Asp Asp Gly His Phe Val Asn Ile Glu Leu Glu
    610             615
```

<210> SEQ ID NO 26
<211> LENGTH: 619
<212> TYPE: PRT
<213> ORGANISM: Artificial
<220> FEATURE:
<223> OTHER INFORMATION: Synthetic Construct

<400> SEQUENCE: 26

```
Met Lys Phe Leu Val Asn Val Ala Leu Val Phe Met Val Val Tyr Ile
1               5                   10                  15

Ser Tyr Ile Tyr Ala Ala Ala Gln Val Ile Thr Asn Ser Leu Ser
            20                  25                  30

Leu Leu Thr Gln Asn Asn Leu Asn Lys Ser Gln Ser Ala Leu Gly Thr
        35                  40                  45

Ala Ile Glu Arg Leu Ser Ser Gly Leu Arg Ile Asn Ser Ala Lys Asp
    50                  55                  60

Asp Ala Ala Gly Gln Ala Ile Ala Asn Arg Phe Thr Ala Asn Ile Lys
65                  70                  75                  80

Gly Leu Thr Gln Ala Ser Arg Asn Ala Asn Asp Gly Ile Ser Ile Ala
                85                  90                  95

Gln Thr Thr Glu Gly Ala Leu Asn Glu Ile Asn Asn Asn Leu Gln Arg
            100                 105                 110

Val Arg Glu Leu Ala Val Gln Ser Ala Asn Ser Thr Asn Ser Gln Ser
        115                 120                 125

Asp Leu Asp Ser Ile Gln Ala Glu Ile Thr Gln Arg Leu Asn Glu Ile
    130                 135                 140

Asp Arg Val Ser Gly Gln Thr Gln Phe Asn Gly Val Lys Val Leu Ala
145                 150                 155                 160

Gln Asp Asn Thr Leu Thr Ile Gln Val Gly Ala Asn Asp Gly Glu Thr
                165                 170                 175

Ile Asp Ile Asp Leu Lys Gln Ile Asn Ser Gln Thr Leu Gly Leu Asp
            180                 185                 190

Thr Leu Asn Val Gln Gln Lys Tyr Lys Val Ser Asp Thr Ala Ala Thr
        195                 200                 205

Val Thr Gly Tyr Ala Asp Thr Thr Ile Ala Leu Asp Asn Ser Thr Phe
    210                 215                 220

Lys Ala Ser Ala Thr Gly Leu Gly Gly Thr Asp Gln Lys Ile Asp Gly
225                 230                 235                 240
```

Asp Leu Lys Phe Asp Asp Thr Thr Gly Lys Tyr Tyr Ala Lys Val Thr
            245                 250                 255

Val Thr Gly Gly Thr Gly Lys Asp Gly Tyr Tyr Glu Val Ser Val Asp
        260                 265                 270

Lys Thr Asn Gly Glu Val Thr Leu Ala Gly Gly Ala Thr Ser Pro Leu
            275                 280                 285

Thr Gly Gly Leu Pro Ala Thr Ala Thr Glu Asp Val Lys Asn Val Gln
        290                 295                 300

Val Ala Asn Ala Asp Leu Thr Glu Ala Lys Ala Leu Thr Ala Ala
305                 310                 315                 320

Gly Val Thr Gly Thr Ala Ser Val Val Lys Met Ser Tyr Thr Asp Asn
                325                 330                 335

Asn Gly Lys Thr Ile Asp Gly Leu Ala Val Lys Val Gly Asp Asp
            340                 345                 350

Tyr Tyr Ser Ala Thr Gln Asn Lys Asp Gly Ser Ile Ser Ile Asn Thr
        355                 360                 365

Thr Lys Tyr Thr Ala Asp Asp Gly Thr Ser Lys Thr Ala Leu Asn Lys
    370                 375                 380

Leu Gly Gly Ala Asp Gly Lys Thr Glu Val Val Ser Ile Gly Gly Lys
385                 390                 395                 400

Thr Tyr Ala Ala Ser Lys Ala Glu Gly His Asn Phe Lys Ala Gln Pro
                405                 410                 415

Asp Leu Ala Glu Ala Ala Ala Thr Thr Thr Glu Asn Pro Leu Gln Lys
            420                 425                 430

Ile Asp Ala Ala Leu Ala Gln Val Asp Thr Leu Arg Ser Asp Leu Gly
        435                 440                 445

Ala Val Gln Asn Arg Phe Asn Ser Ala Ile Thr Asn Leu Gly Asn Thr
    450                 455                 460

Val Asn Asn Leu Thr Ser Ala Arg Ser Arg Ile Glu Asp Ser Asp Tyr
465                 470                 475                 480

Ala Thr Glu Val Ser Asn Met Ser Arg Ala Gln Ile Leu Gln Gln Ala
                485                 490                 495

Gly Thr Ser Val Leu Ala Gln Ala Asn Gln Val Pro Gln Asn Val Leu
            500                 505                 510

Ser Leu Leu Arg Gly Gly Gly Gly Met Ser Leu Leu Thr Glu
        515                 520                 525

Val Glu Thr Pro Ile Arg Asn Glu Trp Gly Cys Arg Cys Asn Asp Ser
    530                 535                 540

Ser Asp Pro Leu Val Ile Ala Ala Asn Ile Ile Gly Ile Leu His Leu
545                 550                 555                 560

Ile Leu Trp Ile Leu Asp Arg Leu Phe Phe Lys Cys Ile Tyr Arg Arg
                565                 570                 575

Phe Lys Tyr Gly Leu Lys Arg Gly Pro Ser Thr Glu Gly Val Pro Glu
            580                 585                 590

Ser Met Arg Glu Glu Tyr Arg Lys Glu Gln Gln Asn Ala Val Asp Val
        595                 600                 605

Asp Asp Gly His Phe Val Asn Ile Glu Leu Glu
    610                 615

<210> SEQ ID NO 27
<211> LENGTH: 1350
<212> TYPE: DNA
<213> ORGANISM: Influenza virus
<220> FEATURE:
<221> NAME/KEY: CDS

<222> LOCATION: (1)..(1350)

<400> SEQUENCE: 27

| | | | | | | | | | | | | | | | | |
|---|---|---|---|---|---|---|---|---|---|---|---|---|---|---|---|---|
| atg | aat | cca | aat | cag | aag | ata | ata | acc | atc | gga | tca | atc | tgt | atg | gta | 48 |
| Met | Asn | Pro | Asn | Gln | Lys | Ile | Ile | Thr | Ile | Gly | Ser | Ile | Cys | Met | Val | |
| 1 | | | | 5 | | | | | 10 | | | | | 15 | | |

| act | gga | ata | gtt | agc | tta | atg | tta | caa | att | ggg | aac | atg | atc | tca | ata | 96 |
|---|---|---|---|---|---|---|---|---|---|---|---|---|---|---|---|---|
| Thr | Gly | Ile | Val | Ser | Leu | Met | Leu | Gln | Ile | Gly | Asn | Met | Ile | Ser | Ile | |
| | | | 20 | | | | | 25 | | | | | 30 | | | |

| tgg | gtc | agt | cat | tca | att | cac | aca | ggg | aat | caa | cac | caa | tct | gaa | cca | 144 |
|---|---|---|---|---|---|---|---|---|---|---|---|---|---|---|---|---|
| Trp | Val | Ser | His | Ser | Ile | His | Thr | Gly | Asn | Gln | His | Gln | Ser | Glu | Pro | |
| | | 35 | | | | | 40 | | | | | 45 | | | | |

| atc | agc | aat | act | aat | ttt | ctt | act | gag | aaa | gct | gtg | gct | tca | gta | aaa | 192 |
|---|---|---|---|---|---|---|---|---|---|---|---|---|---|---|---|---|
| Ile | Ser | Asn | Thr | Asn | Phe | Leu | Thr | Glu | Lys | Ala | Val | Ala | Ser | Val | Lys | |
| 50 | | | | | 55 | | | | | 60 | | | | | | |

| tta | gcg | ggc | aat | tca | tct | ctt | tgc | ccc | att | aac | gga | tgg | gct | gta | tac | 240 |
|---|---|---|---|---|---|---|---|---|---|---|---|---|---|---|---|---|
| Leu | Ala | Gly | Asn | Ser | Ser | Leu | Cys | Pro | Ile | Asn | Gly | Trp | Ala | Val | Tyr | |
| 65 | | | | 70 | | | | | 75 | | | | | 80 | | |

| agt | aag | gac | aac | agt | ata | agg | atc | ggt | tcc | aag | ggg | gat | gtg | ttt | gtt | 288 |
|---|---|---|---|---|---|---|---|---|---|---|---|---|---|---|---|---|
| Ser | Lys | Asp | Asn | Ser | Ile | Arg | Ile | Gly | Ser | Lys | Gly | Asp | Val | Phe | Val | |
| | | | | 85 | | | | | 90 | | | | | 95 | | |

| ata | aga | gag | ccg | ttc | atc | tca | tgc | tcc | cac | ttg | gaa | tgc | aga | act | ttc | 336 |
|---|---|---|---|---|---|---|---|---|---|---|---|---|---|---|---|---|
| Ile | Arg | Glu | Pro | Phe | Ile | Ser | Cys | Ser | His | Leu | Glu | Cys | Arg | Thr | Phe | |
| | | | 100 | | | | | 105 | | | | | 110 | | | |

| ttt | ttg | act | cag | gga | gcc | ttg | ctg | aat | gac | aag | cac | tcc | aat | ggg | act | 384 |
|---|---|---|---|---|---|---|---|---|---|---|---|---|---|---|---|---|
| Phe | Leu | Thr | Gln | Gly | Ala | Leu | Leu | Asn | Asp | Lys | His | Ser | Asn | Gly | Thr | |
| | | | 115 | | | | | 120 | | | | | 125 | | | |

| gtc | aaa | gac | aga | agc | cct | cac | aga | aca | tta | atg | agt | tgt | cct | gtg | ggt | 432 |
|---|---|---|---|---|---|---|---|---|---|---|---|---|---|---|---|---|
| Val | Lys | Asp | Arg | Ser | Pro | His | Arg | Thr | Leu | Met | Ser | Cys | Pro | Val | Gly | |
| 130 | | | | | 135 | | | | | 140 | | | | | | |

| gag | gct | ccc | tcc | cca | tat | aac | tca | agg | ttt | gag | tct | gtt | gct | tgg | tca | 480 |
|---|---|---|---|---|---|---|---|---|---|---|---|---|---|---|---|---|
| Glu | Ala | Pro | Ser | Pro | Tyr | Asn | Ser | Arg | Phe | Glu | Ser | Val | Ala | Trp | Ser | |
| 145 | | | | | 150 | | | | | 155 | | | | | 160 | |

| gca | agt | gct | tgc | cat | gat | ggc | acc | agt | tgg | ttg | acg | att | gga | att | tct | 528 |
|---|---|---|---|---|---|---|---|---|---|---|---|---|---|---|---|---|
| Ala | Ser | Ala | Cys | His | Asp | Gly | Thr | Ser | Trp | Leu | Thr | Ile | Gly | Ile | Ser | |
| | | | | 165 | | | | | 170 | | | | | 175 | | |

| ggc | cca | gac | aat | ggg | gct | gtg | gct | gta | ttg | aaa | tac | aat | ggc | ata | ata | 576 |
|---|---|---|---|---|---|---|---|---|---|---|---|---|---|---|---|---|
| Gly | Pro | Asp | Asn | Gly | Ala | Val | Ala | Val | Leu | Lys | Tyr | Asn | Gly | Ile | Ile | |
| | | | 180 | | | | | 185 | | | | | 190 | | | |

| aca | gac | act | atc | aag | agt | tgg | agg | aac | aac | ata | ctg | aga | act | caa | gag | 624 |
|---|---|---|---|---|---|---|---|---|---|---|---|---|---|---|---|---|
| Thr | Asp | Thr | Ile | Lys | Ser | Trp | Arg | Asn | Asn | Ile | Leu | Arg | Thr | Gln | Glu | |
| | | 195 | | | | | 200 | | | | | 205 | | | | |

| tct | gaa | tgt | gca | tgt | gta | aat | ggc | tct | tgc | ttt | act | gta | atg | act | gac | 672 |
|---|---|---|---|---|---|---|---|---|---|---|---|---|---|---|---|---|
| Ser | Glu | Cys | Ala | Cys | Val | Asn | Gly | Ser | Cys | Phe | Thr | Val | Met | Thr | Asp | |
| 210 | | | | | 215 | | | | | 220 | | | | | | |

| gga | cca | agt | aat | ggt | cag | gca | tca | cat | aag | atc | ttc | aaa | atg | gaa | aaa | 720 |
|---|---|---|---|---|---|---|---|---|---|---|---|---|---|---|---|---|
| Gly | Pro | Ser | Asn | Gly | Gln | Ala | Ser | His | Lys | Ile | Phe | Lys | Met | Glu | Lys | |
| 225 | | | | | 230 | | | | | 235 | | | | | 240 | |

| ggg | aaa | gtg | gtt | aaa | tca | gtc | gaa | ttg | gat | gct | cct | aat | tat | cac | tat | 768 |
|---|---|---|---|---|---|---|---|---|---|---|---|---|---|---|---|---|
| Gly | Lys | Val | Val | Lys | Ser | Val | Glu | Leu | Asp | Ala | Pro | Asn | Tyr | His | Tyr | |
| | | | | 245 | | | | | 250 | | | | | 255 | | |

| gag | gaa | tgc | tcc | tgt | tat | cct | aat | gcc | gga | gaa | atc | aca | tgt | gtg | tgc | 816 |
|---|---|---|---|---|---|---|---|---|---|---|---|---|---|---|---|---|
| Glu | Glu | Cys | Ser | Cys | Tyr | Pro | Asn | Ala | Gly | Glu | Ile | Thr | Cys | Val | Cys | |
| | | | 260 | | | | | 265 | | | | | 270 | | | |

| agg | gat | aat | tgg | cat | ggc | tca | aat | cgg | cca | tgg | gta | tct | ttc | aat | caa | 864 |
|---|---|---|---|---|---|---|---|---|---|---|---|---|---|---|---|---|
| Arg | Asp | Asn | Trp | His | Gly | Ser | Asn | Arg | Pro | Trp | Val | Ser | Phe | Asn | Gln | |
| | | 275 | | | | | 280 | | | | | 285 | | | | |

| aat | ttg | gag | tat | caa | ata | gga | tat | ata | tgc | agt | gga | gtt | ttc | gga | gac | 912 |
|---|---|---|---|---|---|---|---|---|---|---|---|---|---|---|---|---|
| Asn | Leu | Glu | Tyr | Gln | Ile | Gly | Tyr | Ile | Cys | Ser | Gly | Val | Phe | Gly | Asp | |
| 290 | | | | | 295 | | | | | 300 | | | | | | |

```
aat cca cgc ccc aat gat gga aca ggt agt tgt ggt ccg gtg tcc tct    960
Asn Pro Arg Pro Asn Asp Gly Thr Gly Ser Cys Gly Pro Val Ser Ser
305                 310                 315                 320 aac ggg gca tat ggg gta aaa ggg ttt tca ttt aaa tac ggc aat ggt    1008
Asn Gly Ala Tyr Gly Val Lys Gly Phe Ser Phe Lys Tyr Gly Asn Gly
                325                 330                 335 gtc tgg atc ggg aga acc aaa agc act aat tcc agg agc ggc ttt gaa    1056
Val Trp Ile Gly Arg Thr Lys Ser Thr Asn Ser Arg Ser Gly Phe Glu
            340                 345                 350 atg att tgg gat cca aat ggg tgg act gaa acg gac agt agc ttt tca    1104
Met Ile Trp Asp Pro Asn Gly Trp Thr Glu Thr Asp Ser Ser Phe Ser
        355                 360                 365 gtg aaa caa gat atc gta gca ata act gat tgg tca gga tat agc ggg    1152
Val Lys Gln Asp Ile Val Ala Ile Thr Asp Trp Ser Gly Tyr Ser Gly
    370                 375                 380 agt ttt gtc cag cat cca gaa ctg aca gga cta gat gca ata aga cct    1200
Ser Phe Val Gln His Pro Glu Leu Thr Gly Leu Asp Cys Ile Arg Pro
385                 390                 395                 400 tgt ttc tgg gtt gag ttg atc aga ggg cgg ccc aaa gag agc aca att    1248
Cys Phe Trp Val Glu Leu Ile Arg Gly Arg Pro Lys Glu Ser Thr Ile
                405                 410                 415 tgg act agt ggg agc agc ata tct ttt tgt ggt gta aat agt gac act    1296
Trp Thr Ser Gly Ser Ser Ile Ser Phe Cys Gly Val Asn Ser Asp Thr
            420                 425                 430 gtg ggt tgg tct tgg cca gac ggt gct gag ttg cca ttc acc att gac    1344
Val Gly Trp Ser Trp Pro Asp Gly Ala Glu Leu Pro Phe Thr Ile Asp
        435                 440                 445 aag tag                                                            1350
Lys

<210> SEQ ID NO 28
<211> LENGTH: 449
<212> TYPE: PRT
<213> ORGANISM: Influenza virus

<400> SEQUENCE: 28

Met Asn Pro Asn Gln Lys Ile Ile Thr Ile Gly Ser Ile Cys Met Val
1               5                   10                  15

Thr Gly Ile Val Ser Leu Met Leu Gln Ile Gly Asn Met Ile Ser Ile
                20                  25                  30

Trp Val Ser His Ser Ile His Thr Gly Asn Gln His Gln Ser Glu Pro
            35                  40                  45

Ile Ser Asn Thr Asn Phe Leu Thr Glu Lys Ala Val Ala Ser Val Lys
        50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
```

```
                    165                 170                 175
Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
        210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
            245                 250                 255

Glu Glu Cys Ser Cys Tyr Pro Asn Ala Gly Glu Ile Thr Cys Val Cys
            260                 265                 270

Arg Asp Asn Trp His Gly Ser Asn Arg Pro Trp Val Ser Phe Asn Gln
            275                 280                 285

Asn Leu Glu Tyr Gln Ile Gly Tyr Ile Cys Ser Gly Val Phe Gly Asp
            290                 295                 300

Asn Pro Arg Pro Asn Asp Gly Thr Gly Ser Cys Gly Pro Val Ser Ser
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Glu Thr Asp Ser Ser Phe Ser
            355                 360                 365

Val Lys Gln Asp Ile Val Ala Ile Thr Asp Trp Ser Gly Tyr Ser Gly
        370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Gly Trp Ser Trp Pro Asp Gly Ala Glu Leu Pro Phe Thr Ile Asp
            435                 440                 445

Lys
```